United States Patent [19]

Barenkamp

[11] Patent Number: 5,603,938
[45] Date of Patent: Feb. 18, 1997

[54] HIGH MOLECULAR WEIGHT SURFACE PROTEINS OF NON-TYPEABLE HAEMOPHILUS

[75] Inventor: Stephen J. Barenkamp, Webster Grove, Mo.

[73] Assignees: St. Louis University; Washington University, both of St. Louis, Mo.

[21] Appl. No.: 302,832

[22] PCT Filed: Mar. 16, 1993

[86] PCT No.: PCT/US93/02166

§ 371 Date: Oct. 5, 1994

§ 102(e) Date: Oct. 5, 1994

[87] PCT Pub. No.: WO93/19090

PCT Pub. Date: Sep. 30, 1993

[30] Foreign Application Priority Data

Mar. 16, 1992 [GB] United Kingdom .................. 9205704

[51] Int. Cl.$^6$ .................. A61K 39/102; C07H 19/00; C07H 21/00; C07H 21/02
[52] U.S. Cl. .................. 424/256.1; 536/22.1; 536/23.1; 536/23.7; 536/24.1; 435/69.1; 435/69.3
[58] Field of Search .................. 536/22.1, 23.7, 536/231, 23.1, 24.1; 530/300, 350; 435/69.1, 69.3, 91.1; 424/256.1

[56] References Cited

PUBLICATIONS

Pediatric Infectious Disease Journal, vol. 9, No. 5, issued May 1990, S.J. Barenkamp et al., "Development of Serum Bactericidal Activity Following Nontypable *Haemophilus influenzae* Acute Otitis Media", pp. 333–339, see entire document.

Journal of Clinical Microbiology, vol. 29, No. 11, issued Nov. 1991, A. C. Caputa et al., "110 Kilodalton Recombinant Protein which is Immunoreactive with Sera from Humans, Dogs, and Horses with Lyme Borreliosis", pp. 2416–2423, see entire document.

Joint Meeting of the American Pediatric Society and the Society for Pediatric Research, 7–10 May 1990, S. J. Barenkamp, "Cloning and Expression of Genes for Nontypable *Haemophilus influenzae* (NTH) High Molecular Weight (HMW) Outer Membrane Proteins which are Targets of Bactericidal Antibody", Abstract 983, Pediatric Research, vol. 27, (4 part 2).

The Journal of Infectious Diseases, vol. 165 (Suppl.), issued Aug 1992, S. J. Barenkamp, "Outer Membrane Protein and Lipopolysaccharides of Nontypeable *Haemophilus influenzae*", pp. S181–S184, see entire document.

Infection and Immunity, vol. 60(4), issued Apr. 1992, S. J. Barenkamp et al., "Cloning Expression and DNA Sequence Analysis of Genes Encoding Nontypable *Haemophilus influenzae* High–Molecular–Weight Surface–Exposed Proteins Related to Filamentous Hemegglutinin of *Bordetella pertussis*" pp. 1302–1313, see entire document.

Infection and Immunity, vol1 56(1), Issued Jan. 1988, E. J. Hansen, "Immune Enhancement of Pulmonary Clearance on Nontypable *Haemophilus Influenzae*," pp. 182–190, see entire document, especialty FIGS. 3 and 4.

Infection and Immunity, vol. 52(2), issued May 1986, S. J. Barenkamp, "Protection by Serum Antibodies in Experimental Nontypable *Haemophilus influenzae* Otitis Media", pp. 572–578, see FIGS. 1 and 2.

Proceedings of the National Academy of Sciences USA, vol. 80, issued Mar. 1983, R. A. Young et al., "Efficient Isolation of Genes by Using Antibody Probes", pp. 1194–1198, see entire document.

Infection and Immunity, vol. 45(3), issued Sep. 1984, R. Schneerson et al., "Serum Antibody Responses of Juvenile and Infant Rhesus Monkeys Injected with *Haemophilus influenzae* Type b and Pneumococcus Type 6A Capsular Polysaccharide–Protein Conjugates", pp. 582–591, see entire document.

Journal of Molecular Biology, vol. 157, issued 1982, J. Kyfe et al., "A Simple Method for Displaying the Hydropathic Character of a Protein", pp. 105–132, see entire document.

Proceedings of the National Academy of Sciences, vol. 78(6), issued Jun. 1981, T. P. Hopp et al. "Prediction of Protein Antigenic Determinants from Amino Acid Sequences", pp. 3824–3828, see entire document.

Pediatr. Infect. Dis. J., 9:333–339, 1990, Stephen J. Barenkamp and Frank F. Bodor, "Development of Serum Bacterial Activity Following Nontypable *Haemophilus influenzae* Acute Otitis Media".

Barenkamp et al., Infection & Immunity, 60:1302–1313, 1992.

Barenkamp et al. Pediatric Infect Dis Journ. 9: 333–339, 1990.

Barenkamp, Abstract 983, Pediatric Research vol. 27.

Young et al., PNAS 80:1194–1198, 1983.

Houghten et al. Vaccine 86 pp. 21–25.

Green et al, Infection and Immunity 61:1950–1957 1993.

Erwin et al. Can Journ of Microbiology 34: 723–729, 1988.

Thomas et al. Infection & Immunity 58:1909–1913, 1990.

Barenkamp, Pediatric Research vol. 20, N67A, Abstract 985, 1991.

*Primary Examiner*—Hazel F. Sidberry
*Attorney, Agent, or Firm*—Shoemaker and Mattare, Ltd.

[57] ABSTRACT

High molecular weight surface proteins of non-typeable *Haemophilus inflenzae* which exhibit immunogenic properties and genes encoding the same are described. Specifically, genes coding for two immunodominant high molecular weight proteins, HMW1 and HMW2, have been cloned, expressed and sequenced, while genes coding for high molecular proteins HMW3 and HMW4 have been cloned, expressed and partially sequenced.

3 Claims, 68 Drawing Sheets

FIG. 1A. DNA SEQUENCE OF HIGH MOLECULAR WEIGHT PROTEIN I (HMW1)

```
  1  ACAGCGTCT CTTAATACTA GTACAAACCC ACAATAAAAT ATGACAAACA
 51  ACAATTACAA CACCTTTTTT GCAGTCTATA TGCAAATATT TTAAAAATA
101  GTATAAATCC GCCATATAAA ATGGTATAAT CTTTCATCTT TCATCTTTCA
151  TCTTTCATCT TTCATCTTTC ATCTTTCATC TTTCATCTTT CATCTTTCAT
201  CTTTCATCTT TCATCTTTCA TCTTTCATCT TTCATCTTTC ACATGCCCTG
251  ATGAACCGAG GGAAGGGAGG GAGGGGCAAG AATGAAGAGG GAGCTGAACG
301  AACGCAAATG ATAAAGTAAT TTAATTGTTC AACTAACCTT AGGAGAAAAT
351  ATGAACAAGC TATATCGTCT CAAATTCAGC AAACGCCTGA ATGCTTTGGT
401  TGCTGTGTCT GAATTGGCAC GGGGTTGTGA CCATTCCACA GAAAAAGGCA
451  GCGAAAAACC TGCTCGCATG AAAGTGCGTC ACTTAGCGTT AAAGCCACTT
501  TCCGCTATGT TACTATCTTT AGGTGTAACA TCTATTCCAC AATCTGTTTT
551  AGCAAGCGGC TTACAAGGAA TGGATGTAGT ACACGGCACA GCCACTATGC
601  AAGTAGATGG TAATAAAACC ATTATCCGCA ACAGTGTTGA CGATATCATT
651  AATTGGAAAC AATTTAACAT CGACCAAAAT GAAATGGGTGC AGTTTTTACA
701  AGAAACAAC AACTCCGCCG TATTCAACCG TGTTACATCT AACCAAATCT
```

FIG. 1B.

```
 751  CCCAATTAAA AGGGATTTTA GATTCTAACG GACAAGTCTT TTTAATCAAC
 801  CCAAATGGTA TCACAATAGG TAAAGACGCA ATTATTAACA CTAATGGCTT
 851  TACGGCTTCT ACGCTAGACA TTTCTAACGA AAACATCAAG GCGCGTAATT
 901  TCACCTTCGA GCAAACCAAA GATAAAGCGC TCGCTGAAAT TGTGAATCAC
 951  GGTTTAATTA CTGTCGGTAA AGACGGCAGT GTAAATCTTA TTGGTGGCAA
1001  AGTGAAAAAC GAGGGTGTGA TTAGCGTAAA TGGTGGCAGC ATTTCTTTAC
1051  TCGCAGGGCA AAAAATCACC ATCAGCGATA TAATAAACCC AACCATTACT
1101  TACAGCATTG CCGCGCCTGA AAATGAAGCG GTCAATCTGG GCGATATTTT
1151  TGCCAAAGGC GGTAACATTA ATGTCCGTGC TGCCACTATT CGAAACCAAG
1201  GTAAACTTTC TGCTGATTCT GTAAGCAAAG ATAAAAGCGG CAATATTGTT
1251  CTTTCCGCCA AAGAGGGTGA AGCGGAAATT GGCGGTGTAA TTTCCGCTCA
1301  AAATCAGCAA GCTAAAGGCG GCAAGCTGAT GATTACAGGC GATAAAGTCA
1351  CATTAAAAAC AGGTGCAGTT ATCGACCTTT CAGGTAAAGA AGGGGAGAA
1401  ACTTACCTTG GCGGTGACGA GCGCGGCGAA GGTAAAAAGG GCATTCAATT
1451  AGCAAAGAAA ACCTCTTTAG AAAAAGGCTC AACCATCAAT GTATCAGGCA
1501  AAGAAAAAGG CGGACGCGCT ATTGTGTGGG GCGATATTGC GTTAATTGAC
```

FIG. 1C.

```
1551  GGCAATATTA  ACGCTCAAGG  TAGTGGTGAT  ATCGCTAAAA  CCGGTGGTTT
1601  TGTGGAGACG  TCGGGGCATG  ATTTATTCAT  CAAAGACAAT  GCAATTGTTG
1651  ACGCCAAAGA  GTGGTTGTTA  GACCCGGATA  ATGTATCTAT  TAATGCAGAA
1701  ACAGCAGGAC  GCAGCAATAC  TTCAGAAGAC  GATGAATACA  CGGGATCCGG
1751  GAATAGTGCC  AGCACCCCAA  AACGAAACAA  AGAAAAGACA  ACATTAACAA
1801  ACACAACTCT  TGAGAGTATA  CTAAAAAAAG  GTACCTTTGT  TAACATCACT
1851  GCTAATCAAC  GCATCTATGT  CAATAGCTCC  ATTAATTTAT  CCAATGGCAG
1901  CTTAACTCTT  TGGAGTGAGG  GTCGGAGCGG  TGGCGGCGTT  GAGATTAACA
1951  ACGATATTAC  CACCGGGTGAT  GATACCAGAG  GTGCAAACTT  AACAATTTAC
2001  TCAGGCGGCT  GGGTTGATGT  TCATAAAAAT  ATCTCACTCG  GGGCGCAAGG
2051  TAACATAAAC  ATTACAGCTA  AACAAGATAT  CGCCTTTGAG  AAAGGAAGCA
2101  ACCAAGTCAT  TACAGGTCAA  GGGACTATTA  CCTCAGGCAA  TCAAAAAGGT
2151  TTTAGATTTA  ATAATGTCTC  TCTAAACGGC  ACTGGCAGCG  GACTGCAATT
2201  CACCACTAAA  AGAACCAATA  AATACGCTAT  CACAAATAAA  TTTGAAGGGA
2251  CTTTAAATAT  TTCAGGGAAA  GTGAACATCT  CAATGGTTTT  ACCTAAAAAT
2301  GAAAGTGGAT  ATGATAAATT  CAAAGGACGC  ACTTACTGGA  ATTTAACCTC
```

FIG.1D.

```
2351  CTTAAATGTT  TCCGAGAGTG  GCGAGTTTAA  CCTCACTATT  GACTCCAGAG
2401  GAAGGGATAG  TGCAGGCACA  CTTACCCAGC  CTTATAATTT  AAACGGTATA
2451  TCATTCAACA  AAGACACTAC  CTTTAATGTT  GAACGAAATG  CAAGAGTCAA
2501  CTTTGACATC  AAGGCACCAA  TAGGGATAAA  TAAGTATTCT  AGTTTGAATT
2551  ACGCATCATT  TAATGGAAAC  ATTTCAGTTT  CGGGAGGGGG  GAGTGTTGAT
2601  TTCACACTTC  TCGCCTCATC  CTCTAACGTC  CAAACCCCCG  GTGTAGTTAT
2651  AAATTCTAAA  TACTTTAATG  TTTCAACAGG  GTCAAGTTTA  AGATTTAAAA
2701  CTTCAGGCTC  AACAAAAACT  GGCTTCTCAA  TAGAGAAAGA  TTTAACTTTA
2751  AATGCCACCG  GAGGCAACAT  AACACTTTTG  CAAGTTGAAG  GCACCGATGG
2801  AATGATTGGT  AAAGGCATTG  TAGCCAAAAA  AAACATAACC  TTTGAAGGAG
2851  GTAACATCAC  CTTTGGCTCC  AGGAAAGCCG  TAACAGAAAT  CGAAGGCAAT
2901  GTTACTATCA  ATAACAACGC  TAACGTCACT  CTTATCGGTT  CGGATTTTGA
2951  CAACCATCAA  AAACCTTTAA  CTATTAAAAA  AGATGTCATC  ATTAATAGCG
3001  GCAACCTTAC  CGCTGGAGGC  AATATTGTCA  ATATAGCCGG  AAATCTTACC
3051  GTTGAAAGTA  ACGCTAATTT  CAAAGCTATC  ACAAATTTCA  CTTTTAATGT
3101  AGGCGGCTTG  TTTGACAACA  AAGGCAATTC  AAATATTTCC  ATTGCCAAAG
3151  GAGGGGCTCG  CTTTAAAGAC  ATTGATAATT  CCAAGAATTT  AAGCATCACC
```

FIG. 1E.

```
3201 ACCAACTCCA GCTCCACTTA CCGCACTATT ATAAGCGGCA ATATAACCAA
3251 TAAAAACGGT GATTAAATA  TTACGAACGA AGGTAGTGAT ACTGAAATGC
3301 AAATTGGCGG CGATGTCTCG CAAAAAGAAG GTAATCTCAC GATTCTTCT
3351 GACAAAATCA ATATTACCAA ACAGATAACA ATCAAGGCAG GTGTTGATGG
3401 GGAGAATTCC GATTCAGACG CGACAAACAA TGCCAATCTA ACCATTAAAA
3451 CCAAAGAATT GAAATTAACG CAAGACCTAA ATATTTCAGG TTTCAATAAA
3501 GCAGAGATTA CAGCTAAAGA TGGTAGTGAT TTAACTATTG GTAACACCAA
3551 TAGTGCTGAT GGTACTAATG CCAAAAAAGT AACCTTTAAC CAGGTTAAAG
3601 ATTCAAAAAT CTCTGCTGAC GGTCACAAGG TGACACTACA CAGCAAAGTG
3651 GAAACATCCG GTAGTAATAA CAACACTGAA GATAGCAGTG ACAATAATGC
3701 CGGCTTAACT ATCGATGCAA AAAATGTAAC AGTAAACAAC AATATTACTT
3751 CTCACAAAGC AGTGAGCATC TCTGCGACAA GTGGAGAAAT TACCACTAAA
3801 ACAGGTACAA CCATTAACGC AACCACTGGT AACGTGGAGA TAACCGCTCA
3851 AACAGGTAGT ATCCTAGGTG GAATTGAGTC CAGCTCTGGC TCTGTAACAC
3901 TTACTGCAAC CGAGGGCGCT CTTGCTGTAA GCAATATTTC GGGCAACACC
3951 GTTACTGTTA CTGCAAATAG CGGTGCATTA ACCACTTTGG CAGGCTCTAC
```

FIG. 1F.

```
4001 AATTAAAGGA ACCGAGAGTG TAACCACTTC AAGTCAATCA GGCGATATCG
4051 GCGGTACGAT TTCTGGTGGC ACAGTAGAGG TTAAAGCAAC CGAAAGTTTA
4101 ACCACTCAAT CCAATTCAAA AATTAAAGCA ACAACAGGCG AGGCTAACGT
4151 AACAAGTGCA ACAGGTACAA TTGGTGGTAC GATTTCCGGT AATACGGTAA
4201 ATGTTACGGC AAACGCTGGC GATTTAACAG TTGGGAATGG CGCAGAAATT
4251 AATGCGACAG AAGGAGCTGC AACCTTAACT ACATCATCGG GCAAATTAAC
4301 TACCGAAGCT AGTTCACACA TTACTTCAGC CAAGGGTCAG GTAAATCTTT
4351 CAGCTCAGGA TGGTAGCGTT GCAGGAAGTA TTAATGCCGC CAATGTGACA
4401 CTAAATACTA CAGGCACTTT AACTACCGTG AAGGGTTCAA ACATTAATGC
4451 AACCAGCGGT ACCTTGGTTA TTAACGCAAA AGACGCTGAG CTAAATGGCG
4501 CAGCATTGGG TAACCACACA GTGGTAAATG CAACCAACGC AAATGGCTCC
4551 GGCAGCGTAA TCGCGACAAC CTCAAGCAGA GTGAACATCA CTGGGGATTT
4601 AATCACAATA AATGGATTAA ATATCATTTC AAAAAACGGT ATAAACACCG
4651 TACTGTTAAA AGGCGTTAAA ATTGATGTGA AATACATTCA ACCGGGTATA
4701 GCAAGCGTAG ATGAAGTAAT TGAAGCGAAA CGCATCCCTG AGAAGGTAAA
4751 AGATTTATCT GATGAAGAAA GAGAAGCGTT AGCTAAACTT GGAGTAAGTG
4801 CTGTACGTTT TATTGAGCCA AATAATACAA TTACAGTCGA TACACAAAAT
```

FIG. 1G.

```
4851  GAATTGCAA  CCAGACCATT  AAGTCGAATA  GTGATTTCTG  AAGGCAGGGC
4901  GTGTTCTCA  AACAGTGATG  GCGCGACGGT  GTGCCGTTAAT ATCGCTGATA
4951  ACGGGCGGTA  GCGGTCAGTA  ATTGACAAGG  TAGATTTCAT  CCTGCAATGA
5001  AGTCATTTTA  TTTTCGTATT  ATTTACTGTG  TGGGTTAAAG  TTCAGTACGG
5051  GCTTTACCCA  TCTTGTAAAA  AATTACGGAG  AATACAATAA  AGTATTTTTA
5101  ACAGGTTATT  ATTATG
```

FIG. 2A. AMINO ACID SEQUENCE OF HIGH MOLECULAR WEIGHT PROTEIN I

```
  1  MNKIYRLKFS  KRLNALVAVS  ELARGCDHST  EKGSEKPARM  KVRHLALKPL
 51  SAMLLSLGVT  SIPQSVLASG  LQGMDVVHGT  ATMQVDGNKT  IIRNSVDAII
101  NWKQFNIDQN  EMVQFLQENN  NSAVFNRVTS  NQISQLKGIL  DSNGQVFLIN
151  PNGITIGKDA  IINTNGFTAS  TLDISNENIK  ARNFTFEQTK  DKALAEIVNH
201  GLITVGKDGS  VNLIGGKVKN  EGVISVNGGS  ISLLAGQKIT  ISDIINPTIT
251  YSIAAPENEA  VNLGDIFAKG  GNINVRAATI  RNQGKLSADS  VSKDKSGNIV
301  LSAKEGEAEI  GGVISAQNQQ  AKGGKLMITG  DKVTLKTGAV  IDLSGKEGGE
351  TYLGGDERGE  GKNGIQLAKK  TSLEKGSTIN  VSGKEKGGRA  IVWGDIALID
401  GNINAQGSGD  IAKTGGFVET  SGHDLFIKDN  AIVDAKEWLL  DFDNVSINAE
451  TAGRSNTSED  DEYTGSGNSA  STPKRNKEKT  TLTNTTLESI  LKKGTFVNIT
501  ANQRIYVNSS  INLSNGSLTL  WSEGRSGGGV  EINNDITTGD  DTRGANLTIY
551  SGGWVDVHKN  ISLGAQGNIN  ITAKQDIAFE  KGSNQVITGQ  GTITSGNQKG
601  FRFNNVSLNG  TGSGLQFTTK  RTNKYAITNK  FEGTLNISGK  VNISMVLPKN
651  ESGYDKFKGR  TYWNLTSLNV  SESGEFNLTI  DSRGSDSAGT  LTQPYNLNGI
701  SFNKDTTFNV  ERNARVNFDI  KAPIGINKYS  SLNYASFNGN  ISVSGGGSVD
```

FIG. 2B.

```
 751  FTLLASSSNV  QTPGVVINSK  YFNVSTGSSL  RFKTSGSTKT  GFSIEKDLTL
 801  NATGGNITLL  QVEGTDGMIG  KGIVAKKNIT  FEGGNITFGS  RKAVTEIEGN
 851  VTINNNANVT  LIGSDFDNHQ  KPLTIKKDVI  INSGNLTAGG  NIVNIAGNLT
 901  VESNANFKAI  TNFTFNVGGL  FDNKGNSNIS  IAKGGARFKD  IDNSKNLSIT
 951  TNSSSTYRTI  ISGNITNKNG  DLNITNEGSD  TEMQIGGDVS  QKEGNLTISS
1001  DKINITKQIT  IKAGVDGENS  DSDATNNANL  TIKTKELKLT  QDLNISGFNK
1051  AEITAKDGSD  LTIGNTNSAD  GTNAKKVTFN  QVKDSKISAD  GHKVTLHSKV
1101  ETSGSNNNTE  DSSDNNAGLT  IDAKNVTVNN  NITSHKAVSI  SATSGEITTK
1151  TGTTINATTG  NVEITAQTGS  ILGGIESSSG  SVTLTATEGA  LAVSNISGNT
1201  VTVTANSGAL  TTLAGSTIKG  TESVTTSSQS  GDIGGTISGG  TVEVKATESL
1251  TTQSNSKIKA  TTGEANVTSA  TGTIGGTISG  NTVNVTANAG  DLTVGNGAEI
1301  NATEGAATLT  TSSGKLTTEA  SSHITSAKGQ  VNLSAQDGSV  AGSINAANVT
1351  LNTTGTLTTV  KGSNINATSG  TLVINAKDAE  LNGAALGNHT  VVNATNANGS
1401  GSVIATTSSR  VNITGDLITI  NGLNIISKNG  INTVLLKGVK  IDVKYIQPGI
1451  ASVDEVIEAK  RILEKVKDLS  DEEREALAKL  GVSAVRFIEP  NNTITVDTQN
1501  EFATRPLSRI  VISEGRACFS  NSDGATVCVN  IADNGR
```

FIG. 3A. AMINO ACID SEQUENCE OF HIGH MOLECULAR WEIGHT PROTEIN II (HMW2)

```
  1  TAAATATACA AGATAATAAA AATAAATCAA GATTTTTGTG ATGACAAACA
 51  ACAATTACAA CACCTTTTTT GCAGTCTATA TGCAAATATT TTAAAAAAAT
101  AGTATAAATC CGCCATATAA AATGGTATAA TCTTTCATCT TTCATCTTTA
151  ATCTTTCATC TTTCATCTTT CATCTTTCAT CTTTCATCTT TCATCTTTCA
201  TCTTTCATCT TTCATCTTTC ATCTTTCATC TTTCATCTTT CACATGAAAT
251  GATGAACCGA GGGAAGGGAG GGAGGGGCAA GAATGAAGAG GGAGCTGAAC
301  GAACGCAAAT GATAAAGTAA TTTAATTGTT CAACTAACCT TAGGAGAAAA
351  TATGAACAAG ATATATCGTC TCAAATTCAG CAAACGCCTG AATGCTTTGG
401  TTGCTGTGTC TGAATTGGCA CGGGGTTGTG ACCATTCCAC AGAAAAAGGC
451  TTCCGCTATG TTACTATCTT TAGGTGTAAC CACTTAGCGT TAAAGCCACT
501  TTCCGCTATG TTACTATCTT TAGGTGTAAC ATCTATTCCA CAATCTGTTT
551  TAGCAAGCGG CTTACAAGGA ATGGATGTAG TACACGGCAC AGCCACTATG
601  CAAGTAGATG GTAATAAAAC CATTATCCGC AACAGTGTTG ACGCTATCAT
651  TAATTGGAAA CAATTTAACA TCGACCAAAA TGAAATGGTG CAGTTTTTAC
701  AAGAAAACAA CAACTCCGCC GTATTCAACC GTGTTACATC TAACCAAATC
```

FIG. 3B.

```
 751  TCCCAATTAA  AAGGGATTTT  AGATTCTAAC  GGACAAGTCT  TTTTAATCAA
 801  CCCAAATGGT  ATCACAATAG  GTAAAGACGC  AATTATTAAC  ACTAATGGCT
 851  TTACGGCTTC  TACGCTAGAC  ATTTCTAACG  AAAACATCAA  GGCGCGTAAT
 901  TTCACCTTCG  AGCAAACCAA  AGATAAAGCG  CTCGCTGAAA  TTGTGAATCA
 951  CGGTTTAATT  ACTGTCGGTA  AAGACGGCAG  TGTAAATCTT  ATTGGTGGCA
1001  AAGTGAAAAA  CGAGGGTGTG  ATTAGCGTAA  ATGGTGGCAG  CATTTCTTTA
1051  CTCGCAGGGC  AAAAAATCAC  CATCAGCGAT  ATAATAAACC  CAACCATTAC
1101  TTACAGCATT  GCCGCGCCTG  AAAATGAAGC  GGTCAATCTG  GGCGATATTT
1151  TTGCCAAAGG  CGGTAACATT  AATGTCCGTG  CTGCCACTAT  TCGAAACCAA
1201  GGTAAACTTT  CTGCTGATTC  TGTAAGCAAA  GATAAAAGCG  GCAATATTGT
1251  TCTTTCCGCC  AAAGAGGGTG  AAGCGGAAAT  TGGCGGTGTA  ATTTCCGCTC
1301  AAAATCAGCA  AGCTAAAGGC  GGCAAGCTGA  TGATTACAGG  CGATAAAGTC
1351  ACATTAAAAA  CAGGTGCAGT  TATCGACCTT  TCAGGTAAAG  AAGGGGGAGA
1401  AACTTACCTT  GGCGGTGACG  AGCGCGGCGA  AGGTAAAAAC  GGCATTCAAT
1451  TAGCAAAGAA  AACCTCTTTA  GAAAAAGGCT  CAACCATCAA  TGTATCAGGC
1501  AAAGAAAAAG  GCGGACGCGC  TATTGTGTGG  GGCGATATTG  CGTTAATTGA
```

FIG. 3C.

```
1551  CGGCAATATT AACGCTCAAG GTAGTGGTGA TATCGCTAAA ACCGGTGGTT
1601  TTGTGGAGAC ATCGGGGCAT TATTTATCCA TTGACAGCAA TGCAATTGTT
1651  AAAACAAAAG AGTGGTTGCT AGACCCTGAT GATGTAACAA TTGAAGCCGA
1701  AGACCCCCTT CGCAATAATA CCGGTATAAA TGATGAATTC CCAACAGGCA
1751  CCGGTGAAGC AAGCGACCCT AAAAAAAATA GCGAACTCAA AACAACGCTA
1801  ACCAATACAA CTATTTCAAATTATCTGAAA AACGCCTGGA CAATGAATAT
1851  AACGGCATCA AGAAAACTTA CCGTTAATAG CTCAATCAAC ATCGGAAGCA
1901  ACTCCCACTT AATTCTCCAT AGTAAAGGTC AGCGTGGCGG AGGCGTTCAG
1951  ATTGATGGAG ATATTACTTC TAAAGGCGGA AATTTAACCA TTTATTCTGG
2001  CGGATGGGTT GATGTTCATA AAAATATTAC GCTTGATCAG GGTTTTTTAA
2051  ATATTACCGC CGCTTCCGTA GCTTTTGAAG GTGGAAATAA CAAAGCACGC
2101  GACGCGGCAA ATGCTAAAAT TGTCGCCCAG GGCACTGTAA CCATTACAGG
2151  AGAGGGAAAA GATTTCAGGG CTAACAACGT ATCTTTAAAC GGAACGGGTA
2201  AAGGTCTGAA TATCATTTCA TCAGTGAATA ATTTAACCCA CAATCTTAGT
2251  GGCACAATTA ACATATCTGG GAATATAACA ATTAACCAAA CTACGAGAAA
2301  GAACACCTCG TATTGGCAAA CCAGCCATGA TTCGCACTGG AACGTCAGTG
2351  CTCTTAATCT AGAGACAGGC GCAAATTTTA CCTTTATTAA ATACATTTCA
```

FIG.3D.

```
2401 AGCAATAGCA AAGGCTTAAC AACACAGTAT AGAAGCTCTG CAGGGGTGAA
2451 TTTTAACGGC GTAAATGGCA ACATGTCATT CAATCTCAAA GAAGGAGCGA
2501 AAGTTAATTT CAAATTAAAA CCAAACGAGA ACATGAACAC AAGCAAACCT
2551 TTACCAATTC GGTTTTTAGC CAATATCACA GCCACTGGTG GGGCTCTGT
2601 TTTTTTTGAT ATATATGCCA ACCATTCTGG CAGAGGGGCT GAGTTAAAAA
2651 TGAGTGAAAT TAATATCTCT AACGGCGCTA ATTTTACCTT AAATTCCCAT
2701 GTTCGCGGCG ATGACGCTTT TAAAATCAAC TCAGACAGAC CCATAAATGC
2751 AACCAATTCA AATTTCAGCC AATTCAACCT GAAAGATGAT TTTTATGACG
2801 GGTACGCACG CAATGCCATC ACAACATATC CATTCTGGGC
2851 GGTAATGTCA CCCTTGGTGG ACAAAACTCA AGCAGCAGCA TTACGGGGAA
2901 TATTACTATC GAGAAAGCAG CAAATGTTAC GCTAGAAGCC AATAACGCCC
2951 CTAATCAGCA AAACATAAGG GATAGAGTTA TAAAACTTGG CAGCTTGCTC
3001 GTTAATGGGA GTTTAAGTTT AACTGGCGAA AATGCAGATA TTAAAGGCAA
3051 TCTCACTATT TCAGAAAGCG CCACTTTTAA AGGAAAGACT AGAGATACCC
3101 TAAATATCAC CGGCAATTTT ACCAATAATG GCACTGCCGA AATTAATATA
3151 ACACAAGGAG TGGTAAAACT TGGCAATGTT ACCAATGATG GTGATTTAAA
```

FIG. 3E.

```
3201 CATTACCACT CACGCTAAAC GCAACCAAAG AAGCATCATC GGCGGAGATA
3251 TAATCAACAA AAAAGGAAGC TTAAATATTA CAGACAGTAA TAATGATGCT
3301 GAAATCCAAA TTGGCGGCAA TATCTCGCAA AAAGAAGGCA ACCTCACGAT
3351 TTCTTCCGAT AAAATTAATA TCACCAAACA GATAACAATC AAAAAGGGTA
3401 TTGATGGAGA GGACTCTAGT TCAGATGCGA CAAGTAATGC CAACCTAACT
3451 ATTAAAACCA AAGAATTGAA ATTGACAGAA GACCTAAGTA TTTCAGGTTT
3501 CAATAAAGCA GAGATTACAG CCAAAGATGG TAGAGATTTA ACTATTGGCA
3551 ACAGTAATGA CGGTAACAGC GGTGCCGAAG CCAAAACAGT AACTTTTAAC
3601 AATGTTAAAG ATTCAAAAAT CTCTGCTGAC GGTCACAATG TGACACTAAA
3651 TAGCAAAGTG AAAACATCTA GCAGCAATGG CGGACGTGAA AGCAATAGCG
3701 ACAACGATAC CGGCTTAACT ATTACTGCAA AAAATGTAGA AGTAAACAAA
3751 GATATTACTT CTCTCAAAAC AGTAAATATC ACCGCGTCGG AAAAGGTTAC
3801 CACCACAGCA GGCTCGACCA TTAACGCAAC AAATGGCAAA GCAAGTATTA
3851 CAACCAAAAC AGGTGATATC AGCGGTACGA TTTCCGGTAA CACGGTAAGT
3901 GTTAGCGCGA CTGGTGATTT AACCACTAAA TCCGGCTCAA AAATTGAAGC
3951 GAAATCGGGT GAGGCTAATG TAACAAGTGC AACAGGTACA ATTGGCGGTA
```

FIG. 3F.

```
4001 CAATTTCCGG TAATACGGTA AATGTTACGG CAAACGCTGG CGATTTAACA
4051 GTTGGGAATG GCGCAGAAAT TAATGCGACA GAAGGAGCTG CAACCTTAAC
4101 CGCAACAGGG AATACCTTGA CTACTGAAGC CGGTTCTAGC ATCACTTCAA
4151 CTAAGGGTCA GGTAGACCTC TTGGCTCAGA ATGGTAGCAT CGCAGGAAGC
4201 ATTAATGCTG CTAAATGTGAC ATTAAATACT ACAGGCACCT TAACCACCGT
4251 GGCAGGCTCG GATATTAAAG CAACCAGCGG CACCTTGGTT ATTAACGCAA
4301 AAGATGCTAA GCTAAATGGT GATGCATCAG GTGATAGTAC AGAAGTGAAT
4351 GCAGTCAACG CAAGCGGCTC TGGTAGTGTG ACTGCGGCAA CCTCAAGCAG
4401 TGTGAATATC ACTGGGGATT TAAACACAGT AAATGGGTTA AATATCATTT
4451 CGAAAGATGG TAGAAACACT GTGCGCTTAA GAGGCAAGGA AATTGAGGTG
4501 AAATATATCC AGCCAGGTGT AGCAAGTGTA GAAGAAGTAA TTGAAGCGAA
4551 ACGCGTCCTT GAAAAAGTAA AAGATTTATC TGATGAAGAA AGAGAAACAT
4601 TAGCTAAACT TGGTGTAAGT GCTGTACGTT TTGTTGAGCC AAATAATACA
4651 ATTACAGTCA ATACACAAAA TGAATTTACA ACCAGACCGT CAAGTCAAGT
4701 GATAATTTCT GAAGGTAAGG CGTGTTTCTC AAGTGGTAAT GGCGCACGAG
4751 TATGTACCAA TGTTGCTGAC GATGGACAGC CGTAGTCAGT AATTGACAAG
4801 GTAGATTTCA TCCTGCAATG AAGTCATTTT ATTTTCGTAT TATTTACTGT
```

FIG. 3G.

```
4851  GTGGGTAAA  GTTCAGTACG  GGCTTTACCC  ATCTTGTAAA  AAATTACGGA
4901  GAATACAATA  AAGTATTTTT  AACAGGTTAT  TATTATG
```

FIG. 4A. AMINO ACID SEQUENCE OF HIGH MOLECULAR WEIGHT
PROTEIN 2

| | | | | | |
|---|---|---|---|---|---|
| 1 | MNKIYRLKFS | KRLNALVAVS | ELARGCDHST | EKGSEKPARM | KVRHLALKPL |
| 51 | SAMLLSLGVT | SIPQSVLASG | LQGMDVVHGT | ATMQVDGNKT | IIRNSVDAII |
| 101 | NWKQFNIDQN | EMVQFLQENN | NSAVFNRVTS | NQISQLKGIL | DSNGQVFLIN |
| 151 | PNGITIGKDA | IINTNGFTAS | TLDISNENIK | ARNFTFEQTK | DKALAEIVNH |
| 201 | GLITVGKDGS | VNLIGGKVKN | EGVISVNGGS | ISLLAGQKIT | ISDIINPTIT |
| 251 | YSIAAPENEA | VNLGDIFAKG | GNINVRAATI | RNQGKLSADS | VSKDKSGNIV |
| 301 | LSAKEGEAEI | GGVISAQNQQ | AKGGKLMITG | DKVTLKTGAV | IDLSGKEGGE |
| 351 | TYLGGDERGE | GKNGIQLAKK | TSLEKGSTIN | VSGKEKGGRA | IVWGDIALID |
| 401 | GNINAQGSGD | IAKTGGFVET | SGHDLFIKDN | AIVDAKEWLL | DFDNVSINAE |
| 451 | DPLRNNTGIN | DEFPTGTGEA | SDPKKNSELK | TTLTNTTISN | YLKNAWTMNI |
| 501 | TASRKLTVNS | SINIGSNSHL | ILHSKGQRGG | GVQIDGDITS | KGGNLTIYSG |
| 551 | GWVDVHKNIT | LDQGFLNITA | ASVAFEGGNN | KARDAANAKI | VAQGTVTITG |
| 601 | EGKDFRANNV | SLNGTGKGLN | IISSVNNLTH | NLSGTINISG | NITINQTTRK |
| 651 | NTSYWQTSHD | SHWNVSALNL | ETGANFTFIK | YISSNSKGLT | TQYRSSAGVN |
| 701 | FNGVNGNMSF | NLKEGAKVNF | KLKPNENMNT | SKPLPIRFLA | NITATGGGSV |

FIG. 4B.

```
 751  FFDIYANHSG  RGAELKMSEI  NISNGANFTL  NSHVRGDDAF  KINKDLTINA
 801  TNSNFSLRQT  KDDFYDGYAR  NAINSTYNIS  ILGGNVTLGG  QNSSSSITGN
 851  ITIEKAANVT  LEANNAPNQQ  NIRDRVIKLG  SLLVNGSLSL  TGENADIKGN
 901  LTISESATFK  GKTRDTLNIT  GNFTNNGTAE  INITQGVVKL  GNVTNDGDLN
 951  ITTHAKRNQR  SIGGDIINK   KGSLNITDSN  NDAEIQIGGN  ISQKEGNLTI
1001  SSDKINITKQ  ITIKKGIDGE  DSSSDATSNA  NLTIKTKELK  LTEDLSISGF
1051  NKAEITAKDG  RDLTIGNSND  GNSGAEAKTV  TFNNVKDSKI  SADGHNVTLN
1101  SKVKTSSSNG  GRESNSDNDT  GLTTTAKNVE  VNKDITSLKT  VNITASEKVT
1151  TTAGSTINAT  NGKASITTKT  GDISGTISGN  TVSVSATVDL  TTKSGSKIEA
1201  KSGEANVTSA  TGTIGGTISG  NTVNVTANAG  DLTVGNGAEI  NATEGAATLT
1251  ATGNTLTTEA  GSSITSTKGQ  VDLLAQNGSI  AGSINAANVT  LNTTGTLTTV
1301  AGSDIKATSG  TLVINAKDAK  LNGDASGDST  EVNAVNASGS  GSVTAATSSS
1351  VNITGDLNTV  NGLNIISKDG  RNTVRLRGKE  IEVKYIQPGV  ASVEEVIEAK
1401  RVLEKVKDLS  DEERETLAKL  GVSAVRFVEP  NNTITVNTQN  EFTTRPSSQV
1451  IISEGKACFS  SGNGARVCTN  VADDGQP
```

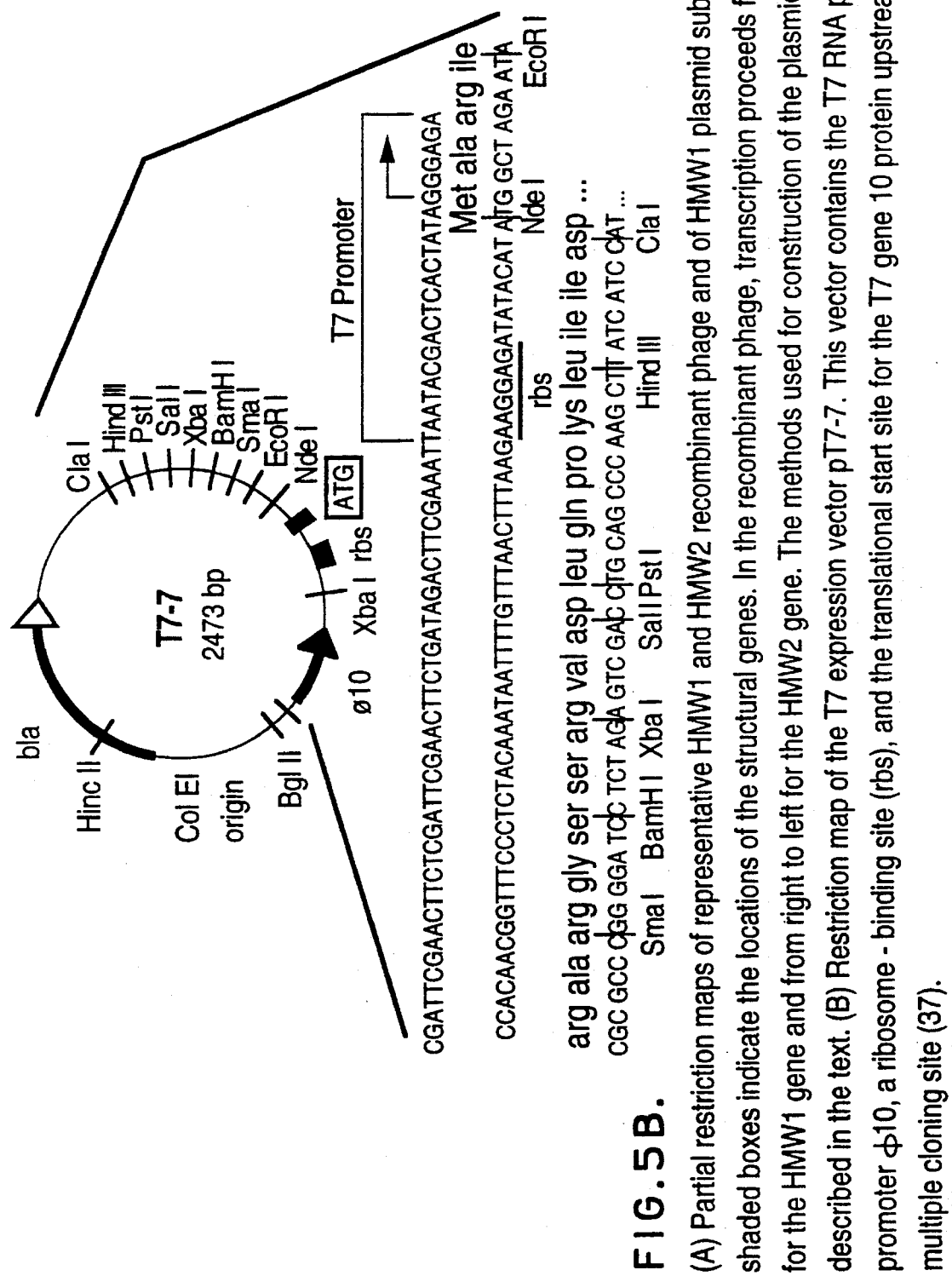

FIG. 5B.

(A) Partial restriction maps of representative HMW1 and HMW2 recombinant phage and of HMW1 plasmid subclones. The shaded boxes indicate the locations of the structural genes. In the recombinant phage, transcription proceeds from left to right for the HMW1 gene and from right to left for the HMW2 gene. The methods used for construction of the plasmids shown are described in the text. (B) Restriction map of the T7 expression vector pT7-7. This vector contains the T7 RNA polymerase promoter φ10, a ribosome-binding site (rbs), and the translational start site for the T7 gene 10 protein upstream from a multiple cloning site (37).

FIG. 6A.

```
  1  ACAGCGTCT  CTTAATACTA  GTACAAACCC  ACAATAAAAT  ATGACAAACA
 51  ACAATTACAA  CACCTTTTTT  GCAGTCTATA  TGCAAATATT  TTAAAAATA
101  GTATAAATCC  GCCATATAAA  ATGGTATAAT  CTTTCATCTT  TCATCTTTCA
151  TCTTTCATCT  TTCATCTTTG  ATCTTTCATC  TTTCATCTTT  CATCTTTCAT
201  CTTTCATCTT  TCATCTTTCA  TCTTTCATCT  TTCATCTTTC  ACATGAAATG
251  ATGAACCGAG  GGAAGGGAGG  GAGGGGCAAG  AATGAAGAGG  GAGCTGAACG
301  AACGCAAATG  ATAAAGTAAT  TTAATTGTTC  AACTAACCTT  AGGAGAAAAT
351  ATGAACAAGA  TATATCGTCT  CAAATTCAGC  AAACGCCTGA  ATGCTTTGGT
401  TGCTGTGTCT  GAATTGGCAC  GGGGTTGTGA  CCATTCCACA  GAAAAGGCA
451  GCGAAAAACC  TGCTCGCATG  AAAGTGCGTC  ACTTAGCGTT  AAAGCCACTT
501  TCCGCTATGT  TACTATCTTT  AGGTGTAACA  TCTATTCCAC  AATCTGTTTT
551  AGCAAGCGGC  TTACAAGGAA  TGGATGTAGT  ACACGGCACA  GCCACTATGC
601  AAGTAGATGG  TAATAAAACC  ATTATCCGCA  ACAGTGTTGA  CGCTATCATT
651  AATTGGAAAC  AATTTAACAT  CGACCAAAAT  GAAATGGTGC  AGTTTTACA
701  AGAAACAAC  AACTCCGCCG  TATTCAACCG  TGTTACATCT  AACCAAATCT
751  CCCAATTAAA  AGGGATTTTA  GATTCTAACG  GACAAGTCTT  TTTAATCAAC
```

FIG. 6B.

```
 801  CCAAATGGTA  TCACAATAGG  TAAAGACGCA  ATTATTAACA  CTAATGGCTT
 851  TACGGCTTCT  ACGCTAGACA  TTTCTAACGA  AAACATCAAG  GCGCGTAATT
 901  TCACCTTCGA  GCAAACCAAA  GATAAAGCGC  TCGCTGAAAT  TGTGAATCAC
 951  GGTTTAATTA  CTGTCGGTAA  AGACGGCAGT  GTAAATCTTA  TTGGTGGCAA
1001  AGTGAAAAAC  GAGGGTGTGA  TTAGCGTAAA  TGGTGGCAGC  ATTTCTTTAC
1051  TCGCAGGGCA  AAAAATCACC  ATCAGCGATA  TAATAAACCC  AACCATTACT
1101  TACAGCATTG  CCCGCCCTGA  AAATGAAGCG  GTCAATCTGG  GCGATATTTT
1151  TGCCAAAGGC  GGTAACATTA  ATGTCCGTGC  TGCCACTATT  CGAAACCAAG
1251  CTTTCCGCCA  AAGAGGGTGA  AGCCGAAATT  GGCGGTGTAA  TTTCCGCTCA
1301  AAATCAGCAA  GCTAAAGCG   GCAAGCTGAT  GATTACAGGC  GATAAAGTCA
1351  CATTAAAAAC  AGGTGCAGTT  ATCGACCTTT  CAGGTAAAGA  AGGGGAGAA
1401  ACTTACCTTG  GCGGTGACGA  GCGCGGCGAA  GGTAAAAACG  GCATTCAATT
1451  AGCAAAGAAA  ACCTCTTTAG  AAAAAGGCTC  AACCATCAAT  GTATCAGGCA
1501  AAGAAAAAGG  CGGACGCGCT  ATTGTGTGGG  GCGATATTGC  GTTAATTGAC
1551  GGCAATATTA  ACGCTCAAGG  TAGTGGTGAT  ATCGCTAAAA  CCGGTGGTTT
1601  TGTGGAGACG  TCGGGGCATG  ATTTATTCAT  CAAAGACAAT  GCAATTGTTG
```

FIG. 6C.

```
1651 ACGCCAAAGA GTGGTTGTTA GACCCGGATA ATGTATCTAT TAATGCAGAA
1701 ACAGCAGGAC GCAGCAATAC TTCAGAAGAC GATGAATACA CGGGATCCGG
1751 GAATAGTGCC AGCACCCCAA AACGAAACAA AGAAAAGACA ACATTAACAA
1801 ACACAACTCT TGAGAGTATA CTAAAAAAAG GTACCTTTGT TAACATCACT
1851 GCTAATCAAC GCATCTATGT CAATAGCTCC ATTAATTTAT CCAATGGCAG
1901 CTTAACTCTT TGGAGTGAGG GTCGGAGCGG TGGCGGCGTT GAGATTAACA
1951 ACGATATTAC CACCGGTGAT GATACCAGAG GTGCAAACTT AACAATTTAC
2001 TCAGGCGGCT GGGTTGATGT TCATAAAAAT ATCTCACTCG GGGCGCAAGG
2051 TAACATAAAC ATTACAGCTA AACAAGATAT CGCCTTTGAG AAAGGAAGCA
2101 ACCAAGTCAT TACAGGTCAA GGGACTATTA CCTCAGGCAA TCAAAAAGGT
2151 TTTAGATTTA ATAATGTCTC TCTAAACGGC ACTGGCAGCG GACTGCAATT
2201 CACCACTAAA AGAACCAATA AATACGCTAT CACAAATAAA TTTGAAGGGA
2251 CTTTAAATAT TTCAGGGAAA GTGAACATCT CAATGGTTTT ACCTAAAAAT
2301 GAAAGTGGAT ATGATAAATT CAAAGGACGC ACTTACTGGA ATTTAACCTC
2351 GAAAGTGGAT ATGATAAATT CAAAGGACGC CCTCACTATT GACTCCAGAG
2401 GAAGCGATAG TGCAGGCACA CTTACCCAGC CTTATAATTT AAACGGTATA
2451 TCATTCAACA AAGACACTAC CTTTAATGTT GAACGAAATG CAAGAGTCAA
```

FIG. 6D.

```
2501  CTTGACATC AAGGCACCAA TAGGGATAAA TAAGTATTCT AGTTTGAATT
2551  ACGCATCATT TAATGGAAAC ATTTCAGTTT CGGGAGGGGG GAGTGTTGAT
2601  TTCACACTTC TCGCCTCATC CTCTAACGTC CAAACCCCCG GTGTAGTTAT
2651  AAATTCTAAA TACTTTAATG TTTCAACAGG GTCAAGTTTA AGATTAAAAA
2701  CTTCAGGCTC AACAAAAACT GGCTTCTCAA TAGAGAAAGA TTTAACTTTA
2751  AATGCCACCG GAGGCAACAT AACACTTTTG CAAGTTGAAG GCACCGATGG
2801  AATGATTGGT AAAGGCATTG TAGCCAAAAA AAACATAACC TTTGAAGGAG
2851  GTAAGATGAG GTTTGGCTCC AGGAAAGCCG TAACAGAAAT CGAAGGCAAT
2901  GTTACTATCA ATAACAACGC TAACGTCACT CTTATCGGTT CGGATTTTGA
2951  CAACCATCAA AAACCTTTAA CTATTAAAAA AGATGTCATC ATTAATAGCG
3001  GCAACCTTAC CGCTGGAGGC AATATTGTCA ATATAGCCGG AAATCTTACC
3051  GTTGAAAGTA ACGCTAATTT CAAAGCTATC ACAAATTTCA CTTTTAATGT
3101  AGGCGGCTTG TTTGACAACA AAGGCAATTC AAATATTTCC ATTGCCAAAG
3151  GAGGGGCTCG CTTTAAAGAC ATTGATAATT CCAAGAATTT AAGCATCACC
3201  ACCAACTCCA GCTCCACTTA CCGCACTATT ATAAGCGGCA ATATAACCAA
3251  TAAAAACGGT GATTTAAATA TTACGAACGA AGGTAGTGAT ACTGAAATGC
```

FIG. 6E.

```
3301  AAATTGGCGG CGATGTCTCG CAAAAGAAG  GTAATCTCAC GATTTCTTCT
3351  GACAAAATCA ATATTACCAA ACAGATAACA ATCAAGGCAG GTGTTGATGG
3401  GGAGAATTCC GATTCAGACG CGACAAACAA TGCCAATCTA ACCATTAAAA
3451  CCAAAGAATT GAAATTAACG CAAGACCTAA ATATTTCAGG TTTCAATAAA
3501  GCAGAGATTA CAGCTAAAGA TGGTAGTGAT TTAACTATTG GTAACACCAA
3551  TAGTGCTGAT GGTACTAATG CCAAAAAAGT AACCTTTAAC CAGGTTAAAG
3601  ATTCAAAAAT CTCTGCTGAC GGTCACAAGG TGACACTACA CAGCAAAGTG
3651  GAAACATCCG GTAGTAATAA CAACACTGAA GATAGCAGTG ACAATAATGC
3701  CGGCTTAACT ATCGATGCAA AAAATGTAAC AGTAAACAAC AATATTACTT
3751  CTCACAAAGC AGTGAGCATC TCTGCGACAA GTGGAGAAAT TACCACTAAA
3801  ACAGGTACAA CCATTAACGC AACCACTGGT AACGTGGAGA TAACCGCTCA
3851  AACAGGTAGT ATCCTAGGTG GAATTGAGTC CAGCTCTGGC TCTGTAACAC
3901  TTACTGCAAC CGAGGGCGCT CTTGCTGTAA GCAATATTTC GGGCAACACC
3951  GTTACTGTTA CTGCAAATAG CGGTGCATTA ACCACTTTGG CAGGCTCTAC
4001  AATTAAAGGA ACCGAGAGTG TAACCACTTC AAGTCAATCA GGCGATATCG
4051  GCGGTACGAT TTCTGGTGGC ACAGTAGAGG TTAAAGCAAC CGAAAGTTTA
```

FIG. 6F.

```
4101  ACCACTCAAT CCAATTCAAA AATTAAAGCA ACAACAGGCG AGGCTAACGT
4151  AACAAGTGCA ACAGGTACAA TTGGTGGTAC GATTTCCGGT AATACGGTAA
4201  ATGTTACGGC AAACGCTGGC GATTTAACAG TTGGGAATGG CGCAGAAATT
4251  AATGCGACAG AAGGAGCTGC AACCTTAACT ACATCATCGG GCAAATTAAC
4301  TACCGAAGCT AGTTCACACA TTACTTCAGC CAAGGGTCAG GTAAATCTTT
4351  CAGCTCAGGA TGGTAGCGTT GCAGGAAGTA TTAATGCCGC CAATGTGACA
4401  CTAAATACTA CAGGCACTTT AACTACCGTG AAGGGTTCAA ACATTAATGC
4451  AACCAGCGGT ACCTTGGTTA TTAACGCAAA AGACGCTGAG CTAAATGGCG
4501  CAGCATTGGG TAACCACACA GTGGTAAATG CAACCAACGC AAATGGCTCC
4551  GGCAGCGTAA TCGCGACAAC CTCAAGCAGA GTGAACATCA CTGGGGATTT
4601  AATCACAATA AATGGATTAA ATATCATTTC AAAAAACGGT ATAAACACCG
4651  TACTGTTAAA AGGCGTTAAA ATTGATGTGA AATACATTCA ACCGGGTATA
4701  GCAAGCGTAG ATGAAGTAAT TGAAGCGAAA CGCATCCTTG AGAAGGTAAA
4751  AGATTTATCT GATGAAGAAA GAGAAGCGTT AGCTAAACTT GGCGTAAGTG
4801  CTGTACGTTT TATTGAGCCA AATAATACAA TTACAGTCGA TACACAAAT
4851  GAATTTGCAA CCAGACCATT AAGTCGAATA GTGATTTCTG AAGGCAGGGC
4901  GTGTTTCTCA AACAGTGATG GCGCGACGGT GTGCGTTAAT ATCGCTGATA
```

FIG. 6G.

```
4951  ACGGGCGGTA GCGGTCAGTA ATTGACAAGG TAGATTTCAT CCTGCAATGA
5001  AGTCATTTTA TTTTCGTATT ATTTACTGTG TGGGTTAAAG TTCAGTACGG
5051  GCTTTACCCA TCTTGTAAAA AATTACGGAG AATACAATAA AGTATTTTTA
5101  ACAGGTTATT ATTATGAAAA ATATAAAAAG CAGATTAAAA CTCAGTGCAA
5151  TATCAGTATT GCTTGGCCTG GCTTCTTCAT CATTGTATGC AGAAGAAGCG
5201  TTTTTAGTAA AAGGCTTTCA GTTATCTGGT GCACTTGAAA CTTTAAGTGA
5251  AGACGCCCAA CTGTCTGTAG CAAAATCTTT ATCTAAATAC CAAGGCTCGC
5301  AAACTTAAAC ACAGCACAGC TTGAATTACA GGCTGTGCTA
5351  GATAAGATTG AGCCAAATAA GTTTGATGTG ATATTGCCAC AACAAACCAT
5401  TACGGATGGC AATATTATGT TTGAGCTAGT CTCGAAATCA GCCGCAGAAA
5451  GCCAAGTTTT TTATAAGGCG AGCCAGGGTT ATAGTGAAGA AAATATCGCT
5501  CGTAGCCTGC CATCTTTGAA ACAAGGAAAA GTGTATGAAG ATGGTCGTCA
5551  GTGGTTCGAT TTGCGTGAAT TCAATATGGC AAAAGAAAAT CCACTTAAAG
5601  TCACTCGCGT GCATTACGAG TTAAACCCTA AAAACAAAAC CTCTGATTTG
5651  GTAGTTGCAG GTTTTCGCC TTTTGGCAAA ACGCGTAGCT TTGTTTCCTA
5701  TGATAATTTC GGGCAAGGG AGTTTAACTA TCAACGTGTA AGTCTAGGTT
```

FIG. 6H.

```
5751  TTGTAAATGC  CAATTGACC  GGACATGATG  ATGTATTAAA  TCTAAACGCA
5801  TTGACCAATG  TAAAAGCACC  ATCAAAATCT  TATGCGGTAG  GCATAGGATA
5851  TACTTATCCG  TTTTATGATA  AACACCAATC  CTTAAGTCTT  TATACCAGCA
5901  TGAGTTATGC  TGATTCTAAT  GATATCGACG  GCTTACCAAG  TGCGATTAAT
5951  CGTAAATTAT  CAAAAGGTCA  ATCTATCTCT  GCGAATCTGA  AATGGAGTTA
6001  TTATCTCCCG  ACATTAACC   TTGGAATGGA  AGACCAGTTT  AAAATTAATT
6051  TAGGCTACAA  CTACCGCCAT  ATTAATCAAA  CATCCGAGTT  AAACACCCTG
6101  GGTGCAACGA  AGAAAAAATT  TGCAGTATCA  GGCGTAAGTG  CAGGCATTGA
6151  TGGACATATC  CAATTTACCC  CTAAAACAAT  CTTTAATATT  GATTAACTC
6201  ATCATTATTA  CGCGAGTAAA  TTACCAGGCT  CTTTTGGAAT  GGAGCGCATT
6251  GGCGAAACAT  TTAATCGCAG  CTATCACATT  AGCACAGCCA  GTTAGGGTT
6301  GAGTCAAGAG  TTTGCTCAAG  GTTGGCATTT  TAGCAGTCAA  TTATCGGGTC
6351  AGTTACTCT   ACAAGATATA  AGTAGCATAG  ATTTATTCTC  TGTAACAGGT
6401  ACTTATGGCG  TCAGAGGCTT  TAAATACGGC  GGTGCAAGTG  GTGAGCGCGG
6451  TCTTGTATGG  CGTAATGAAT  TAAGTATGCC  AAAATACACC  CGCTTTCAAA
6501  TCAGCCCTTA  TGCGTTTTAT  GATGCAGGTC  AGTTCCGTTA  TAATAGCGAA
6551  AATGCTAAAA  CTTACGGCGA  AGATATGCAC  ACGGTATCCT  CTGCGGGTTT
```

FIG.6I.

```
6601  AGGCATTAAA ACCTCTCCTA CACAAAACTT AAGCTTAGAT GCTTTGTTG
6651  CTCGTCGCTT TGCAAATGCC AATAGTGACA ATTTGAATGG CAACAAAAA
6701  CGCACAAGCT CACCTACAAC CTTCTGGGGT AGATTAACAT TCAGTTTCTA
6751  ACCCTGAAAT TTAATCAACT GGTAAGCGTT CCGCCTACCA GTTTATAACT
6801  ATATGCTTTA CCCGCCAATT TACAGTCTAT ACGCAACCCT GTTTTCATCC
6851  TTATATATCA AACAAACTAA GCAAACCAAG CAAACCAAGC AAACCAAGCA
6901  AACCAAGCAA ACCAAGCAAA CCAAGCAAAC CAAGCAAACC AAGCAAACCA
6951  AGCAAACCAA GCAAACCAAG CAAACCAAGC AAACCAAGCA ATGCTAAAAA
7001  ACAATTTATA TGATAAACTA AAACATACTC CATACCATGG CAATACAAGG
7051  GATTTAATAA TATGACAAAA GAAAATTTAC AAAGTGTTCC ACAAAATACG
7101  ACCGCTTCAC TTGTAGAATC AAACAACGAC CAAACTTCCC TGCAAATACT
7151  TAAACAACCA CCCAAACCCA ACCTATTACG CCTGGAACAA CATGTCGCCA
7201  AAAAGATTA TGAGCTTGCT TGCCCGGAAT TAATGGGCGAT TTTGGAAAAA
7251  ATGGACGCTA ATTTTGGAGG CGTTCACGAT ATTGAATTTG ACGCACCTGC
7301  TCAGCTGGCA TATCTACCCG AAAAACTACT AATTCATTTT GCCACTCGTC
7351  TCGCTAATGC AATTACAACA CTCTTTTCCG ACCCCGAATT GGCAATTTCC
```

FIG. 6J.

```
7401 GAAGAAGGGG CATTAAAGAT GATTAGCCTG CAACGCTGGT TGACGCTGAT
7451 TTTGCCTCT TCCCCCTACG TTAACGCAGA CCATATTCTC AATAAATATA
7501 ATATCAACCC AGATTCCGAA GGTGGCTTTC ATTTAGCAAC AGACAACTCT
7551 TCTATTGCTA AATTCTGTAT TTTTACTTA CCCGAATCCA ATGTCAATAT
7601 GAGTTTAGAT GCGTTATGGG CAGGGAATCA ACAACTTTGT GCTTCATTGT
7651 GTTTGCGTT GCAGTCTTCA CGTTTTATTG GTACTGCATC TGCGTTTCAT
7701 AAAAGAGCGG TGGTTTTACA GTGGTTTCCT AAAAAACTCG CCGAAATTGC
7751 TAATTTAGAT GAATTGCCTG CAAATATCCT TCATGATGTA TATATGCACT
7801 GCAGTTATGA TTTAGCAAAA AACAAGCACG ATGTTAAGCG TCCATTAAAC
7851 GAACTTGTCC GCAAGCATAT CCTCACGCAA GGATGGCAAG ACCGCTACCT
7901 TTACACCTTA GGTAAAAAGG ACGGCAAACC TGTGATGATG GTACTGCTTG
7951 AACATTTAA TTCGGGACAT TCGATTTATC GCACGCATTC AACTTCAATG
8001 ATTGCTGCTC GAGAAAAATT CTATTAGTC GGCTTAGGCC ATGAGGGCGT
8051 TGATAACATA GGTCGAGAAG TGTTTGACGA GTTCTTTGAA ATCAGTAGCA
8101 ATAATATAAT GGAGAGACTG TTTTTATCC GTAAACAGTG CGAAACTTTC
8151 CAACCCGCAG TGTTCTATAT GCCAAGCATT GGCATGGATA TTACCACGAT
```

FIG. 6K.

```
8201 TTTGTGAGC AACACTCGGC TTGCCCCTAT TCAAGCTGTA GCCTTGGGTC
8251 ATCCTGCCAC TACGCATTCT GAATTATTG  ATTATGTCAT CGTAGAAGAT
8301 GATTATGTGG GCAGTGAAGA TTGTTTAGC  GAAACCCTTT TACGCTTACC
8351 CAAAGATGCC CTACCTTATG TACCATCTGC ACTCGCCCCA CAAAAAGTGG
8401 ATTATGTACT CAGGGAAAAC CCTGAAGTAG TCAATATCGG TATTGCCGCT
8451 ACCACAATGA AATTAAACCC TGAATTTTTG CTAACATTGC AAGAAATCAG
8501 AGATAAAGCT AAAGTCAAAA TACATTTTCA TTTCGCACTT GGACAATCAA
8551 CAGGCTTGAC ACACCCTTAT GTCAAATGGT TTATCGAAAG CTATTTAGGT
8601 GACGATGCCA CTGCACATCC CCACGCACCT TATCACGATT ATCTGGCAAT
8651 ATTGCGTGAT TGCGATATGC TACTAAATCC GTTTCCTTTC GGTAATACTA
8701 ACGGCATAAT TGATATGGTT ACATTAGGTT TAGTTGGTGT ATGCAAAACG
8751 GGGGATGAAG TACATGAACA TATTGATGAA GGTCTGTTTA AACGCTTAGG
8801 ACTACCAGAA TGGCTGATAG CCGACACACG AGAAACATAT ATTGAATGTG
8851 CTTTGCGTCT AGCAGAAAAC CATCAAGAAC GCCTTGAACT CCGTCGTTAC
8901 ATCATAGAAA ACAACGGCTT ACAAAAGCTT TTTACAGGCG ACCCTCGTCC
8951 ATTGGGCAAA ATACTGCTTA AGAAAACAAA TGAATGGAAG CGGAAGCACT
9001 TGAGTAAAAA ATAACGGTTT TTTAAAGTAA AAGTGCGGTT AATTTTCAAA
```

FIG. 6L.

```
9051  GCGTTTTAAA  AACCTCTCAA  AAATCAACCG  CACTTTTATC  TTTATAACGC
9101  TCCCGCGCGC  TGACAGTTTA  TCTCTTTCTT  AAAATACCCA  TAAAATTGTG
9151  GCAATAGTTG  GGTAATCAAA  TTCAATTGTT  GATACGGCAA  ACTAAAGACG
9201  GCGCGTTCTT  CGGCAGTCAT  C
```

FIG. 7A.

```
  1  CGCCACTTCA ATTTTGGATT GTTGAAATTC AACTAACCAA AAAGTGCGGT
 51  TAAAATCTGT GGAGAAAATA GGTTGTAGTG AAGAACGAGG TAATTGTTCA
101  AAAGGATAAA GCTCTCTTAA TTGGGCATTG GTTGGCGTTT CTTTTTCGGT
151  TAATAGTAAA TTATATTCTG GACGACTATG CAATCCACCA ACAACTTTAC
201  CGTTGGTTTT AAGCGTTAAT GTAAGTTCTT GCTCTTCTTG GCGAATACGT
251  AATCCCATTT TTTGTTTAGC AAGAAAAATGA TCGGGATAAT CATAATAGGT
301  GTTGCCCAAA AATAAATTTT GATGTTCTAA AATCATAAAT TTTGCAAGAT
351  ATTGTGGCAA TTCAATACCT ATTTGTGGCG AAATCGCCAA TTTTAATTCA
401  ATTTCTTGTA GCATAATATT TCCCACTCAA ATCAACTGGT TAAATATACA
451  AGATAATAAA AATAAATCAA GATTTTTGTG ATGACAAACA ACAATTACAA
501  CACCTTTTTT GCAGTCTATA TGCAAATATT TTAAAAAAT AGTATAAATC
551  CGCCATATAA AATGGTATAA TCTTTCATCT TTCATCTTTC ATCTTTCATC
601  TTTCATCTTT CATCTTTCAT CTTTCATCTT TCATCTTTCA TCTTTCATCT
651  TTCATCTTTC ATCTTTCATC TTTCATCTTT CACATGAAAT GATGAACCGA
701  GGGAAGGGAG GGAGGGGCAA GAATGAAGAG GGAGCTGAAC GAACGCAAAT
751  GATAAAGTAA TTTAATTGTT CAACTAACCT TAGGAGAAAA TATGAACAAG
```

FIG. 7B.

```
801   ATATATCGTC  TCAAATTCAG  CAAACGCCTG  AATGCTTTGG  TTGCTGTGTC
851   TGAATTGGCA  CGGGGTTGTG  ACCATTCCAC  AGAAAAAGGC  AGCGAAAAAC
901   CTGCTCGCAT  GAAAGTGCGT  CACTTAGCGT  TAAAGCCACT  TTCCGCTATG
951   TTACTATCTT  TAGGTGTAAC  ATCTATTCCA  CAATCTGTTT  TAGCAAGCGG
1001  CAATTTAACA  TCGACCAAAA  TGAAATGGTG  CAGTTTTTAC  AAGAAAACAA
1051  GTAATAAAAC  CATTATCCGC  AACAGTGTTG  ACGCTATCAT  TAATTGGAAA
1101  CAATTTAACA  TCGACCAAAA  TGAAATGGTG  CAGTTTTTAC  AAGAAAACAA
1151  CAACTCCGCC  GTATTCAACC  GTGTTACATC  TAACCAAATC  TCCCAATTAA
1201  AAGGGATTTT  AGATTCTAAC  GGACAAGTCT  TTTTAATCAA  CCCAAATGGT
1251  ATCACAATAG  GTAAAGACGC  AATTATTAAC  ACTAATGGCT  TTACGCTTC
1301  TACGCTAGAC  ATTTCTAACG  AAAACATCAA  GGCGCGTAAT  TTCACCTTCG
1351  AGCAAACCAA  AGATAAAGCG  CTCGCTGAAA  TTGTGAATCA  CGGTTTAATT
1401  ACTGTCGGTA  AAGACGGCAG  TGTAAATCTT  ATTGGTGGCA  AAGTGAAAAA
1451  CGAGGGTGTG  ATTAGCGTAA  ATGGTGGCAG  CATTTCTTTA  CTCGCAGGGC
1501  AAAAAATCAC  CATCAGCGAT  ATAATAAACC  CAACCATTAC  TTACAGCATT
1551  GCCGGCCTG   AAAATGAAGC  GGTCAATCTG  GGCGATATTT  TTGCCAAAGG
```

FIG. 7C.

```
1601 CGGTAACATT AATGTCCGTG CTGCCACTAT TCGAAACCAA GGTAAACTTT
1651 CTGCTGATTC TGTAAGCAAA GATAAAAGCG GCAATATTGT TCTTTCCGCC
1701 AAAGAGGGTG AAGCGGAAAT TGGCGGTGTA ATTCCGCTC  AAAATCAGCA
1751 AGCTAAAGGC GGCAAGCTGA TGATTACAGG CGATAAAGTC ACATTAAAAA
1801 CAGGTGCAGT TATCGACCTT TCAGGTAAAG AAGGGGGAGA AACTTACCTT
1851 GGCGGTGACG AGCGCGGGCA AGGTAAAAAC GGCATTCAAT TAGCAAAGAA
1901 AACCTCTTTA GAAAAAGGCT CAACCATCAA TGTATCAGGC AAAGAAAAAG
1951 GCGGACGCGC TATTGTGTGG GGCGATATTG CGTTAATTGA CGGCAATATT
2001 AACGCTCAAG GTAGTGGTGA TATCGCTAAA ACCGGTGGTT TTGTGGAGAC
2051 ATCGGGGCAT TATTTATCCA TTGACAGCAA TGCAATTGTT AAAACAAAAG
2101 AGTGGTTGCT AGACCCTGAT GATGTAACAA TTGAAGCCGA AGACCCCCTT
2151 CGCAATAATA CCGGTATAAA TGATGAATTC CCAACAGGCA CCGGTGAAGC
2201 AAGCGACCCT AAAAAAAATA GCGAACTCAA AACAACGCTA ACCAATACAA
2251 CTATTTCAAA TTATCTGAAA AACGCCTGGA CAATGAATAT AACGGCATCA
2301 AGAAAACTTA CCGTTAATAG CTCAATCAAC ATCGGAAGCA ACTCCCACTT
2351 AATTCTCCAT AGTAAAGGTC AGCGTGGCCG AGCCGTTCAG ATTGATGGAG
2401 ATATTACTTC TAAAGGCGGA AATTTAACCA TTTATTCTGG CGGATGGGTT
```

FIG. 7D.

```
2451  GATGTTCATA  AAATATTAC   GCTTGATCAG  GGTTTTTTAA  ATATTACCGC
2501  CGCTTCCGTA  GCTTTTGAAG  GTGGAAATAA  CAAAGCACGC  GACGCGGCAA
2551  ATGCTAAAAT  TGTCGCCCAG  GGCACTGTAA  CCATTACAGG  AGAGGAAAA
2601  GATTTCAGGG  CTAACAACGT  ATCTTTAAAC  GGAACGGGTA  AAGGTCTGAA
2651  TATCATTTCA  TCAGTGAATA  ATTTAACCCA  CAATCTTAGT  GGCACAATTA
2701  ACATATCTGG  GAATATAACA  ATTAACCAAA  CTACGAGAAA  GAACACCTCG
2751  TATTGGCAAA  CCAGCCATGA  TTCGCACTGG  AACGTCAGTG  CTCTTAATCT
2801  AGAGACAGGC  GCAAATTTTA  CCTTTATTAA  ATACATTTCA  AGCAATAGCA
2851  AAGGCTTAAC  AACACAGTAT  AGAAGCTCTG  CAGGGGTGAA  TTTAACGGC
2901  GTAAATGGCA  ACATGTCATT  CAATCTCAAA  GAAGGAGCGA  AAGTTAATTT
2951  CAAATTAAAA  CCAAACGAGA  ACATGAACAC  AAGCAAACCT  TTACCAATTC
3001  GGTTTTTAGC  CAATATCACA  GCCACTGGTG  GGGCTCTGT   TTTTTTTGAT
3051  ATATATGCCA  ACCATTCTGG  CAGAGGGGCT  GAGTTAAAAA  TGAGTGAAAT
3101  TAATATCTCT  AACGGCGCTA  ATTTTACCTT  AAATTCCCAT  GTTCGCGGCG
3151  ATGACGCTTT  TAAAATCAAC  AAAGACTTAA  CCATAAATGC  AACCAATTCA
3201  AATTTCAGCC  TCAGACAGAC  GAAAGATGAT  TTTATGACG   GGTACGCACG
```

FIG. 7E.

| | | | |
|---|---|---|---|
| 3251 | CAATGCCATC | AATTCAACCT | ACAACATATC | CATTCTGGGC | GGTAATGTCA |
| 3301 | CCCTTGGTGG | ACAAAACTCA | AGCAGCAGCA | TTACGGGGAA | TATTACTATC |
| 3351 | GAGAAAGCAG | CAAATGTTAC | GCTAGAAGCC | AATAACGCCC | CTAATCAGCA |
| 3401 | AAACATAAGG | GATAGAGTTA | TAAAACTTGG | CAGCTTGCTC | GTTAATGGGA |
| 3451 | GTTTAAGTTT | AACTGCGAA | AATGCAGATA | TTAAAGGCAA | TCTCACTATT |
| 3501 | TCAGAAAGCG | CCACTTTTAA | AGGAAAGACT | AGAGATACCC | TAAATATCAC |
| 3551 | CGGCAATTTT | ACCAATAATG | GCACTGCCGA | AATTAATATA | ACACAAGGAG |
| 3601 | TGGTAAAACT | TGGCAATGTT | ACCAATGATG | GTGATTTAAA | CATTACCACT |
| 3651 | CACGCTAAAC | GCAACCAAAG | AAGCATCATC | GGCGGAGATA | TAATCAACAA |
| 3701 | AAAAGGAAGC | TTAAATATTA | CAGACAGTAA | TAATGATGCT | GAAATCCAAA |
| 3751 | TTGGCGGCAA | TATCTCGCAA | AAAGAAGGCA | ACCTCACGAT | TTCTTCCGAT |
| 3801 | AAAATTAATA | TCACCAAACA | GATAACAATC | AAAAGGGTA | ATTAAAACCA |
| 3851 | GGACTCTAGT | TCAGATGCGA | CAAGTAATGC | CAACCTAACT | TTGATGGAGA |
| 3901 | AAGAATTGAA | ATTGACAGAA | GACCTAAGTA | TTTCAGGTTT | CAATAAAGCA |
| 3951 | GAGATTACAG | CCAAAGATGG | TAGAGATTTA | ACTATTGGCA | ACAGTAATGA |
| 4001 | CGGTAACAGC | GGTGCCGAAG | CCAAAACAGT | AACTTTTAAC | AATGTTAAAG |

FIG. 7F.

```
4051  ATTCAAAAAT CTCTGCTGAC GGTCACAATG TGACACTAAA TAGCAAAGTG
4101  AAAACATCTA GCAGCAATGG CGGACGTGAA AGCAATAGCG ACAACGATAC
4151  CGGCTTAACT ATTACTGCAA AAAATGTAGA AGTAAACAAA GATATTACTT
4201  CTCTCAAAAC AGTAAATATC ACCGCGTCGG AAAAGGTTAC CACCACAGCA
4251  GGCTCGACCA TTAACGCAAC AAATGGCAAA GCAAGTATTA CAACCAAAAC
4301  AGGTGATATC AGCGGTACGA TTTCCGGTAA CACGGTAAGT GTTAGCGCGA
4351  CTGGTGATTT AACCACTAAA TCCGGCTCAA AAATTGAAGC GAAATCGGGT
4401  GAGGCTAATG TAACAAGTGC AACAGGTACA ATTGGCGGTA CAATTCCGG
4451  TAATACGGTA AATGTTACGG CAAACGCTGG CGATTAACA GTTGGGAATG
4501  GCGCAGAAAT TAATGCGACA GAAGGAGCTG CAACCTTAAC CGCAACAGGG
4551  AATACCTTGA CTACTGAAGC CGGTTCTAGC ATCACTTCAA CTAAGGGTCA
4601  GGTAGACCTC TTGGCTCAGA ATGGTAGCAT CGCAGGAAGC ATTAATGCTG
4651  CTAATGTGAC ATTAAATACT ACAGGCACCT TAACCACCGT GGCAGGCTCG
4701  GATATTAAAG CAACCAGCGG CACCTTGGTT ATTAACGCAA AAGATGCTAA
4751  GCTAAATGGT GATGCATCAG GTGATAGTAC AGAAGTGAAT GCAGTCAACG
4801  ACTGGGGATT TGGTAGTGTG ACTGCGGCAA CCTCAAGCAG TGTGAATATC
4851  ACTGGGGATT TAAACACAGT AAATGGGTTA AATATCATTT CGAAAGATGG
```

FIG. 7G.

```
4901  TAGAAACACT GTGCGCTTAA GAGGCAAGGA AATTGAGGTG AAATATATCC
4951  AGCCAGGTGT AGCAAGTGTA GAAGAAGTAA TTGAAGCGAA ACGGTCCTT
5001  GAAAAAGTAA AAGATTTATC TGATGAAGAA AGAGAAACAT TAGCTAAACT
5051  TGGTGTAAGT GCTGTACGTT TTGTTGAGCC AAATAATACA ATTACAGTCA
5101  ATACACAAAA TGAATTTACA ACCAGACCGT CAAGTCAAGT GATAATTTCT
5151  GAAGGTAAGG CGTGTTTCTC AAGTGGTAAT GGCGCACGAG TATGTACCAA
5201  TGTTGCTGAC GATGGACAGC CGTAGTCAGT AATTGACAAG GTAGATTTCA
5251  TCCTGCAATG AAGTCATTTT ATTTTCGTAT TATTTACTGT GTGGGTTAAA
5301  GTTCAGTACG GGCTTTACCC ATCTTGTAAA AAATTACGGA GAATACAATA
5351  AAGTATTTTT AACAGGTTAT TATTATGAAA AATATAAAAA GCAGATTAAA
5401  ACTCAGTGCA ATATCAGTAT TGCTTGGCCT GGCTTCTTCA TCATTGTATG
5451  CAGAAGAAGC GTTTTAGTA AAAGGCTTTC AGTTATCTGG TGCACTTGAA
5501  ACTTTAAGTG AAGACGCCCA ACTGTCTGTA GCAAAATCTT TATCTAAATA
5551  CCAAGGCTCG CAAACTTTAA CAAACCTAAA AACAGCACAG CTTGAATTAC
5601  AGGCTGTGCT AGATAAGATT GAGCCAAATA AATTTGATGT GATATTGCCG
5651  CAACAAACCA TTACGGATGG CAATATCATG TTTGAGCTAG TCTCGAAATC
```

FIG. 7H.

```
5701  AGCCGCAGAA  AGCCAAGTTT  TTTATAAGGC  GAGCCAGGGT  TATAGTGAAG
5751  AAATATCGC   TCGTAGCCTG  CCATCTTTGA  AACAAGGAAA  AGTGTATGAA
5801  GATGGTCGTC  AGTGGTTCGA  TTTGCGTGAA  TTTAATATGG  CAAAAGAAAA
5851  CCCGCTTAAG  GTTACCCGTG  TACATTACGA  ACTAAACCCT  AAAAACAAAA
5901  CCTCTAATTT  GATAATTGCG  GGCTTCTCGC  CTTTTGGTAA  AACGCGTAGC
5951  TTTATTTCTT  ATGATAATTT  CGGCGCGAGA  GAGTTTAACT  ACCAACGTGT
6001  AAGCTTGGGT  TTTGTTAATG  CCAATTAAC   TGGTCATGAT  GATGTGTTAA
6151  TTATACCAGT  ATGAGTTATG  CTGATTCTAA  TGATATCGAC  GGCTTACCAA
6201  GTGCGATTAA  TCGTAAATTA  TCAAAAGGTC  AATCTATCTC  TGCGAATCTG
6251  AAATGGAGTT  ATTATCTCCC  AACATTAAC   CTTGGCATGG  AAGACCAATT
6301  TAAAATTAAT  TTAGGCTACA  ACTACCGCCA  TATTAATCAA  ACCTCCGCGT
6351  TAAATCGCTT  GGGTGAAACG  AAGAAAAAAT  TTGCAGTATC  AGGCGTAAGT
6401  GCAGGCATTG  ATGGACATAT  CCAATTTACC  CCTAAAAACAA TCTTTAATAT
6451  TGATTTAACT  CATCATTATT  ACGCGAGTAA  ATTACCAGGC  TCTTTTGGAA
6501  TGGAGCGCAT  TGGCGAAACA  TTTAATCGCA  GCTATCACAT  TAGCACAGCC
6551  AGTTTAGGGT  TGAGTCAAGA  GTTTGCTCAA  GGTTGGCATT  TTAGCAGTCA
6601  ATTATCAGGT  CAATTTACTC  TACAAGATAT  TAGCAGTATA  GATTTATTCT
```

FIG.7I.

```
6651  CTGTAACAGG  TACTTATGGC  GTCAGAGGCT  TTAAATACGG  CGGTGCAAGT
6701  GGTGAGCGCG  GTCTTGTATG  GCGTAATGAA  TTAAGTATGC  CAAAATACAC
6751  CCGCTTCCAA  ATCAGCCCTT  ATGCGTTTTA  TGATGCAGGT  CAGTTCCGTT
6801  ATAATAGCGA  AAATGCTAAA  ACTTACGGCG  AAGATATGCA  CACGGTATCC
6851  TCTGCGGGTT  TAGGCATTAA  AACCTCTCCT  ACACAAAACT  TAAGCCTAGA
6901  TGCTTTTGTT  GCTCGTCGCT  TTGCAAATGC  CAATAGTGAC  AATTTGAATG
6951  GCAACAAAAA  ACGCACAAGC  TCACCTACAA  CCTTCTGGGG  GAGATTAACA
7001  TTCAGTTTCT  AACCCTGAAA  TTTAATCAAC  TGGTAAGCGT  TCCGCCTACC
7051  AGTTTATAAC  TATATGCTTT  ACCCGCCAAT  TTACAGTCTA  TAGGCAACCC
7101  TGTTTTTACC  CTTATATATC  AAATAAACAA  GCTAAGCTGA  GCTAAGCAAA
7151  CCAAGCAAAC  TCAAGCAAGC  CAAGTAATAC  TAAAAAACA   ATTTATATGA
7201  TAAACTAAAG  TATACTCCAT  GCCATGGCGA  TACAAGGGAT  TTAATAATAT
7251  GACAAAAGAA  AATTTGCAAA  ACGCTCCTCA  AGATGCGACC  GCTTTACTTG
7301  CGGAATTAAG  CAACAATCAA  ACTCCCCTGC  GAATATTTAA  ACAACCACGC
7351  AAGCCCAGCC  TATTACGCTT  GGAACAACAT  ATCGCAAAAA  AAGATTATGA
7401  GTTTGCTTGT  CGTGAATTAA  TGGTGATTCT  GGAAAAAATG  GACGCTAATT
```

FIG. 7J.

```
7451  TTGGAGGCGT  TCACGATATT  GAATTTGACG  CACCCGCTCA  GCTGGCATAT
7501  CTACCCGAAA  AATTACTAAT  TTATTTTGCC  ACTCGTCTCG  CTAATGCAAT
7551  TACAACACTC  TTTTCCGACC  CCGAATTGGC  AATTTCTGAA  GAAGGGGCGT
7601  TAAAGATGAT  TAGCCTGCAA  CGCTGGTTGA  CGCTGATTTT  TGCCTCTTCC
7651  CCCTACGTTA  ACGCAGACCA  TATTCTCAAT  AAATATAATA  TCAACCCAGA
7701  TTCCGAAGGT  GGCTTTCATT  TAGCAACAGA  CAACTCTTCT  ATTGCTAAAT
7751  TCTGTATTTT  TTACTTACCC  GAATCCAATG  TCAATATGAG  TTTAGATGCG
7801  TTATGGGCAG  GGAATCAACA  ACTTTGTGCT  TCATTGTGTT  TTGCGTTGCA
7851  GTCTTCACGT  TTTATTGGTA  CCGCATCTGC  GTTTCATAAA  AGAGCGGTGG
7901  TTTTACAGTG  GTTTCCTAAA  AAACTCGCCG  AAATTGCTAA  TTTAGATGAA
7951  TTGCCTGCAA  ATATCCTTCA  TGATGTATAT  ATGCACTGCA  GTTATGATTT
8001  AGCAAAAAAC  AAGCACGATG  TTAAGCGTCC  ATTAAACGAA  CTTGTCCGCA
8051  AGCATATCCT  CACGCAAGGA  TGGCAAGACC  GCTACCTTTA  CACCTTAGGT
8101  AAAAGGACG   GCAAACCTGT  GATGATGGTA  CTGCTTGAAC  ATTTAATTC
8151  GGGACATTCG  ATTTATCGTA  CACATTCAAC  TTCAATGATT  GCTGCTCGAG
8201  AAAAATTCTA  TTTAGTCGGC  TTAGGCCATG  AGGGCGTTGA  TAAAATAGGT
```

FIG. 7K.

```
8251  CGAGAAGTGT  TTGACGAGTT  CTTTGAAATC  AGTAGCAATA  ATATAATGGA
8301  GAGACTGTTT  TTTATCCGTA  AACAGTGCGA  AACTTTCCAA  CCCGCAGTGT
8351  TCTATATGCC  AAGCATTGGC  ATGGATATTA  CCACGATTTT  TGTGAGCAAC
8401  ACTCGGCTTG  CCCCTATTCA  AGCTGTAGCC  CTGGGTCATC  CTGCCACTAC
8451  GCATTCTGAA  TTTATTGATT  ATGTCATCGT  AGAAGATGAT  TATGTGGGCA
8501  GTGAAGATTG  TTTCAGCGAA  ACCCTTTTAC  GCTTACCCAA  AGATGCCCTA
8551  CCTTATGTAC  CTTCTGCACT  CGCCCCACAA  AAAGTGGATT  ATGTACTCAG
8601  GGAAACCCT   GAAGTAGTCA  ATATCGGTAT  TGCCGCTACC  ACAATGAAAT
8651  TAAACCCTGA  ATTTTTGCTA  ACATTGCAAG  AAATCAGAGA  TAAAGCTAAA
8701  GTCAAAATAC  ATTTTCATTT  CGCACTTGGA  CAATCAACAG  GCTTGACACA
8751  CCCTTATGTC  AAATGGTTTA  TCGAAAGCTA  TTTAGGTGAC  GATGCCACTG
8801  CACATCCCCA  CGCACCTTAT  CACGATTATC  TGGCAATATT  GCGTGATTGC
8851  GATATGCTAC  TAAATCCGTT  TCCTTTCGGT  AATACTAACG  GCATAATTGA
8901  TATGGTTACA  TTAGGTTTAG  TTGGTGTATG  CAAAACGGGG  GATGAAGTAC
8951  ATGAACATAT  TGATGAAGGT  CTGTTTAAAC  GCTTAGGACT  ACCAGAATGG
9001  CTGATAGCCG  ACACACGAGA  AACATATATT  GAATGTGCTT  TGCGTCTAGC
9051  AGAAAACCAT  CAAGAACGCC  TTGAACTCCG  TCGTTACATC  ATAGAAAACA
```

FIG. 7L.

```
9101 ACGGCTTACA AAAGCTTTTT ACAGGGCGACC CTCGTCCATT GGGCAAAATA
9151 CTGCTTAAGA AAACAAATGA ATGGAAGCGG AAGCACTTGA GTAAAAAATA
9201 ACGGTTTTTT AAAGTAAAAG TGCGGGTTAAT TTTCAAAGCG TTTTAAAAAC
9251 CTCTCAAAAA TCAACCCGCAC TTTTTATCTTT ATAACGATCC CGCACGCTGA
9301 CAGTTTATCA GCCTCCCCGCC ATAAAACTCC GCCTTTCATG GCGGAGATTT
9351 TAGCCAAAAC TGGCAGAAAT TAAAGGCTAA AATCACCAAA TTGCACCACA
9401 AAATCACCAA TACCCACAAA AAA
```

FIG. 8A.

```
  1 GATCAATCTG GGCGATATTT TTGCCAAAGG TGGTAACATT AATGTCCGCG
 51 CTGCCACTAT TCGCAATAAA GGTAAACTTT CTGCCGACTC TGTAAGCAAA
101 GATAAAAGTG GTAACATTGT TCTCTCTGCC AAAGAAGGTG AAGCGGAAAT
151 TGGCGGTGTA ATTTCCGCTC AAAATCAGCA AGCCAAAGGT GGTAAGTTGA
201 TGATTACAGG CGATAAAGTT ACATTGAAAA CGGGTGCAGT TATCGACCTT
251 TCGGGTAAAG AAGGGGGAGA AACTTATCTT GGCGGTGACG AGCGTGGCGA
301 AGGTAAAAAC GGCATTCAAT TAGCAAAGAA AACCACTTTA GAAAAAGGCT
351 CAACAATTAA TGTGTCAGGT AAAGAAAAAG GTGGGCGCGC TATTGTATGG
401 GGCGATATTG CGTTAATTGA CGGCAATATT AATGCCCAAG GTAAAGATAT
451 CGCTAAAACT GGTGGTTTTG TGGAGACGTC GGGGCATTAC TTATCCATTG
501 ATGATAACGC AATTGTTAAA ACAAAAGAAT GGCTACTAGA CCCAGAGAAT
551 GTGACTATTG AAGCTCCTTC CGCTTCTCGC GTCGAGCTGG GTGCCGATAG
601 GAATTCCCAC TCGGCAGAGG TGATAAAAGT GACCCTAAAA AAAAATAACA
651 CCTCCTTGAC AACACTAACC AATACAACCA TTTCAAATCT TCTGAAAAGT
701 GCCCACGTGG TGAACATAAC GGCAAGGAGA AAACTTACCG TTAATAGCTC
751 TATCAGTATA GAAAGAGGCT CCCACTTAAT TCTCCACAGT GAAGGTCAGG
```

FIG. 8B.

```
801   GCGGTCAAGG TGTTCAGATT GATAAAGATA TTACTTCTGA AGGCGGAAAT
851   TTAACCATTT ATTCTGGCGG ATGGGTTGAT GTTCATAAAA ATATTACGCT
901   TGGTAGCGGC TTTTTAAACA TCACAACTAA AGAAGGAGAT ATCGCCTTCG
951   AAGACAAGTC TGGACGGAAC AACCTAACCA TTACAGCCCA AGGGACCATC
1001  ACCTCAGGTA ATAGTAACGG CTTTAGATTT AACAACGTCT CTCTAAACAG
1051  CCTTGGCGGA AAGCTGAGCT TTACTGACAG CAGAGAGGAC AGAGGTAGAA
1101  GAACTAAGGG TAATATCTCA AACAAATTTG ACGGAACGTT AAACATTCC
1151  GGAACTGTAG ATATCTCAAT GAAAGCACCC AAAGTCAGCT GGTTTTACAG
1201  AGACAAAGGA CGCACCTACT GGAACGTAAC CACTTTAAAT GTTACCTCGG
1251  GTAGTAAATT TAACCTCTCC ATTGACAGCA CAGGAAGTGG CTCAACAGGT
1301  CCAAGCATAC GCAATGCAGA ATTAAATGGC ATAACATTTA ATAAAGCCAC
1351  TTTTAATATC GCACAAGGCT CAACAGCTAA CTTTAGCATC AAGGCATCAA
1401  TAATGCCCTT TAAGAGTAAC GCTAACTACG CATTATTTAA TGAAGATATT
1451  TCAGTCTCAG GGGGGGTAG CGTTAATTTC AAACTTAACG CCTCATCTAG
1501  CAACATACAA ACCCCTGGCG TAATTATAAA ATCTCAAAAC TTTAATGTCT
1551  CAGGAGGGTC AACTTAAAT CTCAAGGCTG AAGGTTCAAC AGAAACCGCT
1601  TTTTCAATAG AAAATGATTT AAACTTAAAC GCCACCGGTG GCAATATAAC
```

FIG. 8C.

```
1651 AATCAGACAA GTCGAGGGTA CCGATTCACG CGTCAACAAA GGTGTCGCAG
1701 CCAAAAAAAA CATAACTTTT AAAGGGGGTA ATATCACCTT CGGCTCTCAA
1751 AAAGCCACAA CAGAAATCAA AGGCAATGTT ACCATCAATA AAAACACTAA
1801 CGCTACTCTT CGTGGTGCGA ATTTTGCCGA AAACAAATCG CCTTAAATA
1851 TAGCAGGAAA TGTTATTAAT AATGGCAACC TTACCACTGC CGGCTCCATT
1901 ATCAATATAG CCGGAAATCT TACTGTTTCA AAAGGCGCTA ACCTTCAAGC
1951 TATAACAAAT TACACTTTTA ATGTAGCCGG CTCATTTGAC AACAATGGCG
2001 CTTCAAACAT TTCCATTGCC AGAGGAGGGG CTAAATTTAA AGATATCAAT
2051 AACACCAGTA GCTTAAATAT TACCACCAAC TCTGATACCA CTTACCGCAC
2101 CATTATAAAA GGCAATATAT CCAACAAATC AGGTGATTTG AATATTATTG
2151 ATAAAAAAAG CGACGCTGAA ATCCAAATTG GCGGCAATAT CTCACAAAAA
2201 GAAGGCAATC TCACAATTTC TTCTGATAAA GTAAATATTA CCAATCAGAT
2251 AACAATCAAA GCAGGCGTTG AAGGGGGGCG TTCTGATTCA AGTGAGGCAG
2301 AAAATGCTAA CCTAACTATT CAAACCAAAG AGTTAAAATT GGCAGGAGAC
2351 CTAAATATTT CAGGCTTTAA TAAAGCAGAA ATTACAGCTA AAATGGCAG
2401 TGATTTAACT ATTGGCAATG CTAGCGGTGG TAATGCTGAT GCTAAAAAAG
```

FIG. 8D.

```
2451  TGACTTTTGA CAAGGTTAAA GATTCAAAAA TCTCGACTGA CGGTCACAAT
2501  GTAACACTAA ATAGCGAAGT GAAACGTCT  AATGGTAGTA GCAATGCTGG
2551  TAATGATAAC AGCACCGGTT TAACCATTTC CGCAAAAGAT GTAACGGTAA
2601  ACAATAACGT TACCTCCCAC AAGACAATAA ATATCTCTGC CGCAGCAGGA
2651  AATGTAACAA CCAAAGAAGG CACAACTATC AATGCAACCA CAGGCAGCGT
2701  GGAAGTAACT GCTCAAAATG GTACAATTAA AGGCAACATT ACCTCGCAAA
2751  ATGTAACAGT GACAGCAACA GAAAATCTTG TTACCACAGA GAATGCTGTC
2801  ATTAATGCAA CCAGCGGGCAC AGTAAACATT AGTACAAAAA CAGGGGATAT
2851  TAAAGGTGGA ATTGAATCAA CTTCCGGTAA TGTAAATATT ACAGCGAGCG
2901  GCAATACACT TAAGGTAAGT AATATCACTG GTCAAGATGT AACAGTAACA
2951  GCGGATGCAG GAGCCTTGAC AACTACAGCA GGCTCAACCA TTAGTGCGAC
3001  AACAGGCAAT GCAAATATTA CAACCAAAAC AGGTGATATC AACGGTAAAG
3051  TTGAATCCAG CTCCGGCTCT GTAACACTTG TTGCAACTGG AGCAACTCTT
3101  GCTGTAGGTA ATATTTCAGG TAACACTGTT ACTATTACTG CGGATAGCGG
3151  TAAATTAACC TCCACAGTAG GTTCTACAAT TAATGGGACT AATAGTGTAA
3201  CCACCTCAAG CCAATCAGGC GATATTGAAG GTACAATTTC TGGTAATACA
3251  GTAAATGTTA CAGCAAGCAC TGGTGATTTA ACTATTGGAA ATAGTGCAAA
```

FIG. 8E.

```
3301  AGTTGAAGCG  AAAAATGGAG  CTGCAACCTT  AACTGCTGAA  TCAGGCAAAT
3351  TAACCACCCA  AACAGGCTCT  AGCATTACCT  CAAGCAATGG  TCAGACAACT
3401  CTTACAGCCA  AGGATAGCAG  TATCGCAGGA  AACATTAATG  CTGCTAATGT
3451  GACGTTAAAT  ACCACAGGCA  CTTTAACTAC  TACAGGGGAT  TCAAAGATTA
3501  ACGCAACCAG  TGGTACCTTA  ACAATCAATG  CAAAAGATGC  CAAATTAGAT
3551  GGTGCTGCAT  CAGGTGACCG  CACAGTAGTA  AATGCAACTA  ACGCAAGTGG
3601  CTCTGGTAAC  GTGACTGCGA  AAACCTCAAG  CAGCGTGAAT  ATCACCGGGG
3651  ATTTAAACAC  AATAAATGGG  TTAAATATCA  TTTCGGAAAA  TGGTAGAAAC
3701  ACTGTGCGCT  TAAGAGGCAA  GGAAATTGAT  GTGAAATATA  TCCAACCAGG
3751  TGTAGCAAGC  GTAGAAGAGG  TAATTGAAGC  GAAACGCGTC  CTTGAGAAGG
3801  TAAAAGATTT  ATCTGATGAA  GAAAGAGAAA  CACTAGCCAA  ACTTGGTGTA
3851  AGTGCTGTAC  GTTTCGTTGA  GCCAAATAAT  GCCATTACGG  TTAATACACA
3901  AAACGAGTTT  ACAACCAAAC  CATCAAGTCA  AGTGACAATT  TCTGAAGGTA
3951  AGGCGTGTTT  CTCAAGTGGT  AATGGCGCAC  GAGTATGTAC  CAATGTTGCT
4001  GACGATGGAC  AGCAGTAGTC  AGTAATTGAC  AAGGTAGATT  TCATCCTGCA
4051  ATGAAGTCAT  TTTATTTTCG  TATTATTTAC  TGTGTGGGTT  AAAGTTCAGT
```

FIG. 8F.

```
4101  ACGGGCTTTA CCCACCCTGT AAAAAATTAC GAAAAATACA ATAAAGTATT
4151  TTTAACAGGT TATTATTATG AAAAACATAA AAAGCAGATT AAAACTCAGT
4201  GCAATATCAA TATTGCTTGG CTTGGCTTCT TCATCGACGT ATGCAGAAGA
4251  AGCGTTTTTA GTAAAAGGCT TTCAGTTATC TGGCGCG
```

FIG. 9A.

```
  1  GGGAATGAGC GTCGTACACG GTACAGCAAC CATGCAAGTA GACGGCAATA
 51  AAACCACTAT CCGTAATAGC GTCAATGCTA TCATCAATTG GAAACAATTT
101  AACATTGACC AAAATGAAAT GGAGCAGTTT TTACAAGAAA GCAGCAACTC
151  TGCCGTTTC  AACCGTGTTA CATCTGACCA AATCTCCCAA TTAAAAGGGA
201  TTTTAGATTC TAACGGACAA GTCTTTTTAA TCAACCCAAA TGGTATCACA
251  ATAGGTAAAG ACGCAATTAT TAACACTAAT GGCTTTACTG CTTCTACGCT
301  AGACATTTCT AACGAAAACA TCAAGGCGCG TAATTTCACC CTTGAGCAAA
351  CCAAGGATAA AGCACTCGCT GAAATCGTGA ATCACGGTTT AATTACCGTT
401  GGTAAAGACG GTAGCGTAAA CCCTTATTGGT GGCAAAGTGA AAAACGAGGG
451  CGTGATTAGC GTAAATGGCG GTAGTATTTC TTTACTTGCA GGGCAAAAAA
501  TCACCATCAG CGATATAATA AATCCAACCA TCACTTACAG CATTGCTGCA
551  CCTGAAAACG AAGCGATCAA TCTGGGCGAT ATTTTTGCCA AGGTGGTAA
601  CATTAATGTC CGCGCTGCCA CTATTCGCCA TAAAGGTAAA CTTTCTGCCG
651  ACTCTGTAAG CAAAGATAAA AGTGGTAACA TTGTTCTCTC TGCCAAAGAA
701  GGTGAAGCGG AAATTGGCGG TGTAATTTCC GCTCAAAATC AGCAAGCCAA
751  AGGTGGTAAG TTGATGATTA CAGGTGATAA AGTCACATTA AAAACAGGTG
```

FIG. 9B.

```
 801  CAGTTATCGA CCTTTCAGGT AAAGAAGGGG GAGAGACTTA TCTTGGCGGT
 851  GATGAGCGTG GCGAAGGTAA AAATGGTATT CAATTAGCGA AGAAAACCTC
 901  TTTAGAAAAA GGCTCGACAA TTAATGTATC AGGCAAAGAA AAAGGCGGGC
 951  GCGCTATTGT ATGGGGCGAT ATTGCATTAA TTAATGGTAA CATTAATGCT
1001  CAAGGTAGCG ATATTGCTAA AACTGGCGGC TTTGTGGAAA CATCAGGACA
1051  TGACTTATCC ATTGGTGATG ATGTGATTGT TGACGCTAAA GAGTGGTTAT
1101  TAGACCCAGA TGATGTGTCC ATTGAAACTC TTACACATCTGG ACGCAATAAT
1151  ACCGGCGAAA ACCAAGGATA TACAACAGGA GATGGGACTA AAGAGTCACC
1201  TAAAGTAAT AGTATTTCTA AACCTACATT AACAAACTCA ACTCTTGAGC
1251  AAATCCTAAG AAGAGGTTCT TATGTTAATA TCACTGCTAA TAATAGAATT
1301  TATGTTAATA GCTCCATCAA CTTATCTAAT GGCAGTTTAA CACTTCACAC
1351  TAAACGAGAT GGAGTTAAAA TTAACGGTGA TATTACCTCA AACGAAAATG
1401  GTAATTTAAC CATTAAAGCA GGCTCTTGGG TTGATGTTCA TAAAAACATC
1451  ACGCTTGGTA CGGGTTTTTT GAATATTGTC GCTGGGGATT CTGTAGCTTT
1501  TGAGAGAGAG GGCGATAAAG CACGTAACGC AACAGATGCT CAAATTACCG
1551  CACAAGGGAC GATAACCGTC AATAAAGATG ATAAACAATT TAGATTCAAT
1601  AATGTATCTA TTAACGGGAC GGGCAAGGGT TTAAAGTTTA TTGCAAATCA
```

FIG. 9C.

```
1651 AAATAATTTC ACTCATAAAT TTGATGGCGA AATTAACATA TCTGGAATAG
1701 TAACAATTAA CCAAACCACG AAAAAAGATG TTAAATACTG GAATGCATCA
1751 AAAGACTCTT ACTGGAATGT TTCTTCTCTT ACTTTGAATA CGGTGCAAAA
1801 ATTTACCTTT ATAAAATTCG TTGATAGCGG CTCAAATTCC CAAGATTTGA
1851 GGTCATCACG TAGAAGTTTT GCAGGCGTAC ATTTTAACGG CATCGGAGGC
1901 AAACAAACT TCAACATCGG AGCTAACGCA AAAGCCTTAT TTAAATTAAA
1951 ACCAAACGCC GCTACAGACC CAAAAAAAGA ATTACCTATT ACTTTTAACG
2001 CCAACATTAC AGCTACCGGT AACAGTGATA GCTCTGTGAT GTTTGACATA
2051 CACGCCAATC TTACCTCTAG AGCTGCCCGC ATAAACATGG ATTCAATTAA
2101 CATTACCGGC GGGCTTGACT TTTCCATAAC ATCCCATAAT CGCAATAGTA
2151 ATGCTTTTGA AATCAAAAAA GACTTAACTA TAAATGCAAC TGGCTCGAAT
2201 TTTAGTCTTA AGCAAACGAA AGATTCTTTT TATAATGAAT ACAGCAAACA
2251 CGCCATTAAC TCAAGTCATA ATCTAACCAT TCTTGGCGGC AATGTCACTC
2301 TAGGTGGGGA AAATTCAAGC AGTAGCATTA CGGGCAATAT CAATATCACC
2351 AATAAAGCAA ATGTTACATT ACAAGCTGAC ACCAGCAACA GCAACACAGG
2401 CTTGAAGAAA AGAACTCTAA CTCTTGGCAA TATATCTGTT GAGGGAATT
```

FIG. 9D.

```
2451 TAAGCCTAAC TGGTGCAAAT GCAAACATTG TCGGCAATCT TTCTATTGCA
2501 GAAGATTCCA CATTTAAAGG AGAAGCCAGT GACAACCTAA ACATCACCGG
2551 CACCTTTACC AACAACGGTA CCGCCAACAT TAATATAAAA CAAGGAGTGG
2601 TAAAACTCCA AGGCGATATT ATCAATAAAG GTGGTTTAAA TATCACTACT
2651 AACGCCTCAG GCACTCAAAA AACCATTATT AACGAAAATA TAACTAACGA
2701 AAAAGGCGAC TTAAACATCA AGAATATTAA AGCCGACGCC GAAATCCAAA
2751 TTGGCGGCAA TATCTCACAA ATCTCACAAT AAAGCAGGCG TTCTTCTGAT
2801 AAAGTAAATA TTACCAATCA GATAACAATC AAAGCAGGCG TTGAAGGGGG
2851 GCGTTCTGAT TCAAGTGAGG CAGAAAATGC TAACCTAACT ATTCAAACCA
2901 AAGAGTTAAA ATTGGCAGGA GACCTAAATA TTTCAGGCTT TAATAAAGCA
2951 GAAATTACAG CTAAAAATGG CAGTGATTTA ACTATTGGCA ATGCTAGCGG
3001 TGGTAATGCT GATGCTAAAA AAGTGACTTT TGACAAGGTT AAAGATTCAA
3051 AAATCTCGAC TGACGGTCAC AATGTAACAC TAAATAGCGA AGTGAAAACG
3101 TCTAATGGTA GTAGCAATGC TGGTAATGAT AACAGCACCG GTTTAACCAT
3151 TTCCGCAAAA GATGTAACGG TAAACAATAA CGTTACCTCC CACAAGACAA
3201 TAAATATCTC TGCCGCAGCA GGAAATGTAA CAACCAAAGA AGGCACAACT
3251 ATCAATGCAA CCACAGGCAG CGTGGAAGTA ACTGCTCAAA ATGGTACAAT
```

FIG. 9E.

```
3301  TAAAGGCAAC  ATTACCTCGC  AAAATGTAAC  AGTGACAGCA  ACAGAAAATC
3351  TTGTTACCAC  AGAGAATGCT  GTCATTAATG  CAACCAGCGG  CACAGTAAAC
3401  ATTAGTACAA  AAACAGGGGA  TATTAAAGGT  GGAATTGAAT  CAACTTCCGG
3451  TAATGTAAAT  ATTACAGCGA  GCGGCAATAC  ACTTAAGGTA  AGTAATATCA
3501  CTGGTCAAGA  TGTAACAGTA  ACAGCGGATG  CAGGAGCCTT  GACAACTACA
3551  GCAGGCTCAA  CCATTAGTGC  GACAACAGGC  AATGCAAATA  TTACAACCAA
3601  AACAGGTGAT  ATCAACGGTA  AAGTTGAATC  CAGCTCCGGC  TCTGTAACAC
3651  TTGTTGCAAC  TGGAGCAACT  CTTGCTGTAG  GTAATATTTC  AGGTAACACT
3701  GTTACTATTA  CTGCGGATAG  CGGTAAATTA  ACCTCCACAG  TAGGTTCTAC
3751  AATTAATGGG  ACTAATAGTG  TAACCACCTC  AAGCCAATCA  GGCGATATTG
3801  AAGGTACAAT  TTCTGGTAAT  ACAGTAAATG  TTACAGCAAG  CACTGGTGAT
3851  TTAACTATTG  GAAATAGTGC  AAAAGTTGAA  GCGAAAAATG  GAGCTGCAAC
3901  CTTAACTGCT  GAATCAGGCA  AATTAACCAC  CCAAACAGGC  TCTAGCATTA
3951  CCTCAAGCAA  TGGTCAGACA  ACTCTTACAG  CCAAGGATAG  CAGTATCGCA
4001  GGAAACATTA  ATGCTGCTAA  TGTGACGTTA  AATACCACAG  GCACTTTAAC
4051  TACTACAGGG  GATTCAAAGA  TTAACGCAAC  CAGTGGTACC  TTAACAATCA
```

FIG. 9F.

```
4101 ATGCAAAAGA TGCCAAATTA GATGGTGCTG CATCAGGTGA CCGCACAGTA
4151 GTAAATGCAA CTAACGCAAG TGGCTCTGGT AACGTGACTG CGAAACCTC
4201 AAGCAGCGTG AATATCACCG GGGATTTAAA CACAATAAAT GGGTTAAATA
4251 TCATTTCGGA AAATGGTAGA AACACTGTGC GCTTAAGAGG CAAGGAAATT
4301 GATGTGAAAT ATATCCAACC AGGTGTAGCA AGCGTAGAAG AGGTAATTGA
4351 AGCGAAACGC GTCCTTGAGA AGGTAAAAGA TTTATCTGAT GAAGAAAGAG
4401 AAACACTAGC CAAACTTGGT GTAAGTGCTG TACGTTTCGT TGAGCCAAAT
4451 AATGCCATTA CGGTTAATAC ACAAAACGAG TTTACAACCA AACCATCAAG
4501 TCAAGTGACA ATTTCTGAAG GTAAGGCGTG TTTCTCAAGT GGTAATGGCG
4551 CACGAGTATG TACCAATGTT GCTGACGATG GACAGCAGTA GTCAGTAATT
4601 GACAAGGTAG ATTTCATCCT GCAATGAAGT CATTTATTT TCGTATTATT
4651 TACTGTGTGG GTTAAAGTTC AGTACGGGCT TTACCCACCT TGTAAAAAAT
4701 TA
```

FIG. 10A. COMPARISON OF DERIVED AMINO ACID SEQUENCE

```
                    1                                                    50
Hmw3com   ..........  ..........  ..........  ..........  ..........
Hmw4com   ..........  ..........  ..........  ..........  ..........
Hmw1com   MNKIYRLKFS  KRLNALVAVS  ELARGCDHST  EKGSEKPARM  KVRHLALKPL
Hmw2com   MNKIYRLKFS  KRLNALVAVS  ELARGCDHST  EKGSEKPARM  KVRHLALKPL 51                                                   100
Hmw3com   ..........  ..........  ..........  ..........  ..........
Hmw4com   ..........  ..........  ..GMSVVHGT  ATMQVDGNKT  TIRNSVNAII
Hmw1com   SAMLLSLGVT  SIPQSVLASG  LQGMSVVHGT  ATMQVDGNKT  TIRNSVNAII
Hmw2com   SAMLLSLGVT  SIPQSVLASG  LQGMSVVHGT  ATMQVDGNKT  TIRNSVNAII 101                                                   150
Hmw3com   ..........  ..........  ..........  ..........  ..........
Hmw4com   NWKQFNIDQN  EMEQFLQESS  NSAVFNRVTS  DQISQLKGIL  DSNGQVFLIN
```

FIG. 10B.

```
Hmw1com  NWKQFNIDQN  EMVQFLQENN  NSAVFNRVTS  NQISQLKGIL  DSNGQVFLIN
Hmw2com  NWKQFNIDQN  EMVQFLQENN  NSAVFNRVTS  NQISQLKGIL  DSNGQVFLIN
                                                                200
Hmw3com  ..........  ..........  ..........  ..........  ..........
Hmw4com  PNGITIGKDA  IINTNGFTAS  TLDISNENIK  ARNFTLEQTK  DKALAEIVNH
Hmw1com  PNGITIGKDA  IINTNGFTAS  TLDISNENIK  ARNFTLEQTK  DKALAEIVNH
Hmw2com  PNGITIGKDA  IINTNGFTAS  TLDISNENIK  ARNFTLEQTK  DKALAEIVNH
                                                                250
Hmw3com  ..........  ..........  ..........  ..........  ..........
Hmw4com  GLITVGKDGS  VNLIGGKVKN  EGVISVNGGS  ISLLAGQKIT  ISDIINPTIT
Hmw1com  GLITVGKDGS  VNLIGGKVKN  EGVISVNGGS  ISLLAGQKIT  ISDIINPTIT
Hmw2com  GLITVGKDGS  VNLIGGKVKN  EGVISVNGGS  ISLLAGQKIT  ISDIINPTIT
                                                                300
Hmw3com  ..........  INLGDIFAKG  GNINVRAATI  RNKGKLSADS  VSKDKSGNIV
```

FIG. 10C.

```
Hmw4com    YSIAAPENEA  INLGDIFAKG  GNINVRAATI  RNKGKLSADS  VSKDKSGNIV
Hmw1com    YSIAAPENEA  VNLGDIFAKG  GNINVRAATI  RNKGKLSADS  VSKDKSGNIV
Hmw2com    YSIAAPENEA  VNLGDIFAKG  GNINVRAATI  RNKGKLSADS  VSKDKSGNIV 301                                                   350
Hmw3com    LSAKEGEAEI  GGVISAQNQQ  AKGGKLMITG  DKVTLKTGAV  IDLSGKEGGE
Hmw4com    LSAKEGEAEI  GGVISAQNQQ  AKGGKLMITG  DKVTLKTGAV  IDLSGKEGGE
Hmw1com    LSAKEGEAEI  GGVISAQNQQ  AKGGKLMITG  DKVTLKTGAV  IDLSGKEGGE
Hmw2com    LSAKEGEAEI  GGVISAQNQQ  AKGGKLMITG  DKVTLKTGAV  IDLSGKEGGE 351                                                   400
Hmw3com    TYLGGDERGE  GKNGIQLAKK  TTLEKGSTIN  VSGKEKGGRA  IVWGDIALID
Hmw4com    TYLGGDERGE  GKNGIQLAKK  TTLEKGSTIN  VSGKEKGGRA  IVWGDIALID
Hmw1com    TYLGGDERGE  GKNGIQLAKK  TTLEKGSTIN  VSGKEKGGRA  IVWGDIALID
Hmw2com    TYLGGDERGE  GKNGIQLAKK  TTLEKGSTIN  VSGKEKGGRA  IVWGDIALID
```

FIG. 10D.

```
        401                                                              450
Hmw3com GNINAQGK.D IAKTGGFVET SGHYLSIDDN AIVKTKEWLL DPENVTIEAP
Hmw4com GNINAQGS.D IAKTGGFVET SGHDLSIGDD VIVDAKEWLL DPDDVSIETL
Hmw1com GNINAQGSGD IAKTGGFVET SGHDLFIKDN AIVDAKEWLL DPDNVTINAE
Hmw2com GNINAQGSGD IAKTGGFVET SGHYLSIESN AIVKTKEWLL DPDDVTIEAE 451                                                              500
Hmw3com SASRVELGAD RNSHSAEVIK VTLKKNNTSL TTLTNTTISN LLKSAHVVNI
Hmw4com TSGRNNTGEN QGYTTGDGTK ESPKGNSISK PTLTNSTLEQ ILRRGSYVNI
Hmw1com TAGRSNTSED DEYTGSGNSA STPKRNKE.K TTLTNTTLES ILKKGTFVNI
Hmw2com DPLRNNTGIN DEFPTGTGEA SDPKKNSELK TTLTNTTISN YLKNAWTMNI 501                                                              550
Hmw3com TARRKLTVNS SISIERGSHL ILHSEGQGGQ GVQIDKDITS .E...GGNLT
Hmw4com TANNRIYVNS SINLSNGS.L TLHTK...RD GVKINGDITS NE...NGNLT
Hmw1com TANQRIYVNS SINL.SNGSL TLWSEGRSGG GVEINNDITT GDDTRGANLT
Hmw2com TASRKLTVNS SINGSNGSHL ILHSKGQRGG GVQIDGDIT. ...SKGGNLT
```

FIG. 10E.

```
         551                                                              600
Hmw3com  IYSGGWVDVH  KNITLGS.GF  LNITTKEGDI  AFEDKSGR..  ..NNLTITAQ
Hmw4com  IKAGSWVDVH  KNITLGT.GF  LNIVAGDS.V  AFEREGDKAR  NATDAQITAQ
Hmw1com  IYSGGWVDVH  KNISLGAQGN  INITAKQD.I  AFEKGSNQV.  .......ITGQ
Hmw2com  IYSGGWVDVH  KNITLD.QGF  LNITA.AS.V  AFEGGNNKAR  DANNLTITAQ 601                                                              650
Hmw3com  GTITSG.NSN  GFRFNNVSLN  SLGGKLSFTD  SREDRGRRTK  GNISNKFDGT
Hmw4com  GTITVNKDDK  QFRFNNVSIN  GTGKGLKFIA  NQN.......  .NFTHKFDGE
Hmw1com  GTIT.SGNQK  GFRFNNVSLN  GTGSGLQFTT  KRTN......K  YAITNKFEGT
Hmw2com  GTVTITGEGK  DFRANNVSLN  GTGKGLNIIS  SVNN......  ..LTHNLSGT 651                                                              700
Hmw3com  LNISGTVDIS  MKAPKVSWFY  RD.KGRTYWN  VTTLNVTSGS  KFNLSIDSTG
Hmw4com  INISGIVTIN  QTTKKDVKYW  NA.SKDSYWN  VSSLTLNTVQ  KFTF.IKFVD
Hmw1com  LNISGKVNIS  MVLPKNESGY  DKFKGRTYWN  LTSLNVSESG  EFNLTIDSRG
```

FIG. 10F.

```
Hmw2com  INISGNITIN QTTRKNTSYW QTSHD.SHWN VSALNLETGA NFTF.IKYIS
                                                              750

701
Hmw3com  SGSTG...PS IRNA..ELNG ITFN....KA TFNIAQGSTA NFSIKASIMP
Hmw4com  SGSNS...QD LRSSRRSFAG VHFNGIGGKT NFNIGANAKA LFKLKPNAAT
Hmw1com  SDSAGTLTQ. ....PYNLNG ISFN...KDT TFNVERNARV NFDIKAPIGI
Hmw2com  SNSKGLTTQY RSSAGVNFNG V..N...GNM SFNLKEGAKV NFKLKPNENM 751                                                  800
Hmw3com  FKSNANYAL. FNEDISVSG. .GGSVNFKLN ASSSNIQTPG VIIKSQNFNV
Hmw4com  DPKKELPIT. FNANITATGN SDSSVMFDIH A...NLTSRA AGINMDSINI
Hmw1com  NKYSSLNYAS FNGNISVSG. .GGSVDFTLL ASSSNVQTPG VVINSKYFNV
Hmw2com  NTSKPLPI.R FLANITATG. .GGSVFFDIY ANHS...GRG AELKMSEINI 801                                                  850
Hmw3com  SGGSTLNLKA EGSTETAFSI ENDLNLNATG GNITIRQVEG T..DSRVNKG
Hmw4com  TGGLDFSITS HNRNSNAFEI KKDLTINATG SNFSLKQTKD SFYNEYSKHA
```

FIG. 10G.

```
Hmw1com  STGSSLRFKT  SGSTKTGFSI  EKDLTLNATG  GNITLLQVEG  T..DGMIGKG
Hmw2com  SNGANFTLNS  HVRGDDAFKI  NKDLTINATN  SNFSLRQTKD  DFYDGYARNA
                851                                            900

Hmw3com  VAAKKNITFK  GGNITFGSQK  ATTEIKGNVT  INKNTNATLR  GANFAEN...
Hmw4com  INSSHNLTIL  GGNVTLGGEN  SSSSITGNIN  ITNKANVTLQ  ADTSNSNTGL
Hmw1com  IVAKKNITFE  GGNITFGSRK  AVTEIEGNVT  INNNANVTLI  GSDFDNHQ..
Hmw2com  INSTYNISIL  GGNVTLGGQN  SSSSITGNIT  IEKAANVTLE  ANNAPNQQNI
                901                                            950

Hmw3com  KSPLNIAGNV  INNGNLTTAG  SIINIAGNLT  VSKGANLQAI  TNYTFNVAGS
Hmw4com  KKRTLTLGNI  SVEGNLSLTG  ANANIVGNLS  IAEDSTFKGE  ASDNLNITGT
Hmw1com  KPLTIKKDVI  INSGNLTAGG  NIVNIAGNLT  VESNANFKAI  TNFTFNVGGL
Hmw2com  RDRVIKLGSL  LVNGSLSLTG  ENADIKGNLT  ISESATFKGK  TRDTLNITGN
                951                                           1000
```

FIG. 10H.

| | | | | | | |
|---|---|---|---|---|---|---|
| Hmw3com | FDNNGASNIS | IARGGAKFK. | DINNTSSLNI | TTNSDTTYRT | IIKGNISNKS | |
| Hmw4com | FTNNGTANIN | IKQGVVKLQG | DINNKGGLNI | TTNASGTQKT | IINGNITNEK | |
| Hmw1com | FDNKGNSNIS | IAKGGARFK. | DIDNSKNLSI | TTNSSSTYRT | IISGNITNKN | |
| Hmw2com | FTNNGTAEIN | ITQGVVKLG. | NVTNDGDLNI | TTHAKRNQRS | IIGGDIINNK | |
| | 1001 | | | | | 1050 |
| Hmw3com | GDLNIIDKKS | DAEIQIGGNI | SQKEGNLTIS | SDKVNITNQI | TIKAGVEGGR | |
| Hmw4com | GDLNIKNIKA | DAEIQIGGNI | SQKEGNLTIS | SDKVNITNQI | TIKAGVEGGR | |
| Hmw1com | GDLNITNEGS | DTEMQIGGDI | SQKEGNLTIS | SDKINITKQI | TIKAGVDGEN | |
| Hmw2com | GSLNITDSNN | DAEIQIGGNI | SQKEGNLTIS | SDKINITKQI | TIKKGIDGED | |
| | 1051 | | | | | 1100 |
| Hmw3com | SDSSEAENAN | LTIQTKELKL | AGDLNISGFN | KAEITAKNGS | DLTIGNASGG | |
| Hmw4com | SDSSEAENAN | LTIQTKELKL | AGDLNISGFN | KAEITAKNGS | DLTIGNASGG | |
| Hmw1com | SDSDATNNAN | LTIKTKELKL | TQDLNISGFN | KAEITAKDGS | DLTIGNTNSA | |
| Hmw2com | SSSDATSNAN | LTIKTKELKL | TEDLSISGFN | KAEITAKDGR | DLTIGNSNDG | |

FIG. 10I.

```
          1101                                                        1150
Hmw3com   N..ADAKKVT  FDKVKDSKIS  TDGHNVTLNS  EVKT..SNGS  SNAGNDNSTG
Hmw4com   N..ADAKKVT  FDKVKDSKIS  TDGHNVTLNS  EVKT..SNGS  SNAGNDNSTG
Hmw1com   D.GTNAKKVT  FNQVKDSKIS  ADGHKVTLHS  KVETSGSNNN  TEDSSDNNAG
Hmw2com   NSGAEAKKVT  FNNVKDSKIS  ADGHNVTLNS  KVKTSSSNGG  RESNSDNDTG 1151                                                        1200
Hmw3com   LTISAKDVTV  NNNVTSHKTI  NISAAAGNVT  TKEGTTINAT  TGSVEVTAQN
Hmw4com   LTISAKDVTV  NNNVTSHKTI  NISAAAGNVT  TKEGTTINAT  TGSVEVTAQN
Hmw1com   LTIDAKNVTV  NNNITSHKAV  SISATSGEIT  TKTGTTINAT  TGNVEIT....
Hmw2com   LTITAKNVEV  NKDVTSLKTV  NITA.SEKVT  TTAGSTINAT  NGKASIT....

1201                                                        1250
Hmw3com   GTIKGNITSQ  NVTVTATENL  VTTENAVINA  TSGTVNISTK  TGDIKGGIES
Hmw4com   GTIKGNITSQ  NVTVTATENL  VTTENAVINA  TSGTVNISTK  TGDIKGGIES
Hmw1com   ..........  ..........  ..........  ........AQ  TGDIKGGIES
```

FIG. 10J.

```
Hmw2com  ..........  ..........  ..........  ..........  ..........
                     1251                                            1300
Hmw3com  TSGNVNITAS  GNTLKVSNIT  GQDVTVTADA  GALTTTAGST  ISATTGNANI
Hmw4com  TSGNVNITAS  GNTLKVSNIT  GQDVTVTADA  GALTTTAGST  ISATTGNANI
Hmw1com  SSGSVTLTAT  EGALAVSNIS  GNTVTVTANS  GALTTLAGST  IKG.TESVTT
Hmw2com  ..........  ..........  ..........  ..........  ...TK T....
                     1301                                            1350
Hmw3com  TTKTGDINGK  VESSSGSVTL  VATGATLAVG  NISGNTVTIT  ADSGKLTSTV
Hmw4com  TTKTGDINGK  VESSSGSVTL  VATGATLAVG  NISGNTVTIT  ADSGKLTSTV
Hmw1com  SSQSGDIG..  ..........  .........G  TISGGTVEVK  ATESLTTQSN
Hmw2com  ....GDIS..  ..........  .........G  TISGNTVSVS  ATVDLTTKSG
                     1351                                            1400
Hmw3com  GSTINGTNSV  TTSSQSGDIE  GTISGNTVNV  TASTGDLTIG  NSAKVEAKNG
Hmw4com  GSTINGTNSV  TTSSQSGDIE  GTISGNTVNV  TASTGDLTIG  NSAKVEAKNG
```

FIG. 10K.

```
Hmw1com  SKIKATTGEA  NVTSATGTIG  GTISGNTVNV  TANAGDLTVG  NGAEINATEG
Hmw2com  SKIEAKSGEA  NVTSATGTIG  GTISGNTVNV  TANAGDLTVG  NGAEINATEG
                                                                1450

Hmw3com  AATLTAESGK  LTTQTGSSIT  SSNGQTTLTA  KDSSIAGNIN  AANVTLNTTG
Hmw4com  AATLTAESGK  LTTQTGSSIT  SSNGQTTLTA  KDSSIAGNIN  AANVTLNTTG
Hmw1com  AATLTTSSGK  LTTEASSHIT  SAKGQVNLSA  QDSSVAGSIN  AANVTLNTTG
Hmw2com  AATLTATGNT  LTTEAGSSIT  STKGQVDLLA  QNSSIAGNIN  AANVTLNTTG
1401                                                            1500

Hmw3com  TLTTTGDSKI  NATSGTLTIN  AKDAKLDGAA  SGDRTVVNAT  NASGSGNVTA
Hmw4com  TLTTTGDSKI  NATSGTLTIN  AKDAKLDGAA  SGDRTVVNAT  NASGSGNVTA
Hmw1com  TLTTVKGSNI  NATSGTLTIN  AKDAELNGAA  LGNHTVVNAT  NANGSGSVIA
Hmw2com  TLTTVAGSDI  KATSGTLTIN  AKDAKLNGDA  SGDSTEVNAV  NASGSGSVTA
1451                                                            1550

```
Hmw3com  KTSSSVNITG  DLNTINGLNI  ISENGRNTVR  LRGKEIDVKY  IQPGVASVEE
Hmw4com  KTSSSVNITG  DLNTINGLNI  ISENGRNTVR  LRGKEIDVKY  IQPGVASVEE
Hmw1com  TTSSRVNITG  DLITINGLNI  ISKNGINTVL  LKGVKIDVKY  IQPGIASVDE
Hmw2com  ATSSSVNITG  DLNTVNGLNI  ISKDGRNTVR  LRGKEIEVKY  IQPGVASVEE
                    1551                                      1600

Hmw3com  VIEAKRVLEK  VKDLSDEERE  TLAKLGVSAV  RFVEPNNAIT  VNTQNEFTTK
Hmw4com  VIEAKRVLEK  VKDLSDEERE  TLAKLGVSAV  RFVEPNNAIT  VNTQNEFTTK
Hmw1com  VIEAKRILEK  VKDLSDEERE  ALAKLGVSAV  RFIEPNNTIT  VDTQNEFATR
Hmw2com  VIEAKRVLEK  VKDLSDEERE  TLAKLGVSAV  RFVEPNNTIT  VNTQNEFTTR
         1601                                      1632

Hmw3com  PSSQVTISEG  KACFSSGNGA  RVCTNVADDG  QQ
Hmw4com  PSSQVTISEG  KACFSSGNGA  RVCTNVADDG  QQ
Hmw1com  PLSRIVISEG  RACFSNSDGA  TVCVNIADNG  R.
Hmw2com  PSSQVIISEG  KACFSSGNGA  RVCTNVADDG  QP
```

5,603,938

1

HIGH MOLECULAR WEIGHT SURFACE PROTEINS OF NON-TYPEABLE HAEMOPHILUS

FIELD OF INVENTION

This invention relates to high molecular weight proteins of non-typeable haemophilus.

BACKGROUND TO THE INVENTION

Non-typeable *Haemophilus influenzae* are non-encapsulated organisms that are defined by their lack of reactivity with antisera against known *H. influenzae* capsular antigens.

These organisms commonly inhabit the upper respiratory tract of humans and are frequently responsible for infections, such as otitis media, sinusiris, conjunctivitis, bronchitis and pneumonia. Since these organisms do not have a polysaccharide capsule, they are not controlled by the present *Haemophilus influenzae* type b (Hib) vaccines, which are directed towards Hib bacterial capsular polysaccharides. The non-typeable strains, however, do produce surface antigens that can elicit bactericidal antibodies. Two of the major outer membrane proteins, P2 and P6, have been identified as targets of human serum bactericidal activity. However, it has been shown that the P2 protein sequence is variable, in particular in the non-typeable Haemophilus strains. Thus, a P2-based vaccine would not protect against all strains of the organism.

There have previously been identified by Barenkamp et al (*Pediatr. Infect. Dis. J.*, 9:333–339, 1990) a group of high-molecular-weight (HMW) proteins that appeared to be major targets of antibodies present in human convalescent sera. Examination of a series of middle ear isolates revealed the presence of one or two such proteins in most strains. However, prior to the present invention, the structures of these proteins were unknown as were pure isolates of such proteins.

SUMMARY OF INVENTION

The inventors, in an effort to further characterize the high molecular weight (HMW) Haemophilus proteins, have cloned, expressed and sequenced the genes coding for two immunodominant HMW proteins (designated HMW1 and HMW2) from a prototype non-typeable Haemophilus strain and have cloned, expressed and almost completely sequenced the genes coding for two additional immunodominant HMW proteins (designated HMW3 and HMW4) from another non-typeable Haemophilus strain.

in accordance with one aspect of the present invention, therefore, there is provided an isolated and purified gene coding for a high molecular weight protein of a non-typeable Haemophilus strain, particularly a gene coding for protein HMW1, HMW2, HMW3 or HMW4, as well as any variant or fragment of such protein which retains the immunological ability to protect against disease caused by a non-typeable Haemophilus strain. In another aspect, the invention provides a high molecular weight protein of non-typeable *Haemophilus influenzae* which is encoded by these genes.

BRIEF DESCRIPTION OF DRAWINGS

FIG. 1A–1G is a DNA sequence of a gene coding for protein HMW1 (SEQ ID NO: 1);

FIG. 2A & 2B is a derived amino acid sequence of protein HMW1 (SEQ ID NO: 2);

2

Figure 5A:
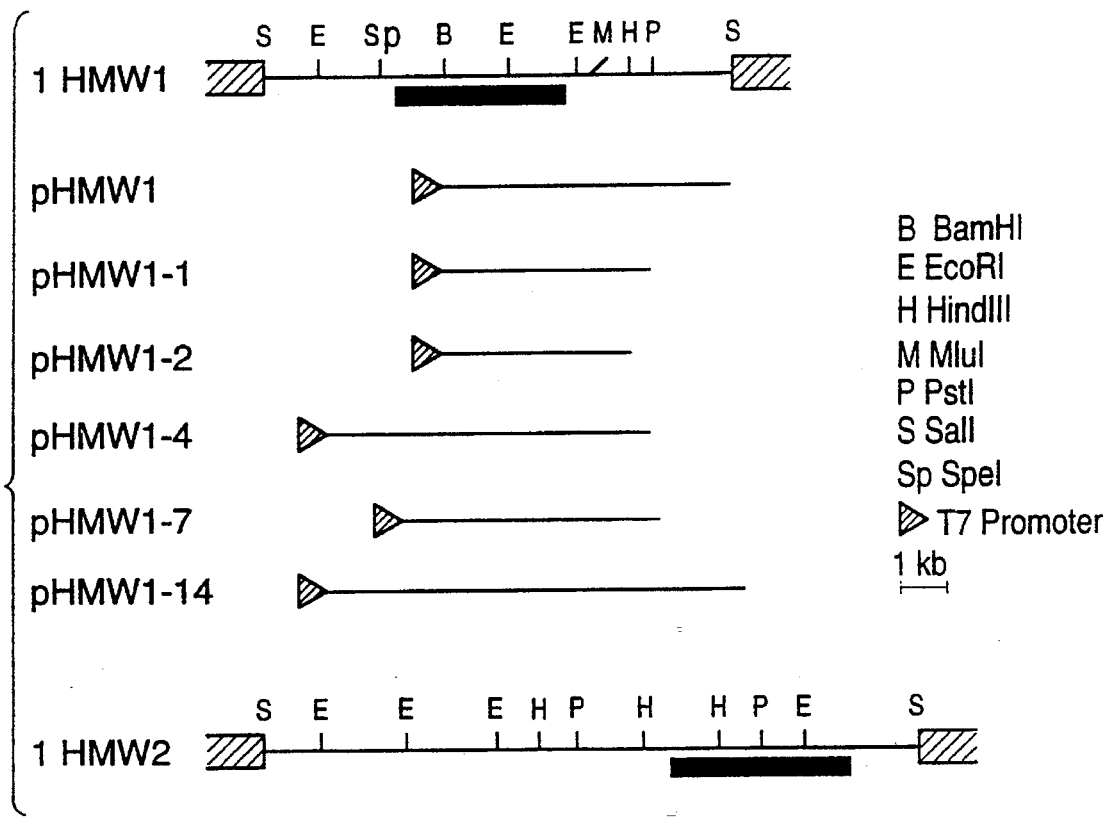

FIG. 3A–3G is a DNA sequence of a gene coding for protein HMW2 (SEQ ID NO: 3);

FIG. 4A & 4B is a derived amino acid sequence of HMW2 (SEQ ID NO: 4);

FIG. 5A shows restriction maps of representative recombinant phages which contained the HMW1 or HMW2 structural genes, the locations of the structural genes being indicated by the shaded bars;

FIG. 5B shows the restriction map of the T7 expression vector pT7-7;

FIG. 6A–6L contains the DNA sequence of a gene cluster for the hmw1 gene (SEQ ID NO: 5), comprising nucleotides 351 to 4958 (ORF a) (as in FIG. 1), as well as two additional downstream genes in the 3' flanking region, comprising ORFs b, nucleotides 5114–6748 and c nucleotides 7062–9011;

FIG. 7A–7L contains the DNA sequence of a gene cluster for the hmw2 gene (SEQ ID NO: 6), comprising nucleotides 792 to 5222 (ORF a) (as in FIG. 3), as well as two additional downstream genes in the 3' flanking region, comprising ORFs b, nucleotides 5375–7009, and c, nucleotides 7249–9198;

FIG. 8A–8F is a partial DNA sequence of a gene coding for protein HMW3 (SEQ ID NO: 7);

FIG. 9A–9F is a partial DNA sequence of a gene coding for protein HMW4 (SEQ ID NO: 8); and FIG. 10A–10L is a comparison table for the derived amino acid sequence for proteins HMW1, HMW2, HMW3 and HMW4.

GENERAL DESCRIPTION OF INVENTION

The DNA sequences of the genes coding for HMW1 and HMW2, shown in FIGS. 1 and 3 respectively, were shown to be about 80% identical, with the first 1259 base pairs of the genes being identical. The derived amino acid sequences of the two HMW proteins, shown in FIGS. 2 and 4 respectively, are about 70% identical. Furthermore, the encoded proteins are antigenically related to the filamentous hemagglutinin surface protein of *Bordetella pertussis*. A monoclonal antibody prepared against filamentous hemagglutinin (FHA) of *Bordetella pertussis* was found to recognize both of the high molecular weight proteins. This data suggests that the HMW and FHA proteins may serve similar biological functions. The derived amino acid sequences of the HMW1 and HMW2 proteins show sequence similarity to that for the FHA protein. It has further been shown that these antigenically-related proteins are produced by the majority of the non-typeable strains of Haemophilus. Angisera raised against the protein expressed by the HMW1 gene recognizes both the HMW2 protein and the *B. pertussis* FHA. The present invention includes an isolated and purified high molecular weight protein of non-typeable haemophilus which is antigenically related to the *B. pertussis* FHA, which may be obtained from natural sources or produced recombinantly.

A phage genomic library of a known strain of non-typeable Haemophilus was prepared by standard methods and the library was screened for clones expressing high molecular weight proteins, using a high titre antiserum against HMW's. A number of strongly reactive DNA clones were plaque-purified and sub-cloned into a T7 expression plasmid. It was found that they all expressed either one or the other of the two high-molecular-weight proteins designated HMW1 and HMW2, with apparent molecular weights of 125 and 120 kDa, respectively, encoded by open reading frames of 4.6 kb and 4.4 kb, respectively.

Representative clones expressing either HMW1 or HMW2 were further characterized and the genes isolated, purified and sequenced. The DNA sequence of HMW1 is shown in FIG. 1A–1C and the corresponding derived amino acid sequence in FIG. 2A–2B. Similarly, the DNA sequence of HMW2 is shown in FIG. 3A–3G and the corresponding derived amino acid sequence in FIG. 4A & 4B. Partial purification of the isolated proteins and N-terminal sequence analysis indicated that the expressed proteins are truncated since their sequence starts at residue number 442 of both full length HMW1 and HMW2 gene products.

Subcloning studies with respect to the hmw1 and hmw2 genes indicated that correct processing of the HMW proteins required the products of additional downstream genes. It has been found that both the hmw1 and hmw2 genes are flanked by two additional downstream open reading frames (ORFs), designated b and c, respectively, (see FIGS. 6A–6L and 7A–7L).

The b ORFs are 1635 bp in length, extending from nucleotides 5114 to 6748 in the case of hmw1 and nucleotides 5375 to 7009 in the case of hmw2, with their derived amino acid sequences 99% identical. The derived amino acid sequences demonstrate similarity with the derived amino acid sequences of two genes which encode proteins required for secretion and activation of hemolysins of *P. mirabilis* and *S. marcescens*.

The c ORFs are 1950 bp in length, extending from nucleotides 7062 to 9011 in the case of hmw1 and nucleotides 7249 to 9198 in the case of hmw2, with their derived amino acid sequences 96% identical. The hmw1 c ORF is preceded by a series of 9 bp direct tandem repeats. In plasmid subclones, interruption of the hmw1 b or c ORF results in defective processing and secretion of the hmw1 structural gene product.

The two high molecular weight proteins have been isolated and purified and shown to be partially protective against otitis media in chinchillas and to function as adhesins. These results indicate the potential for use of such high molecular proteins and structurally-related proteins of other non-typeable strains of *Haemophilus influenzae* as components in non-typeable *Haemophilus influenzae* vaccines.

Since the proteins provided herein are good cross-reactive antigens and are present in the majority of non-typeable Haemophilus strains, it is evident that these HMW proteins may become integral constituents of a universal Haemophilus vaccine. Indeed, these proteins may be used not only as protective antigens against otitis, sinusitis and bronchitis caused by the non-typeable Haemophilus strains, but also may be used as carriers for the protective Hib polysaccharides in a conjugate vaccine against meningitis. The proteins also may be used as carriers for other antigens, haptens and polysaccharides from other organisms, so as to induce immunity to such antigens, haptens and polysaccharides.

The nucleotide sequences encoding two high molecular weight proteins of a different non-typeable Haemophilus strain (designated HMW3 and HMW4) have been largely elucidated, and are presented in FIGS. 8A–8F and 9A–9F. HMW3 has an apparent molecular weight of 125 kDa while HMW4 has an apparent molecular weight of 123 kDa. These high molecular weight proteins are antigenically related to the HMW1 and HMW2 proteins and to FHA. Sequence analysis of HMW3 is approximately 85% complete and of HMW4 95% complete, with short stretches at the 5'-ends of each gene remaining to be sequenced.

FIG. 10A–10L contains a multiple sequence comparison of the derived amino acid sequences for the four high molecular weight proteins identified herein. As may be seen from this comparison, stretches of identical peptide sequence may be found throughout the length of the comparison, with HMW3 more closely resembling HMW1 and HMW4 more closely resembling HMW2. This information is highly suggestive of a considerable sequence homology between high molecular weight proteins from various non-typeable Haemophilus strains.

In addition, mutants of non-typeable *H. influenzae* strains that are deficient in expression of HMW1 or HMW2 or both have been constructed and examined for their capacity to adhere to cultured human epithelial cells. The hmw1 and hmw2 gene clusters have been expressed in *E. coli* and have been examined for in vitro adherence. The results of such experimentation demonstrate that both HMW1 and HMW2 mediate attachment and hence are adhesins and that this function is present even in the absence of other *H. influenzae* surface structures.

With the isolation and purification of the high molecular weight proteins, the inventors are able to determine the major protective epitopes by conventional epitope mapping and synthesize peptides corresponding to these determinants to be incorporated in fully synthetic or recombinant vaccines. Accordingly, the invention also comprises a synthetic peptide having an amino acid sequence corresponding to at least one protective epitope of a high molecular weight protein of a non-typeable *Haemophilus influenzae*. Such peptides are of varying length that constitute portions of the high-molecular-weight proteins, that can be used to induce immunity, either directly or as part of a conjugate, against the relative organisms and thus constitute vaccines for protection against the corresponding diseases.

The present invention also provides any variant or fragment of the proteins that retains the potential immunological ability to protect against disease caused by non-typeable Haemophilus strains. The variants may be constructed by partial deletions or mutations of the genes and expression of the resulting modified genes to give the protein variations.

EXAMPLES

Example 1

Non-typeable *H. influenzae* strains 5 and 12 were isolated in pure culture from the middle ear fluid of children with acute otitis media. Chromosomal DNA from strain 12, providing genes encoding proteins HMW1 and HMW2, was prepared by preparing Sau3A partial restriction digests of chromosomal DNA and fractionating on sucrose gradients. Fractions containing DNA fragments in the 9 to 20 kbp range were pooled and a library was prepared by ligation into λEMBL3 arms. Ligation mixtures were packaged in vitro and plate-amplified in a P2 lysogen of *E. coli* LE392.

For plasmid subcloning studies, DNA from a representative recombinant phage was subcloned into the T7 expression plasmid pT7-7, containing the T7 RNA polymerase promoter φ10, a ribosome-binding site and the translational start site for the T7 gene 10 protein upstream from a multiple cloning site (see FIG. 5B).

DNA sequence analysis was performed by the dideoxy method and both strands of the HMW1 gene and a single strand of the HMW2 gene were sequenced.

Western immunoblot analysis was performed to identify the recombinant proteins being produced by reactive phage clones. Phage lysates grown in LE392 cells or plaques picked directly from a lawn of LE392 cells on YT plates were solubilized in gel electrophoresis sample buffer prior to electrophoresis. Sodium dodecyl sulfate (SDS)-polyacrylamide gel electrophoresis was performed on 7.5% or 11% polyacrylamide modified Laemmli gels. After transfer of the proteins to nitrocellulose sheets, the sheets were probed sequentially with an E. coli-absorbed human serum sample containing high-titer antibody to the high-molecular-weight proteins and then with alkaline phosphatase-conjugated goat anti-human immunoglobulin G (IgG) second antibody. Sera from healthy adults contains high-titer antibody directed against surface-exposed high-molecular-weight proteins of non-typeable H. influenzae. One such serum sample was used as the screening antiserum after having been extensively absorbed with LE392 cells.

To identify recombinant proteins being produced by E. coli transformed with recombinant plasmids, the plasmids of interest were used to transform E. coli BL21 (DE3)/pLysS. The transformed strains were grown to an $A_{600}$ of 0.5 in L broth containing 50 μg of ampicillin per ml. IPTG was then added to 1 mM. One hour later, cells were harvested, and a sonicate of the cells was prepared. The protein concentrations of the samples were determined by the bicinchoninic acid method. Cell sonicates containing 100 μg of total protein were solubilized in electrophoresis sample buffer, subjected to SDS-polyacrylamide gel electrophoresis, and transferred to nitrocellulose. The nitrocellulose was then probed sequentially with the E. coli-absorbed adult serum sample and then with alkaline phosphatase-conjugated goat anti-human IgG second antibody.

Western immunoblot analysis also was performed to determine whether homologous and heterologous non-typeable H. influenzae strains expressed high-molecular-weight proteins antigenically related to the protein encoded by the cloned HMW1 gene (rHMW1). Cell sonicates of bacterial cells were solubilized in electrophoresis sample buffer, subjected to SDS-polyacrylamide gel electrophoresis, and transferred to nitrocellulose. Nitrocellulose was probed sequentially with polyclonal rabbit rHMW1 antiserum and then with alkaline phosphatase-conjugated goat anti-rabbit IgG second antibody.

Finally, Western immunoblot analysis was performed to determine whether non-typeable Haemophilus strains expressed proteins antigenically related to the filamentous hemagglutinin protein of Bordetella pertussis. Monoclonal antibody X3C, a murine immunoglobulin G (IgG) antibody which recognizes filamentous hemagglutinin, was used to probe cell sonicates by Western blot. An alkaline phosphatase-conjugated goat anti-mouse IgG second antibody was used for detection.

To generate recombinant protein antiserum, E. coli BL21(DE3)/pLysS was transformed with pHMW1-4, and expression of recombinant protein was induced with IPTG, as described above. A cell sonicate of the bacterial cells was prepared and separated into a supernatant and pellet fraction by centrifugation at 10,000×g for 30 min. The recombinant protein fractionated with the pellet fraction. A rabbit was subcutaneously immunized on biweekly schedule with 1 mg of protein from the pellet fraction, the first dose given with Freund's complete adjuvant and subsequent doses with Freund's incomplete adjuvant. Following the fourth injection, the rabbit was bled. Prior to use in the Western blot assay, the antiserum was absorbed extensively with sonicates of the host E. coli strain transformed with cloning vector alone.

To assess the sharing of antigenic determinants between HMW1 and filamentous hemagglutinin, enzyme-linked immunosorbent assay (ELISA) plates (Costar, Cambridge, Mass.) were coated with 60 μl of a 4-ug/ml solution of filamentous hemagglutinin in Dulbecco's phosphate-buffered saline per well for 2 h at room temperature. Wells were blocked for 1 h with 1% bovine serum albumin in Dulbecco's phosphate-buffered saline prior to addition of serum dilutions. rHMW1 antiserum was serially diluted in 0.1% Brij (Sigma, St. Louis, Mo.) in Dulbecco's phosphate-buffered saline and incubated for 3 h at room temperature. After being washed, the plates were incubated with peroxidase-conjugated goat anti-rabbit IgG antibody (Bio-Rad) for 2 h at room temperature and subsequently developed with 2,2'-azino-bis(3-ethylbenzthiazoline-6-sulfonic acid) (Sigma) at a concentration of 0.54 in mg/ml in 0.1M sodium citrate buffer, pH 4.2, containing 0.03% $H_2O_2$. Absorbances were read on an automated ELISA reader.

Recombinant phage expressing HMW1 or HMW2 were recovered as follows. The non-typeable H. influenzae strain 12, genomic library was screened for clones expressing high-molecular-weight proteins with an E. coli-absorbed human serum sample containing a high titer of antibodies directed against the high-molecular-weight proteins.

Numerous strongly reactive clones were identified along with more weakly reactive ones. Twenty strongly reactive clones were plaque-purified and examined by Western blot for expression of recombinant proteins. Each of the strongly reactive clones expressed one of two types of high-molecular-weight proteins, designated HMW1 and HMW2. The major immunoreactive protein bands in the HMW1 and HMW2 lysates migrated with apparent molecular masses of 125 and 120 kDa, respectively. In addition to the major bands, each lysate contained minor protein bands of higher apparent molecular weight. Protein bands seen in the HMW2 lysates at molecular masses of less than 120 kDa were not regularly observed and presumably represent proteolytic degradation products. Lysates of LE392 infected with the λEMBL3 cloning vector alone were non-reactive when immunologically screened with the same serum sample. Thus, the observed activity was not due to cross-reactive E. coli proteins or λEMBL3-encoded proteins. Furthermore, the recombinant proteins were not simply binding immunoglobulin nonspecifically, since the proteins were not reactive with the goat anti-human IgG conjugate alone, with normal rabbit sera, or with serum from a number of healthy young infants.

Representative clones expressing either the HMW1 or HMW2 recombinant proteins were characterized further. The restriction maps of the two phage types were different from each other, including the regions encoding the HMW1 and HMW2 structural genes. FIG. 5A shows restriction maps of representative recombinant phage which contained the HMW1 or HMW2 structural genes. The locations of the structural genes are indicated by the shaded bars.

HMW1 plasmid subclones were constructed by using the T7 expression plasmid T7-7 (FIG. 5A and B). HMW2 plasmid subclones also were constructed, and the results with these latter subclones were similar to those observed with the HMW1 constructs.

The approximate location and direction of transcription of the HMW1 structure gene were initially determined by using plasmid pHMW1 (FIG. 5A). This plasmid was constructed by inserting the 8.5-kb BamHI-SalI fragment from λHMW1 into BamHI- and SalI-cut pT7-7. E. coli transformed with pHMW1 expressed an immunoreactive recombinant protein with an apparent molecular mass of 115 kDa, which was strongly inducible with IPTG. This protein was significantly smaller than the 125-kDa major protein expressed by the parent phage, indicating that it either was being expressed as a fusion protein or was truncated at the carboxy terminus.

To more precisely localize the 3' end of the structural gene, additional plasmids were constructed with progressive deletions from the 3' end of the pHMW1 construct. Plasmid pHMW1-1 was constructed by digestion of pHMW1 with PstI, isolation of the resulting 8.8-kb fragment, and religation. Plasmid pHMW1-2 was constructed by digestion of pHMW1 with HindIII, isolation of the resulting 7.5-kb fragment, and religation. E. coli transformed with either plasmid pHMWi-1 or pHMW1-2 also expressed an immunoreactive recombinant protein with an apparent molecular mass of 115 kDa. These results indicated that the 3' end of the structural gene was 5' of the HindIII site.

To more precisely localize the 5' end of the gene, plasmids pHMW1-4 and pHMW1-7 were constructed. Plasmid pHMW1-4 was constructed by cloning the 5.1-kb BamHI-HindIII fragment from λHMW1 into a pT7-7-derived plasmid containing the upstream 3.8-kb EcoRI-BamHi fragment. E. coli transformed with pHMW1-4 expressed an immunoreactive protein with an apparent molecular mass of approximately 160 kDa. Although protein production was inducible with IPTG, the levels of protein production in these transformants were substantially lower than those with the pHMW1-2 transformants described above. Plasmid pHMW1-7 was constructed by digesting pHMW1-4 with NdeI and SpeI. The 9.0-kbp fragment generated by this double digestion was isolated, blunt ended, and religated. E. coli transformed with pHMW1-7 also expressed an immunoreactive protein with an apparent molecular mass of 160 kDa, a protein identical in size to that expressed by the pHMW1-4 transformants. The result indicated that the initiation codon for the HMW1 structural gene was 3' of the SpeI site. DNA sequence analysis confirmed this conclusion.

As noted above, the λHMW1 phage clones expressed a major immunoreactive band of 125 kDa, whereas the HMW1 plasmid clones pHMW1-4 and pHMW1-7, which contained what was believed to be the full-length gene, expressed an immunoreactive protein of approximately 160 kDa. This size discrepancy was disconcerting. One possible explanation was that an additional gene or genes necessary for correct processing of the HMW1 gene product were deleted in the process of subcloning. To address this possibility, plasmid pHMW1-14 was constructed. This construct was generated by digesting pHMW1 with NdeI and MluI and inserting the 7.6-kbp NdeI-MluI fragment isolated from pHMW1-4. Such a construct would contain the full-length HMW1 gene as well as the DNA 3' of the HMW1 gene which was present in the original HMW1 phage. E. coli transformed with this plasmid expressed major immunoreactive proteins with apparent molecular masses of 125 and 160 kDa as well as additional degradation products. The 125- and 160-kDa bands were identical to the major and minor immunoreactive bands detected in the HMW1 phage lysates. Interestingly, the pHMW1-14 construct also expressed significant amounts of protein in the uninduced condition, a situation not observed with the earlier constructs.

The relationship between the 125- and 160-kDa proteins remains somewhat unclear. Sequence analysis, described below, reveals that the HMW1 gene would be predicted to encode a protein of 159 kDa. It is believed that the 160-kDa protein is a precursor form of the mature 125-kDa protein, with the conversion from one protein to the other being dependent on the products of the two downstream genes.

Sequence analysis of the HMW1 gene (FIG. 1A–1G) revealed a 4,608-bp open reading frame (ORF), beginning with an ATG codon at nucleotide 351 and ending with a TAG stop codon at nucleotide 4959. A putative ribosome-binding site with the sequence AGGAG begins 10 bp upstream of the putative initiation codon. Five other in-frame ATG codons are located within 250 bp of the beginning of the ORF, but none of these is preceded by a typical ribosome-binding site. The 5'-flanking region of the ORF contains a series of direct tandem repeats, with the 7-bp sequence ATCTTTC repeated 16 times. These tandem repeats stop 100 bp 5' of the putative initiation codon. An 8-bp inverted repeat characteristic of a rho-independent transcriptional terminator is present, beginning at nucleotide 4983, 25 bp 3' of the presumed translational stop. Multiple termination codons are present in all three reading frames both upstream and downstream of the ORF. The derived amino acid sequence of the protein encoded by the HMW1 gene (FIG. 2A & 2B) has a molecular weight of 159,000, in good agreement with the apparent molecular weights of the proteins expressed by the HMW1-4 and HMW1-7 transformants. The derived amino acid sequence of the amino terminus does not demonstrate the characteristics of a typical signal sequence. The BamHI site used in generation of pHMW1 comprises bp 1743 through 1748 of the nucleotide sequence. The ORF downstream of the BamHI site would be predicted to encode a protein of 111 kDa, in good agreement with the 115 kDa estimated for the apparent molecular mass of the pHMW1-encoded fusion protein.

The sequence of the HMW2 gene (FIG. 3A–3G) consists of a 4,431-bp ORF, beginning with an ATG codon at nucleotide 352 and ending with a TAG stop codon at nucleotide 4783. The first 1,259 bp of the ORF of the HMW2 gene are identical to those of the HMW1 gene. Thereafter, the sequences begin to diverge but are 80% identical overall. With the exception of a single base addition at nucleotide 93 of the HMW2 sequence, the 5'-flanking regions of the HMW1 and HMW2 genes are identical for 310 bp upstream from the respective initiation codons. Thus, the HMW2 gene is preceded by the same set of tandem repeats and the same putative ribosome-binding site which lies 5' of the HMW1 gene. A putative transcriptional terminator identical to that identified 3' of the HMW1 ORF is noted, beginning at nucleotide 4804. The discrepancy in the lengths of the two genes is principally accounted for by a 186-bp gap in the HMW2 sequence, beginning at nucleotide position 3839. The derived amino acid sequence of the protein encoded by the HMW2 gene (FIG. 4A & 4B) has a molecular weight of 155,000 and is 71% identical with the derived amino acid sequence of the HMW1 gene.

The derived amino acid sequences of both the HMW1 and HMW2 genes (FIGS. 2A & 2B and 4A & 4B) demonstrated sequence similarity with the derived amino acid sequence of filamentous hemagglutinin of Bordetella pertussis, a surface-associated protein of this organism. The initial and optimized TFASTA scores for the HMW1-filamentous hemagglutinin sequence comparison were 87 and 186, respectively, with a word size of 2. The z score for the comparison was 45.8. The initial and optimized TFASTA scores for the HMW2-filamentous hemagglutinin sequence comparison were 68 and 196, respectively. The z score for the latter comparison was 48.7. The magnitudes of the initial and optimized TFASTA scores and the z scores suggested that a biologically significant relationship existed between the HMW1 and HMW2 gene products and filamentous hemagglutinin. When the derived amino acid sequences of HMW1, HMW2, and filamentous hemagglutinin genes were aligned and compared, the similarities were most notable at the amino-terminal ends of the three sequences. Twelve of the first 22 amino acids in the predicted peptide sequences were identical. In additional, the sequences demonstrated a common five-amino-acid stretch, Asn-Pro-Asn-Gly-Ile, and several shorter stretches of sequence identity within the first 200 amino acids.

EXAMPLE 2

To further explore the HMW1-filamentous hemagglutinin relationship, the ability of antiserum prepared against the HMW1-4 recombinant protein (rHMW1) to recognize purified filamentous hemagglutinin was assessed. The rHMW1 antiserum demonstrated ELISA reactivity with filamentous hemagglutinin in a dose-dependent manner. Preimmune rabbit serum had minimal reactivity in this assay. The rHMW1 antiserum also was examined in a Western blot assay and demonstrated weak but positive reactivity with purified filamentous hemagglutinin in this system also.

To identify the native Haemophilus protein corresponding to the HMW1 gene product and to determine the extent to which proteins antigenically related to the HMW1 cloned gene product were common among other non-typeable *H. influenzae* strains, a panel of Haemophilus strains was screened by Western blot with the rHMW1 antiserum. The antiserum recognized both a 125- and a 120-kDa protein band in the homologous strain 12, the putative mature protein products of the HMW1 and HMW2 genes, respectively.

When used to screen heterologous non-typeable *H. influenzae* strains, rHMW1 antiserum recognized high-molecular-weight proteins in 75% of 125 epidemiologically unrelated strains. In general, the antiserum reacted with one or two protein bands in the 100- to 150-kDa range in each of the heterologous strains in a pattern similar but not identical to that seen in the homologous strain.

Nonoclonal antibody X3C is a murine IgG antibody directed against the filamentous hemagglutinin protein of *B. pertussis*. This antibody can inhibit the binding of *B. pertussis* cells to Chinese hamster ovary cells and HeLa cells in culture and will inhibit hamagglutination of erythrocytes by purified filamentous hemagglutinin. A Western blot assay was performed in which this monoclonal antibody was screened against the same panel of non-typeable *H. influenzae* strains discussed above. Monoclonal antibody X3C recognized both the high-molecular-weight proteins in non-typeable *H. influenzae* strain 12 which were recognized by the recombinant-protein antiserum. In addition, the monoclonal antibody recognized protein bands in a subset of heterologous non-typeable *H. influenzas* strains which were identical to those recognized by the recombinant-protein antiserum. On occasion, the filamentous hemagglutinin monoclonal antibody appeared to recognize only one of the two bands which had been recognized by the recombinant-protein antiserum. Overall, monoclonal antibody X3C recognized high-molecular-weight protein bands identical to those recognized by the rHMW1 antiserum in approximately 35% of our collection of non-typeable *H. influenzae* strains.

EXAMPLE 3

Mutants deficient in expression of HMW1, MW2 or both proteins were constructed to examine the role of these proteins in bacterial adherence. The following strategy was employed. pHMW1-14 (see Example 1, FIG. 5A) was digested with BaMHI and then ligated to a kanamycin cassette isolated on a 1.3-kb BamH1 fragment from pUC4K. The resultant plasmid (pHMW1-17) was linearized by digestion with XbaI and transformed into non-typeable *H. influenzae* strain 12, followed by selection for kanamycin resistant colonies. Southern analysis of a series of these colonies demonstrated two populations of transformants, one with an insertion in the HMW1 structural gene and the other with an insertion in the HMW2 structural gene. One mutant from each of these classes was selected for further studies.

Mutants deficient in expression of both proteins were recovered using the following protocol. After deletion of the 2.1-kb fragment of DNA between two EcoRI sites spanning the 3'-portion of the HMW1 structural gene in pHMW-15, the kanamycin cassette from pUC4K was inserted as a 1.3-kb EcoR1 fragment. The resulting plasmid (pHMW1-16) was linearized by digestion with XbaI and transformed into strain 12, followed again by selection for kanamycin resistant colonies. Southern analysis of a representative sampling of these colonies demonstrated that in seven of eight cases, insertion into both the HMW1 and HMW2 loci had occurred. One such mutant was selected for further studies.

To confirm the intended phenotypes, the mutant strains were examined by Western blot analysis with a polyclonal antiserum against recombinant HMW1 protein. The parental strain expressed both the 125-kD HMW1 and the 120-kD HMW2 protein. In contrast, the HMW2 mutant failed to express the 120-kD protein, and the HMW1 mutant failed to express the 125-kD protein. The double mutant lacked expression of either protein. On the basis of whole cell lysates, outer membrane profiles, and colony morphology, the wild type strain and the mutants were otherwise identical with one another. Transmission electron microscopy demonstrated that none of the four strains expressed pili.

The capacity of wild type strain 12 to adhere to Chang epithelial cells was examined. In such assays, bacteria were inoculated into broth and allowed to grow to a density of $\sim 2 \times 10^9$ cfu/ml. Approximately $2 \times 10^7$ cfu were inoculated onto epithelial cell monolayers, and plates were gently centrifuged at 165× g for 5 minutes to facilitate contact between bacteria and the epithelial surface. After incubation for 30 minutes at 37° C. in 5% $CO_2$, monolayers were rinsed 5 times with PBS to remove nonadherent organisms and were treated with trypsin-EDTA (0.05% trypsin, 0.5% EDTA) in PBS to release them from the plastic support. Well contents were agitated, and dilutions were plated on solid medium to yield the number of adherent bacteria per monolayer. Percent adherence was calculated by dividing the number of adherent cfu per monolayer by the number of inoculated cfu.

As depicted in Table 1 below (the Tables appear at the end of the descriptive text), this strain adhered quite efficiently, with nearly 90% of the inoculum binding to the monolayer. Adherence by the mutant expressing HMW1 but not HMW2 (HMW2$^-$) was also quite efficient and comparable to that by the wild type strain. In contrast, attachment by the strain expressing HMW2 but deficient in expression of HMW1 (HMW1$^-$) was decreased about 15-fold relative to the wild type. Adherence by the double mutant (HMW1$^-$/HMW2$^-$) was decreased even further, approximately 50-fold compared with the wild type and approximately 3-fold compared with the HMW1 mutant. Considered together, these results suggest that both the HMW1 protein and the, HMW2 protein influence attachment to Chang epithelial cells. Interestingly, optimal adherence to this cell line appears to require HMW1 but not HMW2.

EXAMPLE 4

Using the plasmids pHMW1-16 and pHMW1-17 (see Example 3) and following a scheme similar to that employed with strain 12 as described in Example 3, three non-typeable Haemophilus strain 5 mutants were isolated, including one with the kanamycin gene inserted into the hmw1-like (designated hmw3) locus, a second with an insertion in the hmw2-like (designated hmw4) locus, and a third with insertions in both loci. As predicted, Western immunoblot analysis demonstrated that the mutant with insertion of the kanamycin cassette into the hmw1-like locus had lost expression of the HMW3 125-kD protein, while the mutant with insertion into the hmw2-like locus failed to express the HMW4 123-kD protein. The mutant with a double insertion was unable to express either of the high molecular weight proteins.

As shown in Table 1 below, wild type strain 5 demonstrated high level adherence, with almost 80% of the inoculum adhering per monolayer. Adherence by the mutant deficient in expression of the HMW2-like protein was also quite high. In contrast, adherence by the mutant unable to express the, HMW1-like protein was reduced about 5-fold relative to the wild type, and attachment by the double mutant was diminished even further (approximately 25-fold). Examination of Giemsa-stained samples confirmed these observations (not shown). Thus, the results with strain 5 corroborate the findings with strain 12 and the HMW1 and HMW2 proteins.

EXAMPLE 5

To confirm an adherence function for the HMW1 and HMW2 proteins and to examine the effect of HMW1 and HMW2 independently of other *H. influenzae* surface structures, the hmw1 and the hmw2 gene clusters were introduced into *E. coli* DH5α, using plasmids pHMW1-14 and pHMW2-21, respectively. As a control, the cloning vector, pT7-7, was also transformed into *E. coli* DH5α. Western blot analysis demonstrated that *E. coli* DH5α containing the hmw1 genes expressed a 125 kDa protein, while the same strain harboring the hmw2 genes expressed a 120-kDa protein. *E. coli* DH5α containing pT7-7 failed to react with antiserum against recombinant HMW1. Transmission electron microscopy revealed no pili or other surface appendages on any of the *E. coli* strains.

Adherence by the *E. coli* strains was quantitated and compared with adherence by wild type non-typeable *H. influenzae* strain 12. As shown in Table 2 below, adherence by *E. coli* DH5α containing vector alone was less than 1% of that for strain 12. In contrast, *E. coli* DH5α harboring the hmw1 gene cluster demonstrated adherence levels comparable to those for strain 12. Adherence by *E. coli* DH5α containing the hmw2 genes was approximately 6-fold lower than attachment by strain 12 but was increased 20-fold over adherence by *E. coli* DH5α with pT7-7 alone. These results indicate that the HMW1 and HMW2 proteins are capable of independently mediating attachment to Chang conjunctival cells. These results are consistent with the results with the *H. influenzae* mutants reported in Examples 3 and 4, providing further evidence that, with Chang epithelial cells, HMW1 is a more efficient adhesin than is HMW2.

Experiments with *E. coli* HB101 harboring pT7-7, pHMW1-14, or pHMW2-21 confirmed the results obtained with the DH5α derivatives (see Table 2).

EXAMPLE 6

HMW1 and HMW2 were isolated and purified from non-typeable *H. influenzae* (NTHI) strain 12 in the following manner. Non-typeable Haemophilus bacteria from frozen stock culture were streaked onto a chocolate plate and grown overnight at 37° C. in an incubator with 5% $CO_2$. 50 ml starter culture of brain heart infusion (BHI) broth, supplemented with 10 μg/ml each of hemin and AND was inoculated with growth on chocolate plate. The starter culture was grown until the optical density (O.D. –600 nm) reached 0.6 to 0.8 and then the bacteria in the starter culture was used to inoculate six 500 ml flasks of supplemented BHI using 8 to 10 ml per flask. The bacteria were grown in 500 ml flasks for an additional 5 to 6 hours at which time the O.D. was 1.5 or greater. Cultures were centrifuged at 10,000 rpm for 10 minutes.

Bacterial pellets were resuspended in a total volume of 250 ml of an extraction solution comprising 0.5M NaCl, 0.01M $Na_2EDTA$, 0.01M Tris 50 μM 1,10-phenanthroline, pH 7.5. The cells were not sonicated or otherwise disrupted. The resuspended cells were allowed to sit on ice at 0° C. for 60 minutes. The resuspended cells were centrifuged at 10,000 rpm for 10 minutes at 4° C. to remove the majority of intact cells and cellular debris. The supernatant was collected and centrifuged at 100,000 xg for 60 minutes at 4° C. The supernatant again was collected and dialyzed overnight at 4° C. against 0.01M sodium phosphate, pH 6.0.

The sample was centrifuged at 10,000 rpm for 10 minutes at 4° C. to remove insoluble debris precipitated from solution during dialysis. The supernatant was applied to a 10 ml CM Sepharose column which has been pre-equilibrated with 0.01M sodium phosphate, pH 6. Following application to this column, the column was washed with 0.01M sodium phosphate. Proteins were elevated from the column with a 0–0.5M KCl gradient in 0.01M Na phosphate, pH 6 and fractions were collected for gel examination. Coomassie gels of column fractions were carried out to identify those fractions containing high molecular weight proteins. The fractions containing high molecular weight proteins were pooled and concentrated to a 1 to 3 ml volume in preparation for application of sample to gel filtration column.

A Sepharose CL-4B gel filtration column was equilibrated with phosphate-buffered saline, pH 7.5. The concentrated high molecular weight protein sample was applied to the gel filtration column and column fractions were collected. Coomassie gels were performed on the column fractions to identify those containing high molecular weight proteins. The column fractions containing high molecular weight proteins were pooled.

The proteins were tested to determine whether they would protect against experimental otitis media caused by the homologous strain.

Chinchillas received three monthly subcutaneous injections with 40 μg of an HMW1–HMW2 protein mixture in Freund's adjuvant. One month after the last injection, the animals were challenged by intrabullar inoculation with 300 cfu of NTHI strain 12.

Infection developed in 5 of 5 control animals versus 5 of 10 immunized animals. Among infected animals, geometric mean bacterial counts in middle ear fluid 7 days postchallenge were $7.4 \times 10^6$ in control animals verus $1.3 \times 10^5$ in immunized animals.

Serum antibody titres following immunization were comparable in uninfected and infected animals. However, infection in immunized animals was uniformly associated with the appearance of bacteria down-regulated in expression of the HMW proteins, suggesting bacterial selection in response to immunologic pressure.

Although this data shows that protection following immunization was not complete, this data suggests the HMW adhesin proteins are potentially important protective antigens which may comprise one component of a multicomponent NTHI vaccine.

EXAMPLE 7

A number of synthetic peptides were derived from HMW1. Antisera then was raised to these peptides. The anti-peptide antisera to peptide HMW1-P5 was shown to recognize HMW1. Peptide HMW1-P5 covers amino acids 1453 to 1481 of HMW1, has the sequence VDEVIEAKRILEKVKDLSDEEREALAKLG (SEQ ID NO: 9), and represents bases 1498 to 1576 in FIG. 10A–10L.

This finding demonstrates that the DNA sequence and the derived protein is being interpreted in the correct reading frame and that peptides derived from the sequence can be produced which will be immunogenic.

SUMMARY OF DISCLOSURE

In summary of this disclosure, the present invention provides high molecular weight proteins of non-typeable Haemophilus, genes coding for the same and vaccines incorporating such proteins. Modifications are possible within the scope of this invention.

TABLE 1

Effect of mutation of high molecular weight proteins on adherence to Chang epithelial cells by nontypable *H. influenzae.*

| Strain | ADHERENCE* | |
|---|---|---|
| | % inoculum | relative to wild type[†] |
| Strain 12 derivatives | | |
| wild type | 87.7 ± 5.9 | 100.0 ± 6.7 |
| HMW1- mutant | 6.0 ± 0.9 | 6.8 ± 1.0 |

TABLE 1-continued

Effect of mutation of high molecular weight proteins on adherence to Chang epithelial cells by nontypable *H. influenzae.*

| Strain | ADHERENCE* | |
|---|---|---|
| | % inoculum | relative to wild type[†] |
| HMW2- mutant | 89.9 ± 10.8 | 102.5 ± 12.3 |
| HMW1-/HMW2- mutant | 2.0 ± 0.3 | 2.3 ± 0.3 |
| Strain 5 derivatives | | |
| wild type | 78.7 ± 3.2 | 100.0 ± 4.1 |
| HMW1-like mutant | 15.7 ± 2.6 | 19.9 ± 3.3 |
| HMW2-like mutant | 103.7 ± 14.0 | 131.7 ± 17.8 |
| double mutant | 3.5 ± 0.6 | 4.4 ± 0.8 |

*Numbers represent mean (± standard error of the mean) of measurements in triplicate or quadruplicate from representative experiments.
[†]Adherence values for strain 12 derivatives are relative to strain 12 wild type; values for strain 5 derivatives are relative to strain 5 wild type.

TABLE 2

Adherence by *E. coli* DH5α and HB101 harboring hmw1 or hmw2 gene clusters.

| Strain* | Adherence relative to *H. influenzae* strain 12[†] |
|---|---|
| DH5α (pT7-7) | 0.7 ± 0.02 |
| DH5α (pHMW1-14) | 114.2 ± 15.9 |
| DH5α (pHMW2-21) | 14.0 ± 3.7 |
| HB101 (pT7-7) | 1.2 ± 0.5 |
| HB101 (pHMW1-14) | 93.6 ± 15.8 |
| HB101 (pHMW2-21) | 3.6 ± 0.9 |

*The plasmid pHMW1-14 contains the hmw1 gene cluster, while pHMW2-21 contains the hmw2 gene cluster; pT7-7 is the cloning vector used in these constructs.
[†]Numbers represent the mean (± standard error of the mean) of measurements made in triplicate from representative experiments.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
    ( A ) LENGTH: 5116 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

```
ACAGCGTTCT  CTTAATACTA  GTACAAACCC  ACAATAAAAT  ATGACAAACA  ACAATTACAA      60

CACCTTTTTT  GCAGTCTATA  TGCAAATATT  TTAAAAAATA  GTATAAATCC  GCCATATAAA     120

ATGGTATAAT  CTTTCATCTT  TCATCTTTCA  TCTTTCATCT  TTCATCTTTC  ATCTTTCATC     180

TTTCATCTTT  CATCTTTCAT  CTTTCATCTT  TCATCTTTCA  TCTTTCATCT  TTCATCTTTC     240

ACATGCCCTG  ATGAACCGAG  GGAAGGGAGG  GAGGGGCAAG  AATGAAGAGG  GAGCTGAACG     300

AACGCAAATG  ATAAAGTAAT  TTAATTGTTC  AACTAACCTT  AGGAGAAAAT  ATGAACAAGC     360

TATATCGTCT  CAAATTCAGC  AAACGCCTGA  ATGCTTTGGT  TGCTGTGTCT  GAATTGGCAC     420
```

| | | | | | |
|---|---|---|---|---|---|
| GGGGTTGTGA | CCATTCCACA | GAAAAAGGCA | GCGAAAAACC | TGCTCGCATG | AAAGTGCGTC | 480 |
| ACTTAGCGTT | AAAGCCACTT | TCCGCTATGT | TACTATCTTT | AGGTGTAACA | TCTATTCCAC | 540 |
| AATCTGTTTT | AGCAAGCGGC | TTACAAGGAA | TGGATGTAGT | ACACGGCACA | GCCACTATGC | 600 |
| AAGTAGATGG | TAATAAAACC | ATTATCCGCA | ACAGTGTTGA | CGATATCATT | AATTGGAAAC | 660 |
| AATTTAACAT | CGACCAAAAT | GAATGGTGC | AGTTTTTACA | AGAAAACAAC | AACTCCGCCG | 720 |
| TATTCAACCG | TGTTACATCT | AACCAAATCT | CCCAATTAAA | AGGGATTTTA | GATTCTAACG | 780 |
| GACAAGTCTT | TTTAATCAAC | CCAAATGGTA | TCACAATAGG | TAAAGACGCA | ATTATTAACA | 840 |
| CTAATGGCTT | TACGGCTTCT | ACGCTAGACA | TTTCTAACGA | AAACATCAAG | GCGCGTAATT | 900 |
| TCACCTTCGA | GCAAACCAAA | GATAAAGCGC | TCGCTGAAAT | TGTGAATCAC | GGTTTAATTA | 960 |
| CTGTCGGTAA | AGACGGCAGT | GTAAATCTTA | TTGGTGGCAA | AGTGAAAAAC | GAGGGTGTGA | 1020 |
| TTAGCGTAAA | TGGTGGCAGC | ATTTCTTTAC | TCGCAGGGCA | AAAAATCACC | ATCAGCGATA | 1080 |
| TAATAAACCC | AACCATTACT | TACAGCATTG | CCGCGCCTGA | AAATGAAGCG | GTCAATCTGG | 1140 |
| GCGATATTTT | TGCCAAAGGC | GGTAACATTA | ATGTCCGTGC | TGCCACTATT | CGAAACCAAG | 1200 |
| GTAAACTTTC | TGCTGATTCT | GTAAGCAAAG | ATAAAGCGG | CAATATTGTT | CTTTCCGCCA | 1260 |
| AAGAGGGTGA | AGCGGAAATT | GGCGGTGTAA | TTTCCGCTCA | AAATCAGCAA | GCTAAAGGCG | 1320 |
| GCAAGCTGAT | GATTACAGGC | GATAAAGTCA | CATTAAAAAC | AGGTGCAGTT | ATCGACCTTT | 1380 |
| CAGGTAAAGA | AGGGGGAGAA | ACTTACCTTG | GCGGTGACGA | GCGCGGCGAA | GGTAAAAAGG | 1440 |
| GCATTCAATT | AGCAAAGAAA | ACCTCTTTAG | AAAAAGGCTC | AACCATCAAT | GTATCAGGCA | 1500 |
| AAGAAAAAGG | CGGACGCGCT | ATTGTGTGGG | GCGATATTGC | GTTAATTGAC | GGCAATATTA | 1560 |
| ACGCTCAAGG | TAGTGGTGAT | ATCGCTAAAA | CCGGTGGTTT | TGTGGAGACG | TCGGGGCATG | 1620 |
| ATTTATTCAT | CAAAGACAAT | GCAATTGTTG | ACGCCAAAGA | GTGGTTGTTA | GACCCGGATA | 1680 |
| ATGTATCTAT | TAATGCAGAA | ACAGCAGGAC | GCAGCAATAC | TTCAGAAGAC | GATGAATACA | 1740 |
| CGGGATCCGG | GAATAGTGCC | AGCACCCCAA | AACGAAACAA | AGAAAAGACA | ACATTAACAA | 1800 |
| ACACAACTCT | TGAGAGTATA | CTAAAAAAG | GTACCTTTGT | TAACATCACT | GCTAATCAAC | 1860 |
| GCATCTATGT | CAATAGCTCC | ATTAATTTAT | CCAATGGCAG | CTTAACTCTT | TGGAGTGAGG | 1920 |
| GTCGGAGCGG | TGGCGGCGTT | GAGATTAACA | ACGATATTAC | CACCGGTGAT | GATACCAGAG | 1980 |
| GTGCAAACTT | AACAATTTAC | TCAGGCGGCT | GGGTTGATGT | TCATAAAAAT | ATCTCACTCG | 2040 |
| GGGCGCAAGG | TAACATAAAC | ATTACAGCTA | AACAAGATAT | CGCCTTTGAG | AAAGGAAGCA | 2100 |
| ACCAAGTCAT | TACAGGTCAA | GGGACTATTA | CCTCAGGCAA | TCAAAAAGGT | TTTAGATTTA | 2160 |
| ATAATGTCTC | TCTAAACGGC | ACTGGCAGCG | GACTGCAATT | CACCACTAAA | AGAACCAATA | 2220 |
| AATACGCTAT | CACAAATAAA | TTTGAAGGGA | CTTTAAATAT | TTCAGGGAAA | GTGAACATCT | 2280 |
| CAATGGTTTT | ACCTAAAAAT | GAAAGTGGAT | ATGATAAATT | CAAAGGACGC | ACTTACTGGA | 2340 |
| ATTAACCTC | CTTAAATGTT | TCCGAGAGTG | GCGAGTTTAA | CCTCACTATT | GACTCCAGAG | 2400 |
| GAAGCGATAG | TGCAGGCACA | CTTACCCAGC | CTTATAATTT | AAACGGTATA | TCATTCAACA | 2460 |
| AAGACACTAC | CTTTAATGTT | GAACGAAATG | CAAGAGTCAA | CTTTGACATC | AAGGCACCAA | 2520 |
| TAGGGATAAA | TAAGTATTCT | AGTTTGAATT | ACGCATCATT | TAATGGAAAC | ATTTCAGTTT | 2580 |
| CGGGAGGGGG | GAGTGTTGAT | TTCACACTTC | TCGCCTCATC | CTCTAACGTC | CAAACCCCCG | 2640 |
| GTGTAGTTAT | AAATTCTAAA | TACTTTAATG | TTTCAACAGG | GTCAAGTTTA | AGATTTAAAA | 2700 |
| CTTCAGGCTC | AACAAAAACT | GGCTTCTCAA | TAGAGAAAGA | TTTAACTTTA | AATGCCACCG | 2760 |
| GAGGCAACAT | AACACTTTTG | CAAGTTGAAG | GCACCGATGG | AATGATTGGT | AAAGGCATTG | 2820 |

```
TAGCCAAAAA AAACATAACC TTTGAAGGAG GTAACATCAC CTTTGGCTCC AGGAAAGCCG      2880
TAACAGAAAT CGAAGGCAAT GTTACTATCA ATAACAACGC TAACGTCACT CTTATCGGTT      2940
CGGATTTTGA CAACCATCAA AAACCTTTAA CTATTAAAAA AGATGTCATC ATTAATAGCG      3000
GCAACCTTAC CGCTGGAGGC AATATTGTCA ATATAGCCGG AAATCTTACC GTTGAAAGTA      3060
ACGCTAATTT CAAAGCTATC ACAAATTTCA CTTTTAATGT AGGCGGCTTG TTTGACAACA      3120
AAGGCAATTC AAATATTTCC ATTGCCAAAG GAGGGGCTCG CTTTAAAGAC ATTGATAATT      3180
CCAAGAATTT AAGCATCACC ACCAACTCCA GCTCCACTTA CCGCACTATT ATAAGCGGCA      3240
ATATAACCAA TAAAAACGGT GATTTAAATA TTACGAACGA AGGTAGTGAT ACTGAAATGC      3300
AAATTGGCGG CGATGTCTCG CAAAAGAAG GTAATCTCAC GATTTCTTCT GACAAAATCA       3360
ATATTACCAA ACAGATAACA ATCAAGGCAG GTGTTGATGG GGAGAATTCC GATTCAGACG      3420
CGACAAACAA TGCCAATCTA ACCATTAAAA CCAAGAATT GAATTAACG CAAGACCTAA        3480
ATATTTCAGG TTTCAATAAA GCAGAGATTA CAGCTAAAGA TGGTAGTGAT TTAACTATTG      3540
GTAACACCAA TAGTGCTGAT GGTACTAATG CCAAAAAGT AACCTTAAC CAGGTTAAAG        3600
ATTCAAAAAT CTCTGCTGAC GGTCACAAGG TGACACTACA CAGCAAAGTG GAAACATCCG      3660
GTAGTAATAA CAACACTGAA GATAGCAGTG ACAATAATGC CGGCTTAACT ATCGATGCAA      3720
AAAATGTAAC AGTAAACAAC AATATTACTT CTCACAAAGC AGTGAGCATC TCTGCGACAA      3780
GTGGAGAAAT TACCACTAAA ACAGGTACAA CCATTAACGC AACCACTGGT AACGTGGAGA      3840
TAACCGCTCA AACAGGTAGT ATCCTAGGTG GAATTGAGTC CAGCTCTGGC TCTGTAACAC      3900
TTACTGCAAC CGAGGGCGCT CTTGCTGTAA GCAATATTTC GGGCAACACC GTTACTGTTA      3960
CTGCAAATAG CGGTGCATTA ACCACTTTGG CAGGCTCTAC AATTAAAGGA ACCGAGAGTG      4020
TAACCACTTC AAGTCAATCA GGCGATATCG GCGGTACGAT TTCTGGTGGC ACAGTAGAGG      4080
TTAAAGCAAC CGAAAGTTTA ACCACTCAAT CCAATTCAAA AATTAAAGCA CAACAGGCG      4140
AGGCTAACGT AACAAGTGCA ACAGGTACAA TTGGTGGTAC GATTCCGGT AATACGGTAA       4200
ATGTTACGGC AAACGCTGGC GATTTAACAG TTGGGAATGG CGCAGAAATT AATGCGACAG      4260
AAGGAGCTGC AACCTTAACT ACATCATCGG GCAAATTAAC TACCGAAGCT AGTTCACACA      4320
TTACTTCAGC CAAGGGTCAG GTAAATCTTT CAGCTCAGGA TGGTAGCGTT GCAGGAAGTA      4380
TTAATGCCGC CAATGTGACA CTAAATACTA CAGGCACTTT AACTACCGTG AAGGGTTCAA      4440
ACATTAATGC AACCAGCGGT ACCTTGGTTA TTAACGCAAA AGACGCTGAG CTAAATGGCG      4500
CAGCATTGGG TAACCACACA GTGGTAAATG CAACCAACGC AAATGGCTCC GGCAGCGTAA      4560
TCGCGACAAC CTCAAGCAGA GTGAACATCA CTGGGGATTT AATCACAATA AATGGATTAA      4620
ATATCATTTC AAAAAACGGT ATAAACACCG TACTGTTAAA AGGCGTTAAA ATTGATGTGA      4680
AATACATTCA ACCGGGTATA GCAAGCGTAG ATGAAGTAAT TGAAGCGAAA CGCATCCTTG      4740
AGAAGGTAAA AGATTTATCT GATGAAGAAA GAGAAGCGTT AGCTAAACTT GGAGTAAGTG      4800
CTGTACGTTT TATTGAGCCA AATAATACAA TTACAGTCGA TACACAAAAT GAATTTGCAA      4860
CCAGACCATT AAGTCGAATA GTGATTTCTG AAGGCAGGGC GTGTTTCTCA AACAGTGATG      4920
GCGCGACGGT GTGCGTTAAT ATCGCTGATA ACGGGCGGTA GCGGTCAGTA ATTGACAAGG      4980
TAGATTTCAT CCTGCAATGA AGTCATTTTA TTTTCGTATT ATTTACTGTG TGGGTTAAAG      5040
TTCAGTACGG GCTTTACCCA TCTTGTAAAA AATTACGGAG AATACAATAA AGTATTTTA       5100
ACAGGTTATT ATTATG                                                      5116
```

( 2 ) INFORMATION FOR SEQ ID NO:2:

( i ) SEQUENCE CHARACTERISTICS:
        ( A ) LENGTH: 1536 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
Met Asn Lys Ile Tyr Arg Leu Lys Phe Ser Lys Arg Leu Asn Ala Leu
 1               5                  10                  15

Val Ala Val Ser Glu Leu Ala Arg Gly Cys Asp His Ser Thr Glu Lys
            20                  25                  30

Gly Ser Glu Lys Pro Ala Arg Met Lys Val Arg His Leu Ala Leu Lys
        35                  40                  45

Pro Leu Ser Ala Met Leu Leu Ser Leu Gly Val Thr Ser Ile Pro Gln
    50                  55                  60

Ser Val Leu Ala Ser Gly Leu Gln Gly Met Asp Val Val His Gly Thr
65                  70                  75                  80

Ala Thr Met Gln Val Asp Gly Asn Lys Thr Ile Ile Arg Asn Ser Val
                85                  90                  95

Asp Ala Ile Ile Asn Trp Lys Gln Phe Asn Ile Asp Gln Asn Glu Met
            100                 105                 110

Val Gln Phe Leu Gln Glu Asn Asn Ser Ala Val Phe Asn Arg Val
        115                 120                 125

Thr Ser Asn Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Val Asn Leu Gly Asp Ile Phe Ala Lys Gly Gly Asn
            260                 265                 270

Ile Asn Val Arg Ala Ala Thr Ile Arg Asn Gln Gly Lys Leu Ser Ala
        275                 280                 285

Asp Ser Val Ser Lys Asp Lys Ser Gly Asn Ile Val Leu Ser Ala Lys
    290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
            340                 345                 350

Leu Gly Gly Asp Glu Arg Gly Glu Gly Lys Asn Gly Ile Gln Leu Ala
        355                 360                 365
```

```
Lys  Lys  Thr  Ser  Leu  Glu  Lys  Gly  Ser  Thr  Ile  Asn  Val  Ser  Gly  Lys
     370                      375                 380

Glu  Lys  Gly  Gly  Arg  Ala  Ile  Val  Trp  Gly  Asp  Ile  Ala  Leu  Ile  Asp
385                      390                 395                                400

Gly  Asn  Ile  Asn  Ala  Gln  Gly  Ser  Gly  Asp  Ile  Ala  Lys  Thr  Gly  Gly
                405                      410                      415

Phe  Val  Glu  Thr  Ser  Gly  His  Asp  Leu  Phe  Ile  Lys  Asp  Asn  Ala  Ile
               420                 425                      430

Val  Asp  Ala  Lys  Glu  Trp  Leu  Leu  Asp  Phe  Asp  Asn  Val  Ser  Ile  Asn
          435                 440                      445

Ala  Glu  Thr  Ala  Gly  Arg  Ser  Asn  Thr  Ser  Glu  Asp  Asp  Glu  Tyr  Thr
     450                      455                 460

Gly  Ser  Gly  Asn  Ser  Ala  Ser  Thr  Pro  Lys  Arg  Asn  Lys  Glu  Lys  Thr
465                      470                 475                           480

Thr  Leu  Thr  Asn  Thr  Thr  Leu  Glu  Ser  Ile  Leu  Lys  Lys  Gly  Thr  Phe
               485                      490                      495

Val  Asn  Ile  Thr  Ala  Asn  Gln  Arg  Ile  Tyr  Val  Asn  Ser  Ser  Ile  Asn
               500                 505                      510

Leu  Ser  Asn  Gly  Ser  Leu  Thr  Leu  Trp  Ser  Glu  Gly  Arg  Ser  Gly  Gly
          515                 520                 525

Gly  Val  Glu  Ile  Asn  Asn  Asp  Ile  Thr  Thr  Gly  Asp  Asp  Thr  Arg  Gly
     530                 535                      540

Ala  Asn  Leu  Thr  Ile  Tyr  Ser  Gly  Gly  Trp  Val  Asp  Val  His  Lys  Asn
545                      550                 555                           560

Ile  Ser  Leu  Gly  Ala  Gln  Gly  Asn  Ile  Asn  Ile  Thr  Ala  Lys  Gln  Asp
                565                      570                      575

Ile  Ala  Phe  Glu  Lys  Gly  Ser  Asn  Gln  Val  Ile  Thr  Gly  Gln  Gly  Thr
               580                 585                      590

Ile  Thr  Ser  Gly  Asn  Gln  Lys  Gly  Phe  Arg  Phe  Asn  Asn  Val  Ser  Leu
          595                 600                      605

Asn  Gly  Thr  Gly  Ser  Gly  Leu  Gln  Phe  Thr  Thr  Lys  Arg  Thr  Asn  Lys
     610                 615                      620

Tyr  Ala  Ile  Thr  Asn  Lys  Phe  Glu  Gly  Thr  Leu  Asn  Ile  Ser  Gly  Lys
625                      630                 635                           640

Val  Asn  Ile  Ser  Met  Val  Leu  Pro  Lys  Asn  Glu  Ser  Gly  Tyr  Asp  Lys
               645                 650                      655

Phe  Lys  Gly  Arg  Thr  Tyr  Trp  Asn  Leu  Thr  Ser  Leu  Asn  Val  Ser  Glu
               660                 665                      670

Ser  Gly  Glu  Phe  Asn  Leu  Thr  Ile  Asp  Ser  Arg  Gly  Ser  Asp  Ser  Ala
          675                 680                 685

Gly  Thr  Leu  Thr  Gln  Pro  Tyr  Asn  Leu  Asn  Gly  Ile  Ser  Phe  Asn  Lys
     690                 695                      700

Asp  Thr  Thr  Phe  Asn  Val  Glu  Arg  Asn  Ala  Arg  Val  Asn  Phe  Asp  Ile
705                      710                 715                           720

Lys  Ala  Pro  Ile  Gly  Ile  Asn  Lys  Tyr  Ser  Ser  Leu  Asn  Tyr  Ala  Ser
               725                 730                      735

Phe  Asn  Gly  Asn  Ile  Ser  Val  Ser  Gly  Gly  Gly  Ser  Val  Asp  Phe  Thr
               740                 745                      750

Leu  Leu  Ala  Ser  Ser  Ser  Asn  Val  Gln  Thr  Pro  Gly  Val  Val  Ile  Asn
          755                 760                      765

Ser  Lys  Tyr  Phe  Asn  Val  Ser  Thr  Gly  Ser  Ser  Leu  Arg  Phe  Lys  Thr
     770                 775                      780

Ser  Gly  Ser  Thr  Lys  Thr  Gly  Phe  Ser  Ile  Glu  Lys  Asp  Leu  Thr  Leu
```

```
          785                     790                     795                     800
Asn  Ala  Thr  Gly  Gly  Asn  Ile  Thr  Leu  Leu  Gln  Val  Glu  Gly  Thr  Asp
                    805                     810                     815

Gly  Met  Ile  Gly  Lys  Gly  Ile  Val  Ala  Lys  Lys  Asn  Ile  Thr  Phe  Glu
                    820                     825                     830

Gly  Gly  Asn  Ile  Thr  Phe  Gly  Ser  Arg  Lys  Ala  Val  Thr  Glu  Ile  Glu
                    835                     840                     845

Gly  Asn  Val  Thr  Ile  Asn  Asn  Ala  Asn  Val  Thr  Leu  Ile  Gly  Ser
850                           855                     860

Asp  Phe  Asp  Asn  His  Gln  Lys  Pro  Leu  Thr  Ile  Lys  Lys  Asp  Val  Ile
865                      870                     875                          880

Ile  Asn  Ser  Gly  Asn  Leu  Thr  Ala  Gly  Gly  Asn  Ile  Val  Asn  Ile  Ala
                    885                     890                          895

Gly  Asn  Leu  Thr  Val  Glu  Ser  Asn  Ala  Asn  Phe  Lys  Ala  Ile  Thr  Asn
                    900                     905                     910

Phe  Thr  Phe  Asn  Val  Gly  Gly  Leu  Phe  Asp  Asn  Lys  Gly  Asn  Ser  Asn
                    915                     920                     925

Ile  Ser  Ile  Ala  Lys  Gly  Gly  Ala  Arg  Phe  Lys  Asp  Ile  Asp  Asn  Ser
                    930                     935                     940

Lys  Asn  Leu  Ser  Ile  Thr  Thr  Asn  Ser  Ser  Ser  Thr  Tyr  Arg  Thr  Ile
945                           950                     955                          960

Ile  Ser  Gly  Asn  Ile  Thr  Asn  Lys  Asn  Gly  Asp  Leu  Asn  Ile  Thr  Asn
                    965                     970                     975

Glu  Gly  Ser  Asp  Thr  Glu  Met  Gln  Ile  Gly  Gly  Asp  Val  Ser  Gln  Lys
                    980                     985                     990

Glu  Gly  Asn  Leu  Thr  Ile  Ser  Ser  Asp  Lys  Ile  Asn  Ile  Thr  Lys  Gln
                    995                     1000                    1005

Ile  Thr  Ile  Lys  Ala  Gly  Val  Asp  Gly  Glu  Asn  Ser  Asp  Ser  Asp  Ala
                    1010                    1015                    1020

Thr  Asn  Asn  Ala  Asn  Leu  Thr  Ile  Lys  Thr  Lys  Glu  Leu  Lys  Leu  Thr
1025                          1030                    1035                         1040

Gln  Asp  Leu  Asn  Ile  Ser  Gly  Phe  Asn  Lys  Ala  Glu  Ile  Thr  Ala  Lys
                    1045                    1050                    1055

Asp  Gly  Ser  Asp  Leu  Thr  Ile  Gly  Asn  Thr  Asn  Ser  Ala  Asp  Gly  Thr
                    1060                    1065                    1070

Asn  Ala  Lys  Lys  Val  Thr  Phe  Asn  Gln  Val  Lys  Asp  Ser  Lys  Ile  Ser
                    1075                    1080                    1085

Ala  Asp  Gly  His  Lys  Val  Thr  Leu  His  Ser  Lys  Val  Glu  Thr  Ser  Gly
                    1090                    1095                    1100

Ser  Asn  Asn  Asn  Thr  Glu  Asp  Ser  Ser  Asp  Asn  Asn  Ala  Gly  Leu  Thr
1105                          1110                    1115                         1120

Ile  Asp  Ala  Lys  Asn  Val  Thr  Val  Asn  Asn  Ile  Thr  Ser  His  Lys
                    1125                    1130                    1135

Ala  Val  Ser  Ile  Ser  Ala  Thr  Ser  Gly  Glu  Ile  Thr  Thr  Lys  Thr  Gly
                    1140                    1145                    1150

Thr  Thr  Ile  Asn  Ala  Thr  Thr  Gly  Asn  Val  Glu  Ile  Thr  Ala  Gln  Thr
                    1155                    1160                    1165

Gly  Ser  Ile  Leu  Gly  Gly  Ile  Glu  Ser  Ser  Ser  Gly  Ser  Val  Thr  Leu
                    1170                    1175                    1180

Thr  Ala  Thr  Glu  Gly  Ala  Leu  Ala  Val  Ser  Asn  Ile  Ser  Gly  Asn  Thr
1185                          1190                    1195                         1200

Val  Thr  Val  Thr  Ala  Asn  Ser  Gly  Ala  Leu  Thr  Thr  Leu  Ala  Gly  Ser
                    1205                    1210                    1215
```

| | | | | | | | | | | | | | | |
|---|---|---|---|---|---|---|---|---|---|---|---|---|---|---|
|Thr|Ile|Lys|Gly|Thr|Glu|Ser|Val|Thr|Thr|Ser|Ser|Gln|Ser|Gly|Asp|
| | | |1220| | |1225| | | |1230| | | | |
|Ile|Gly|Gly|Thr|Ile|Ser|Gly|Gly|Thr|Val|Glu|Val|Lys|Ala|Thr|Glu|
| | | |1235| | |1240| | | |1245| | | | |
|Ser|Leu|Thr|Thr|Gln|Ser|Asn|Ser|Lys|Ile|Lys|Ala|Thr|Thr|Gly|Glu|
|1250| | | | |1255| | | |1260| | | | | |
|Ala|Asn|Val|Thr|Ser|Ala|Thr|Gly|Thr|Ile|Gly|Gly|Thr|Ile|Ser|Gly|
|1265| | | |1270| | | |1275| | | | | |1280|
|Asn|Thr|Val|Asn|Val|Thr|Ala|Asn|Ala|Gly|Asp|Leu|Thr|Val|Gly|Asn|
| | | | |1285| | | |1290| | | | |1295| |
|Gly|Ala|Glu|Ile|Asn|Ala|Thr|Glu|Gly|Ala|Ala|Thr|Leu|Thr|Thr|Ser|
| | | |1300| | | |1305| | | | |1310| | |
|Ser|Gly|Lys|Leu|Thr|Thr|Glu|Ala|Ser|Ser|His|Ile|Thr|Ser|Ala|Lys|
| | |1315| | | |1320| | | |1325| | | | |
|Gly|Gln|Val|Asn|Leu|Ser|Ala|Gln|Asp|Gly|Ser|Val|Ala|Gly|Ser|Ile|
| |1330| | | | |1335| | | |1340| | | | |
|Asn|Ala|Ala|Asn|Val|Thr|Leu|Asn|Thr|Thr|Gly|Thr|Leu|Thr|Thr|Val|
|1345| | | | |1350| | | |1355| | | | |1360|
|Lys|Gly|Ser|Asn|Ile|Asn|Ala|Thr|Ser|Gly|Thr|Leu|Val|Ile|Asn|Ala|
| | | |1365| | | |1370| | | | |1375| | |
|Lys|Asp|Ala|Glu|Leu|Asn|Gly|Ala|Ala|Leu|Gly|Asn|His|Thr|Val|Val|
| | | |1380| | | |1385| | | |1390| | | |
|Asn|Ala|Thr|Asn|Ala|Asn|Gly|Ser|Gly|Ser|Val|Ile|Ala|Thr|Thr|Ser|
| | |1395| | | | |1400| | | |1405| | | |
|Ser|Arg|Val|Asn|Ile|Thr|Gly|Asp|Leu|Ile|Thr|Ile|Asn|Gly|Leu|Asn|
| |1410| | | | |1415| | | |1420| | | | |
|Ile|Ile|Ser|Lys|Asn|Gly|Ile|Asn|Thr|Val|Leu|Leu|Lys|Gly|Val|Lys|
|1425| | | | |1430| | | |1435| | | | |1440|
|Ile|Asp|Val|Lys|Tyr|Ile|Gln|Pro|Gly|Ile|Ala|Ser|Val|Asp|Glu|Val|
| | | |1445| | | |1450| | | |1455| | | |
|Ile|Glu|Ala|Lys|Arg|Ile|Leu|Glu|Lys|Val|Lys|Asp|Leu|Ser|Asp|Glu|
| | | |1460| | | |1465| | | |1470| | | |
|Glu|Arg|Glu|Ala|Leu|Ala|Lys|Leu|Gly|Val|Ser|Ala|Val|Arg|Phe|Ile|
| |1475| | | | |1480| | | |1485| | | | |
|Glu|Pro|Asn|Asn|Thr|Ile|Thr|Val|Asp|Thr|Gln|Asn|Glu|Phe|Ala|Thr|
| |1490| | | | |1495| | | |1500| | | | |
|Arg|Pro|Leu|Ser|Arg|Ile|Val|Ile|Ser|Glu|Gly|Arg|Ala|Cys|Phe|Ser|
|1505| | | | |1510| | | |1515| | | | |1520|
|Asn|Ser|Asp|Gly|Ala|Thr|Val|Cys|Val|Asn|Ile|Ala|Asp|Asn|Gly|Arg|
| | | | |1525| | | |1530| | | | |1535| |

( 2 ) INFORMATION FOR SEQ ID NO:3:

( i ) SEQUENCE CHARACTERISTICS:
        ( A ) LENGTH: 4937 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
TAAATATACA AGATAATAAA AATAAATCAA GATTTTGTG ATGACAAACA ACAATTACAA        60
CACCTTTTTT GCAGTCTATA TGCAAATATT TTAAAAAAT AGTATAAATC CGCCATATAA       120
AATGGTATAA TCTTTCATCT TTCATCTTTA ATCTTTCATC TTTCATCTTT CATCTTTCAT      180
CTTTCATCTT TCATCTTTCA TCTTTCATCT TTCATCTTTC ATCTTTCATC TTTCATCTTT      240
```

```
CACATGAAAT  GATGAACCGA  GGGAAGGGAG  GGAGGGGCAA  GAATGAAGAG  GGAGCTGAAC     300
GAACGCAAAT  GATAAAGTAA  TTTAATTGTT  CAACTAACCT  TAGGAGAAAA  TATGAACAAG     360
ATATATCGTC  TCAAATTCAG  CAAACGCCTG  AATGCTTTGG  TTGCTGTGTC  TGAATTGGCA     420
CGGGGTTGTG  ACCATTCCAC  AGAAAAGGC   TTCCGCTATG  TTACTATCTT  TAGGTGTAAC     480
CACTTAGCGT  TAAAGCCACT  TTCCGCTATG  TTACTATCTT  TAGGTGTAAC  ATCTATTCCA     540
CAATCTGTTT  TAGCAAGCGG  CTTACAAGGA  ATGGATGTAG  TACACGGCAC  AGCCACTATG     600
CAAGTAGATG  GTAATAAAAC  CATTATCCGC  AACAGTGTTG  ACGCTATCAT  TAATTGGAAA     660
CAATTTAACA  TCGACCAAAA  TGAAATGGTG  CAGTTTTTAC  AAGAAAACAA  CAACTCCGCC     720
GTATTCAACC  GTGTTACATC  TAACCAAATC  TCCCAATTAA  AAGGGATTTT  AGATTCTAAC     780
GGACAAGTCT  TTTTAATCAA  CCCAAATGGT  ATCACAATAG  GTAAAGACGC  AATTATTAAC     840
ACTAATGGCT  TTACGGCTTC  TACGCTAGAC  ATTTCTAACG  AAAACATCAA  GGCGCGTAAT     900
TTCACCTTCG  AGCAAACCAA  AGATAAAGCG  CTCGCTGAAA  TTGTGAATCA  CGGTTTAATT     960
ACTGTCGGTA  AAGACGGCAG  TGTAAATCTT  ATTGGTGGCA  AAGTGAAAAA  CGAGGGTGTG    1020
ATTAGCGTAA  ATGGTGGCAG  CATTTCTTTA  CTCGCAGGGC  AAAAAATCAC  CATCAGCGAT    1080
ATAATAAACC  CAACCATTAC  TTACAGCATT  GCCGCGCCTG  AAAATGAAGC  GGTCAATCTG    1140
GGCGATATTT  TTGCCAAAGG  CGGTAACATT  AATGTCCGTG  CTGCCACTAT  TCGAAACCAA    1200
GGTAAACTTT  CTGCTGATTC  TGTAAGCAAA  GATAAAGCG   GCAATATTGT  TCTTTCCGCC    1260
AAAGAGGGTG  AAGCGGAAAT  TGGCGGTGTA  ATTTCCGCTC  AAAATCAGCA  AGCTAAAGGC    1320
GGCAAGCTGA  TGATTACAGG  CGATAAAGTC  ACATTAAAAA  CAGGTGCAGT  TATCGACCTT    1380
TCAGGTAAAG  AAGGGGGAGA  AACTTACCTT  GGCGGTGACG  AGCGCGGCGA  AGGTAAAAAC    1440
GGCATTCAAT  TAGCAAAGAA  AACCTCTTTA  GAAAAGGCT   CAACCATCAA  TGTATCAGGC    1500
AAAGAAAAG   GCGGACGCGC  TATTGTGTGG  GGCGATATTG  CGTTAATTGA  CGGCAATATT    1560
AACGCTCAAG  GTAGTGGTGA  TATCGCTAAA  ACCGGTGGTT  TTGTGGAGAC  ATCGGGGCAT    1620
TATTTATCCA  TTGACAGCAA  TGCAATTGTT  AAAACAAAAG  AGTGGTTGCT  AGACCCTGAT    1680
GATGTAACAA  TTGAAGCCGA  AGACCCCCTT  CGCAATAATA  CCGGTATAAA  TGATGAATTC    1740
CCAACAGGCA  CCGGTGAAGC  AAGCGACCCT  AAAAAAAATA  GCGAACTCAA  AACAACGCTA    1800
ACCAATACAA  CTATTTCAAA  TTATCTGAAA  AACGCCTGGA  CAATGAATAT  AACGGCATCA    1860
AGAAAACTTA  CCGTTAATAG  CTCAATCAAC  ATCGGAAGCA  ACTCCCACTT  AATTCTCCAT    1920
AGTAAAGGTC  AGCGTGGCGG  AGGCGTTCAG  ATTGATGGAG  ATATTACTTC  TAAAGGCGGA    1980
AATTTAACCA  TTTATTCTGG  CGGATGGGTT  GATGTTCATA  AAAATATTAC  GCTTGATCAG    2040
GGTTTTTTAA  ATATTACCGC  CGCTTCCGTA  GCTTTTGAAG  GTGGAAATAA  CAAAGCACGC    2100
GACGCGGCAA  ATGCTAAAAT  TGTCGCCCAG  GGCACTGTAA  CCATTACAGG  AGAGGGAAAA    2160
GATTTCAGGG  CTAACAACGT  ATCTTTAAAC  GGAACGGGTA  AAGGTCTGAA  TATCATTTCA    2220
TCAGTGAATA  ATTTAACCCA  CAATCTTAGT  GGCACAATTA  ACATATCTGG  GAATATAACA    2280
ATTAACCAAA  CTACGAGAAA  GAACACCTCG  TATTGGCAAA  CCAGCCATGA  TTCGCACTGG    2340
AACGTCAGTG  CTCTTAATCT  AGAGACAGGC  GCAAATTTTA  CCTTTATTAA  ATACATTTCA    2400
AGCAATAGCA  AAGGCTTAAC  AACACAGTAT  AGAAGCTCTG  CAGGGGTGAA  TTTTAACGGC    2460
GTAAATGGCA  ACATGTCATT  CAATCTCAAA  GAAGGAGCGA  AAGTTAATTT  CAAATTAAAA    2520
CCAAACGAGA  ACATGAACAC  AAGCAAACCT  TTACCAATTC  GGTTTTTAGC  CAATATCACA    2580
GCCACTGGTG  GGGGCTCTGT  TTTTTTTGAT  ATATATGCCA  ACCATTCTGG  CAGAGGGGCT    2640
```

```
GAGTTAAAAA TGAGTGAAAT TAATATCTCT AACGGCGCTA ATTTTACCTT AAATTCCCAT    2700
GTTCGCGGCG ATGACGCTTT TAAAATCAAC AAAGACTTAA CCATAAATGC AACCAATTCA    2760
AATTTCAGCC TCAGACAGAC GAAAGATGAT TTTTATGACG GGTACGCACG CAATGCCATC    2820
AATTCAACCT ACAACATATC CATTCTGGGC GGTAATGTCA CCCTTGGTGG ACAAAACTCA    2880
AGCAGCAGCA TTACGGGGAA TATTACTATC GAGAAAGCAG CAAATGTTAC GCTAGAAGCC    2940
AATAACGCCC CTAATCAGCA AACATAAGG  GATAGAGTTA TAAAACTTGG CAGCTTGCTC    3000
GTTAATGGGA GTTTAAGTTT AACTGGCGAA AATGCAGATA TTAAAGGCAA TCTCACTATT    3060
TCAGAAAGCG CCACTTTTAA AGGAAAGACT AGAGATACCC TAAATATCAC CGGCAATTTT    3120
ACCAATAATG GCACTGCCGA AATTAATATA ACACAAGGAG TGGTAAAACT TGGCAATGTT    3180
ACCAATGATG GTGATTTAAA CATTACCACT CACGCTAAAC GCAACCAAAG AAGCATCATC    3240
GGCGGAGATA TAATCAACAA AAAAGGAAGC TTAAATATTA CAGACAGTAA TAATGATGCT    3300
GAAATCCAAA TTGGCGGCAA TATCTCGCAA AAAGAAGGCA ACCTCACGAT TTCTTCCGAT    3360
AAAATTAATA TCACCAAACA GATAACAATC AAAAAGGGTA TTGATGGAGA GGACTCTAGT    3420
TCAGATGCGA CAAGTAATGC CAACCTAACT ATTAAAACCA AGAATTGAA  ATTGACAGAA    3480
GACCTAAGTA TTTCAGGTTT CAATAAAGCA GAGATTACAG CCAAAGATGG TAGAGATTTA    3540
ACTATTGGCA ACAGTAATGA CGGTAACAGC GGTGCCGAAG CCAAAACAGT AACTTTTAAC    3600
AATGTTAAAG ATTCAAAAAT CTCTGCTGAC GGTCACAATG TGACACTAAA TAGCAAAGTG    3660
AAAACATCTA GCAGCAATGG CGGACGTGAA AGCAATAGCG ACAACGATAC CGGCTTAACT    3720
ATTACTGCAA AAAATGTAGA AGTAAACAAA GATATTACTT CTCTCAAAAC AGTAAATATC    3780
ACCGCGTCGG AAAAGGTTAC CACCACAGCA GGCTCGACCA TTAACGCAAC AAATGGCAAA    3840
GCAAGTATTA CAACCAAAAC AGGTGATATC AGCGGTACGA TTTCCGGTAA CACGGTAAGT    3900
GTTAGCGCGA CTGGTGATTT AACCACTAAA TCCGGCTCAA AAATTGAAGC GAAATCGGGT    3960
GAGGCTAATG TAACAAGTGC AACAGGTACA ATTGGCGGTA CAATTTCCGG TAATACGGTA    4020
AATGTTACGG CAAACGCTGG CGATTTAACA GTTGGGAATG GCGCAGAAAT TAATGCGACA    4080
GAAGGAGCTG CAACCTTAAC CGCAACAGGG AATACCTTGA CTACTGAAGC CGGTTCTAGC    4140
ATCACTTCAA CTAAGGGTCA GGTAGACCTC TTGGCTCAGA ATGGTAGCAT CGCAGGAAGC    4200
ATTAATGCTG CTAATGTGAC ATTAAATACT ACAGGCACCT TAACCACCGT GGCAGGCTCG    4260
GATATTAAAG CAACCAGCGG CACCTTGGTT ATTAACGCAA AAGATGCTAA GCTAAATGGT    4320
GATGCATCAG GTGATAGTAC AGAAGTGAAT GCAGTCAACG CAAGCGGCTC TGGTAGTGTG    4380
ACTGCGGCAA CCTCAAGCAG TGTGAATATC ACTGGGGATT TAAACACAGT AAATGGGTTA    4440
AATATCATTT CGAAAGATGG TAGAAACACT GTGCGCTTAA GAGGCAAGGA AATTGAGGTG    4500
AAATATATCC AGCCAGGTGT AGCAAGTGTA GAAGAAGTAA TTGAAGCGAA ACGCGTCCTT    4560
GAAAAAGTAA AAGATTTATC TGATGAAGAA AGAGAAACAT TAGCTAAACT TGGTGTAAGT    4620
GCTGTACGTT TTGTTGAGCC AAATAATACA ATTACAGTCA ATACACAAAA TGAATTTACA    4680
ACCAGACCGT CAAGTCAAGT GATAATTTCT GAAGGTAAGG CGTGTTTCTC AAGTGGTAAT    4740
GGCGCACGAG TATGTACCAA TGTTGCTGAC GATGGACAGC CGTAGTCAGT AATTGACAAG    4800
GTAGATTTCA TCCTGCAATG AAGTCATTTT ATTTCGTAT  TATTTACTGT GTGGGTTAAA    4860
GTTCAGTACG GGCTTTACCC ATCTTGTAAA AAATTACGGA GAATACAATA AAGTATTTTT    4920
AACAGGTTAT TATTATG                                                  4937
```

-continued ( 2 ) INFORMATION FOR SEQ ID NO:4:

( i ) SEQUENCE CHARACTERISTICS:
      ( A ) LENGTH: 1477 amino acids
      ( B ) TYPE: amino acid
      ( C ) STRANDEDNESS: single
      ( D ) TOPOLOGY: linear ( x i ) SEQUENCE DESCRIPTION: SEQ ID NO:4:

```
Met Asn Lys Ile Tyr Arg Leu Lys Phe Ser Lys Arg Leu Asn Ala Leu
 1               5                  10                  15

Val Ala Val Ser Glu Leu Ala Arg Gly Cys Asp His Ser Thr Glu Lys
            20                  25                  30

Gly Ser Glu Lys Pro Ala Arg Met Lys Val Arg His Leu Ala Leu Lys
        35                  40                  45

Pro Leu Ser Ala Met Leu Leu Ser Leu Gly Val Thr Ser Ile Pro Gln
    50                  55                  60

Ser Val Leu Ala Ser Gly Leu Gln Gly Met Asp Val Val His Gly Thr
65                  70                  75                  80

Ala Thr Met Gln Val Asp Gly Asn Lys Thr Ile Ile Arg Asn Ser Val
                85                  90                  95

Asp Ala Ile Ile Asn Trp Lys Gln Phe Asn Ile Asp Gln Asn Glu Met
            100                 105                 110

Val Gln Phe Leu Gln Glu Asn Asn Asn Ser Ala Val Phe Asn Arg Val
        115                 120                 125

Thr Ser Asn Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Val Asn Leu Gly Asp Ile Phe Ala Lys Gly Gly Asn
            260                 265                 270

Ile Asn Val Arg Ala Ala Thr Ile Arg Asn Gln Gly Lys Leu Ser Ala
        275                 280                 285

Asp Ser Val Ser Lys Asp Lys Ser Gly Asn Ile Val Leu Ser Ala Lys
    290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
            340                 345                 350

Leu Gly Gly Asp Glu Arg Gly Glu Gly Lys Asn Gly Ile Gln Leu Ala
        355                 360                 365

Lys Lys Thr Ser Leu Glu Lys Gly Ser Thr Ile Asn Val Ser Gly Lys
```

|     | 370 |     |     |     | 375 |     |     |     | 380 |     |     |     |     |
| --- | --- | --- | --- | --- | --- | --- | --- | --- | --- | --- | --- | --- | --- |
| Glu | Lys | Gly | Gly | Phe | Ala | Ile | Val | Trp | Gly | Asp | Ile | Ala | Leu | Ile | Asp |
| 385 |     |     |     |     | 390 |     |     |     | 395 |     |     |     |     | 400 |
| Gly | Asn | Ile | Asn | Ala | Gln | Gly | Ser | Gly | Asp | Ile | Ala | Lys | Thr | Gly | Gly |
|     |     |     |     | 405 |     |     |     |     | 410 |     |     |     |     | 415 |     |
| Phe | Val | Glu | Thr | Ser | Gly | His | Asp | Leu | Phe | Ile | Lys | Asp | Asn | Ala | Ile |
|     |     |     | 420 |     |     |     |     | 425 |     |     |     |     | 430 |     |     |
| Val | Asp | Ala | Lys | Glu | Trp | Leu | Leu | Asp | Phe | Asp | Asn | Val | Ser | Ile | Asn |
|     |     |     | 435 |     |     |     | 440 |     |     |     |     | 445 |     |     |     |
| Ala | Glu | Asp | Pro | Leu | Phe | Asn | Asn | Thr | Gly | Ile | Asn | Asp | Glu | Phe | Pro |
|     | 450 |     |     |     |     | 455 |     |     |     |     | 460 |     |     |     |     |
| Thr | Gly | Thr | Gly | Glu | Ala | Ser | Asp | Pro | Lys | Lys | Asn | Ser | Glu | Leu | Lys |
| 465 |     |     |     |     | 470 |     |     |     |     | 475 |     |     |     |     | 480 |
| Thr | Thr | Leu | Thr | Asn | Thr | Thr | Ile | Ser | Asn | Tyr | Leu | Lys | Asn | Ala | Trp |
|     |     |     |     | 485 |     |     |     |     | 490 |     |     |     |     | 495 |     |
| Thr | Met | Asn | Ile | Thr | Ala | Ser | Arg | Lys | Leu | Thr | Val | Asn | Ser | Ser | Ile |
|     |     |     | 500 |     |     |     |     | 505 |     |     |     |     | 510 |     |     |
| Asn | Ile | Gly | Ser | Asn | Ser | His | Leu | Ile | Leu | His | Ser | Lys | Gly | Gln | Arg |
|     |     | 515 |     |     |     |     | 520 |     |     |     |     | 525 |     |     |     |
| Gly | Gly | Gly | Val | Gln | Ile | Asp | Gly | Asp | Ile | Thr | Ser | Lys | Gly | Gly | Asn |
|     | 530 |     |     |     |     | 535 |     |     |     |     | 540 |     |     |     |     |
| Leu | Thr | Ile | Tyr | Ser | Gly | Gly | Trp | Val | Asp | Val | His | Lys | Asn | Ile | Thr |
| 545 |     |     |     |     | 550 |     |     |     |     | 555 |     |     |     |     | 560 |
| Leu | Asp | Gln | Gly | Phe | Leu | Asn | Ile | Thr | Ala | Ala | Ser | Val | Ala | Phe | Glu |
|     |     |     |     | 565 |     |     |     |     | 570 |     |     |     |     | 575 |     |
| Gly | Gly | Asn | Asn | Lys | Ala | Arg | Asp | Ala | Ala | Asn | Ala | Lys | Ile | Val | Ala |
|     |     |     | 580 |     |     |     |     | 585 |     |     |     |     | 590 |     |     |
| Gln | Gly | Thr | Val | Thr | Ile | Thr | Gly | Glu | Gly | Lys | Asp | Phe | Arg | Ala | Asn |
|     |     | 595 |     |     |     |     | 600 |     |     |     |     | 605 |     |     |     |
| Asn | Val | Ser | Leu | Asn | Gly | Thr | Gly | Lys | Gly | Leu | Asn | Ile | Ile | Ser | Ser |
|     | 610 |     |     |     |     | 615 |     |     |     |     | 620 |     |     |     |     |
| Val | Asn | Asn | Leu | Thr | His | Asn | Leu | Ser | Gly | Thr | Ile | Asn | Ile | Ser | Gly |
| 625 |     |     |     |     | 630 |     |     |     |     | 635 |     |     |     |     | 640 |
| Asn | Ile | Thr | Ile | Asn | Gln | Thr | Thr | Arg | Lys | Asn | Thr | Ser | Tyr | Trp | Gln |
|     |     |     |     | 645 |     |     |     |     | 650 |     |     |     |     | 655 |     |
| Thr | Ser | His | Asp | Ser | His | Trp | Asn | Val | Ser | Ala | Leu | Asn | Leu | Glu | Thr |
|     |     |     | 660 |     |     |     |     | 665 |     |     |     |     | 670 |     |     |
| Gly | Ala | Asn | Phe | Thr | Phe | Ile | Lys | Tyr | Ile | Ser | Ser | Asn | Ser | Lys | Gly |
|     |     | 675 |     |     |     |     | 680 |     |     |     |     | 685 |     |     |     |
| Leu | Thr | Thr | Gln | Tyr | Arg | Ser | Ser | Ala | Gly | Val | Asn | Phe | Asn | Gly | Val |
|     | 690 |     |     |     |     | 695 |     |     |     |     | 700 |     |     |     |     |
| Asn | Gly | Asn | Met | Ser | Phe | Asn | Leu | Lys | Glu | Gly | Ala | Lys | Val | Asn | Phe |
| 705 |     |     |     |     | 710 |     |     |     |     | 715 |     |     |     |     | 720 |
| Lys | Leu | Lys | Pro | Asn | Glu | Asn | Met | Asn | Thr | Ser | Lys | Pro | Leu | Pro | Ile |
|     |     |     |     | 725 |     |     |     |     | 730 |     |     |     |     | 735 |     |
| Arg | Phe | Leu | Ala | Asn | Ile | Thr | Ala | Thr | Gly | Gly | Gly | Ser | Val | Phe | Phe |
|     |     |     | 740 |     |     |     |     | 745 |     |     |     |     | 750 |     |     |
| Asp | Ile | Tyr | Ala | Asn | His | Ser | Gly | Arg | Gly | Ala | Glu | Leu | Lys | Met | Ser |
|     |     | 755 |     |     |     |     | 760 |     |     |     |     | 765 |     |     |     |
| Glu | Ile | Asn | Ile | Ser | Asn | Gly | Ala | Asn | Phe | Thr | Leu | Asn | Ser | His | Val |
|     | 770 |     |     |     |     | 775 |     |     |     |     | 780 |     |     |     |     |
| Arg | Gly | Asp | Asp | Ala | Phe | Lys | Ile | Asn | Lys | Asp | Leu | Thr | Ile | Asn | Ala |
| 785 |     |     |     |     | 790 |     |     |     |     | 795 |     |     |     |     | 800 |

-continued

```
Thr Asn Ser Asn Phe Ser Leu Arg Gln Thr Lys Asp Asp Phe Tyr Asp
            805                 810                 815
Gly Tyr Ala Arg Asn Ala Ile Asn Ser Thr Tyr Asn Ile Ser Ile Leu
            820                 825                 830
Gly Gly Asn Val Thr Leu Gly Gly Gln Asn Ser Ser Ser Ser Ile Thr
            835                 840                 845
Gly Asn Ile Thr Ile Glu Lys Ala Ala Asn Val Thr Leu Glu Ala Asn
            850                 855                 860
Asn Ala Pro Asn Gln Gln Asn Ile Arg Asp Arg Val Ile Lys Leu Gly
865                 870                 875                 880
Ser Leu Leu Val Asn Gly Ser Leu Ser Leu Thr Gly Glu Asn Ala Asp
            885                 890                 895
Ile Lys Gly Asn Leu Thr Ile Ser Glu Ser Ala Thr Phe Lys Gly Lys
            900                 905                 910
Thr Arg Asp Thr Leu Asn Ile Thr Gly Asn Phe Thr Asn Asn Gly Thr
            915                 920                 925
Ala Glu Ile Asn Ile Thr Gln Gly Val Val Lys Leu Gly Asn Val Thr
            930                 935                 940
Asn Asp Gly Asp Leu Asn Ile Thr Thr His Ala Lys Arg Asn Gln Arg
945                 950                 955                 960
Ser Ile Ile Gly Gly Asp Ile Ile Asn Lys Lys Gly Ser Leu Asn Ile
            965                 970                 975
Thr Asp Ser Asn Asn Asp Ala Glu Ile Gln Ile Gly Gly Asn Ile Ser
            980                 985                 990
Gln Lys Glu Gly Asn Leu Thr Ile Ser Ser Asp Lys Ile Asn Ile Thr
            995                 1000                1005
Lys Gln Ile Thr Ile Lys Lys Gly Ile Asp Gly Glu Asp Ser Ser Ser
1010                1015                1020
Asp Ala Thr Ser Asn Ala Asn Leu Thr Ile Lys Thr Lys Glu Leu Lys
1025                1030                1035                1040
Leu Thr Glu Asp Leu Ser Ile Ser Gly Phe Asn Lys Ala Glu Ile Thr
            1045                1050                1055
Ala Lys Asp Gly Arg Asp Leu Thr Ile Gly Asn Ser Asn Asp Gly Asn
            1060                1065                1070
Ser Gly Ala Glu Ala Lys Thr Val Thr Phe Asn Asn Val Lys Asp Ser
            1075                1080                1085
Lys Ile Ser Ala Asp Gly His Asn Val Thr Leu Asn Ser Lys Val Lys
            1090                1095                1100
Thr Ser Ser Ser Asn Gly Gly Arg Glu Ser Asn Ser Asp Asn Asp Thr
1105                1110                1115                1120
Gly Leu Thr Ile Thr Ala Lys Asn Val Glu Val Asn Lys Asp Ile Thr
            1125                1130                1135
Ser Leu Lys Thr Val Asn Ile Thr Ala Ser Glu Lys Val Thr Thr Thr
            1140                1145                1150
Ala Gly Ser Thr Ile Asn Ala Thr Asn Gly Lys Ala Ser Ile Thr Thr
            1155                1160                1165
Lys Thr Gly Asp Ile Ser Gly Thr Ile Ser Gly Asn Thr Val Ser Val
            1170                1175                1180
Ser Ala Thr Val Asp Leu Thr Thr Lys Ser Gly Ser Lys Ile Glu Ala
1185                1190                1195                1200
Lys Ser Gly Glu Ala Asn Val Thr Ser Ala Thr Gly Thr Ile Gly Gly
            1205                1210                1215
Thr Ile Ser Gly Asn Thr Val Asn Val Thr Ala Asn Ala Gly Asp Leu
            1220                1225                1230
```

```
Thr Val Gly Asn Gly Ala Glu Ile Asn Ala Thr Glu Gly Ala Ala Thr
        1235                1240                1245

Leu Thr Ala Thr Gly Asn Thr Leu Thr Thr Glu Ala Gly Ser Ser Ile
        1250                1255                1260

Thr Ser Thr Lys Gly Gln Val Asp Leu Leu Ala Gln Asn Gly Ser Ile
1265            1270                1275                    1280

Ala Gly Ser Ile Asn Ala Ala Asn Val Thr Leu Asn Thr Thr Gly Thr
                1285                1290                1295

Leu Thr Thr Val Ala Gly Ser Asp Ile Lys Ala Thr Ser Gly Thr Leu
                1300            1305                1310

Val Ile Asn Ala Lys Asp Ala Lys Leu Asn Gly Asp Ala Ser Gly Asp
            1315                1320                1325

Ser Thr Glu Val Asn Ala Val Asn Ala Ser Gly Ser Gly Ser Val Thr
        1330                1335                1340

Ala Ala Thr Ser Ser Ser Val Asn Ile Thr Gly Asp Leu Asn Thr Val
1345                1350                1355                1360

Asn Gly Leu Asn Ile Ile Ser Lys Asp Gly Arg Asn Thr Val Arg Leu
                1365                1370                1375

Arg Gly Lys Glu Ile Glu Val Lys Tyr Ile Gln Pro Gly Val Ala Ser
            1380                1385                1390

Val Glu Glu Val Ile Glu Ala Lys Arg Val Leu Glu Lys Val Lys Asp
        1395                1400                1405

Leu Ser Asp Glu Glu Arg Glu Thr Leu Ala Lys Leu Gly Val Ser Ala
        1410                1415                1420

Val Arg Phe Val Glu Pro Asn Asn Thr Ile Thr Val Asn Thr Gln Asn
1425                1430                1435                1440

Glu Phe Thr Thr Arg Pro Ser Ser Gln Val Ile Ile Ser Glu Gly Lys
                1445                1450                1455

Ala Cys Phe Ser Ser Gly Asn Gly Ala Arg Val Cys Thr Asn Val Ala
                1460                1465                1470

Asp Asp Gly Gln Pro
            1475
```

( 2 ) INFORMATION FOR SEQ ID NO:5:

( i ) SEQUENCE CHARACTERISTICS:
    ( A ) LENGTH: 9171 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

```
ACAGCGTTCT CTTAATACTA GTACAAACCC ACAATAAAAT ATGACAAACA ACAATTACAA      60
CACCTTTTTT GCAGTCTATA TGCAAATATT TTAAAAATA  GTATAAATCC GCCATATAAA    120
ATGGTATAAT CTTTCATCTT TCATCTTTCA TCTTTCATCT TTCATCTTTC ATCTTTCATC    180
TTTCATCTTT CATCTTTCAT CTTTCATCTT TCATCTTTCA TCTTTCATCT TTCATCTTTC    240
ACATGAAATG ATGAACCGAG GGAAGGGAGG GAGGGGCAAG AATGAAGAGG GAGCTGAACG    300
AACGCAAATG ATAAAGTAAT TTAATTGTTC AACTAACCTT AGGAGAAAAT ATGAACAAGA    360
TATATCGTCT CAAATTCAGC AAACGCCTGA ATGCTTTGGT TGCTGTGTCT GAATTGGCAC    420
GGGGTTGTGA CCATTCCACA GAAAAAGGCA GCGAAAAACC TGCTCGCATG AAAGTGCGTC    480
ACTTAGCGTT AAAGCCACTT TCCGCTATGT TACTATCTTT AGGTGTAACA TCTATTCCAC    540
```

```
AATCTGTTTT AGCAAGCGGC TTACAAGGAA TGGATGTAGT ACACGGCACA GCCACTATGC    600
AAGTAGATGG TAATAAAACC ATTATCCGCA ACAGTGTTGA CGCTATCATT AATTGGAAAC    660
AATTTAACAT CGACCAAAAT GAAATGGTGC AGTTTTACA  AGAAAACAAC AACTCCGCCG    720
TATTCAACCG TGTTACATCT AACCAAATCT CCCAATTAAA AGGGATTTTA GATTCTAACG    780
GACAAGTCTT TTTAATCAAC CCAAATGGTA TCACAATAGG TAAAGACGCA ATTATTAACA    840
CTAATGGCTT TACGGCTTCT ACGCTAGACA TTTCTAACGA AACATCAAG  GCGCGTAATT    900
TCACCTTCGA GCAAACCAAA GATAAAGCGC TCGCTGAAAT TGTGAATCAC GGTTTAATTA    960
CTGTCGGTAA AGACGGCAGT GTAAATCTTA TTGGTGGCAA AGTGAAAAAC GAGGGTGTGA   1020
TTAGCGTAAA TGGTGGCAGC ATTTCTTTAC TCGCAGGGCA AAAAATCACC ATCAGCGATA   1080
TAATAAACCC AACCATTACT TACAGCATTG CCGCGCCTGA AAATGAAGCG GTCAATCTGG   1140
GCGATATTTT TGCCAAGGC  GGTAACATTA ATGTCCGTGC TGCCACTATT CGAAACCAAG   1200
CTTTCCGCCA AAGAGGGTGA AGCGGAAATT GGCGGTGTAA TTTCCGCTCA AAATCAGCAA   1260
GCTAAAGGCG GCAAGCTGAT GATTACAGGC GATAAAGTCA CATTAAAAAC AGGTGCAGTT   1320
ATCGACCTTT CAGGTAAAGA AGGGGGAGAA ACTTACCTTG GCGGTGACGA GCGCGGCGAA   1380
GGTAAAAACG GCATTCAATT AGCAAAGAAA ACCTCTTTAG AAAAAGGCTC AACCATCAAT   1440
GTATCAGGCA AAGAAAAGG  CGGACGCGCT ATTGTGTGGG GCGATATTGC GTTAATTGAC   1500
GGCAATATTA ACGCTCAAGG TAGTGGTGAT ATCGCTAAAA CCGGTGGTTT TGTGGAGACG   1560
TCGGGGCATG ATTTATTCAT CAAAGACAAT GCAATTGTTG ACGCCAAAGA GTGGTTGTTA   1620
GACCCGGATA ATGTATCTAT TAATGCAGAA ACAGCAGGAC GCAGCAATAC TTCAGAAGAC   1680
GATGAATACA CGGGATCCGG GAATAGTGCC AGCACCCCAA AACGAAACAA AGAAAAGACA   1740
ACATTAACAA ACACAACTCT TGAGAGTATA CTAAAAAAG  GTACCTTTGT TAACATCACT   1800
GCTAATCAAC GCATCTATGT CAATAGCTCC ATTAATTTAT CCAATGGCAG CTTAACTCTT   1860
TGGAGTGAGG GTCGGAGCGG TGGCGGCGTT GAGATTAACA ACGATATTAC CACCGGTGAT   1920
GATACCAGAG GTGCAAACTT AACAATTTAC TCAGGCGGCT GGGTTGATGT TCATAAAAAT   1980
ATCTCACTCG GGCGCAAGG  TAACATAAAC ATTACAGCTA ACAAGATAT  CGCCTTTGAG   2040
AAAGGAAGCA ACCAAGTCAT TACAGGTCAA GGGACTATTA CCTCAGGCAA TCAAAAAGGT   2100
TTTAGATTTA ATAATGTCTC TCTAAACGGC ACTGGCAGCG GACTGCAATT CACCACTAAA   2160
AGAACCAATA AATACGCTAT CACAAATAAA TTTGAAGGGA CTTTAAATAT TTCAGGGAAA   2220
GTGAACATCT CAATGGTTTT ACCTAAAAAT GAAAGTGGAT ATGATAAATT CAAAGGACGC   2280
ACTTACTGGA ATTTAACCTC GAAAGTGGAT ATGATAAATT CAAAGGACGC CCTCACTATT   2340
GACTCCAGAG GAAGCGATAG TGCAGGCACA CTTACCCAGC CTTATAATTT AAACGGTATA   2400
TCATTCAACA AAGACACTAC CTTTAATGTT GAACGAAATG CAAGAGTCAA CTTTGACATC   2460
AAGGCACCAA TAGGGATAAA TAAGTATTCT AGTTTGAATT ACGCATCATT TAATGGAAAC   2520
ATTTCAGTTT CGGGAGGGGG GAGTGTTGAT TTCACACTTC TCGCCTCATC CTCTAACGTC   2580
CAAACCCCCG GTGTAGTTAT AAATTCTAAA TACTTTAATG TTTCAACAGG GTCAAGTTTA   2640
AGATTTAAAA CTTCAGGCTC AACAAAAACT GGCTTCTCAA TAGAGAAAGA TTTAACTTTA   2700
AATGCCACCG GAGGCAACAT AACACTTTTG CAAGTTGAAG GCACCGATGG AATGATTGGT   2760
AAAGGCATTG TAGCCAAAAA AAACATAACC TTTGAAGGAG GTAAGATGAG GTTTGGCTCC   2820
AGGAAAGCCG TAACAGAAAT CGAAGGCAAT GTTACTATCA ATAACAACGC TAACGTCACT   2880
CTTATCGGTT CGGATTTTGA CAACCATCAA AAACCTTTAA CTATTAAAAA AGATGTCATC   2940
```

| | | | | | |
|---|---|---|---|---|---|
| ATTAATAGCG | GCAACCTTAC | CGCTGGAGGC | AATATTGTCA | ATATAGCCGG | AAATCTTACC | 3000
| GTTGAAAGTA | ACGCTAATTT | CAAAGCTATC | ACAAATTTCA | CTTTTAATGT | AGGCGGCTTG | 3060
| TTTGACAACA | AAGGCAATTC | AAATATTTCC | ATTGCCAAAG | GAGGGGCTCG | CTTTAAAGAC | 3120
| ATTGATAATT | CCAAGAATTT | AAGCATCACC | ACCAACTCCA | GCTCCACTTA | CCGCACTATT | 3180
| ATAAGCGGCA | ATATAACCAA | TAAAAACGGT | GATTTAAATA | TTACGAACGA | AGGTAGTGAT | 3240
| ACTGAAATGC | AAATTGGCGG | CGATGTCTCG | CAAAAGAAG | GTAATCTCAC | GATTTCTTCT | 3300
| GACAAAATCA | ATATTACCAA | ACAGATAACA | ATCAAGGCAG | GTGTTGATGG | GGAGAATTCC | 3360
| GATTCAGACG | CGACAAACAA | TGCCAATCTA | ACCATTAAAA | CCAAGAATT | GAAATTAACG | 3420
| CAAGACCTAA | ATATTTCAGG | TTTCAATAAA | GCAGAGATTA | CAGCTAAAGA | TGGTAGTGAT | 3480
| TTAACTATTG | GTAACACCAA | TAGTGCTGAT | GGTACTAATG | CCAAAAAGT | AACCTTTAAC | 3540
| CAGGTTAAAG | ATTCAAAAAT | CTCTGCTGAC | GGTCACAAGG | TGACACTACA | CAGCAAAGTG | 3600
| GAAACATCCG | GTAGTAATAA | CAACACTGAA | GATAGCAGTG | ACAATAATGC | CGGCTTAACT | 3660
| ATCGATGCAA | AAAATGTAAC | AGTAAACAAC | AATATTACTT | CTCACAAAGC | AGTGAGCATC | 3720
| TCTGCGACAA | GTGGAGAAAT | TACCACTAAA | ACAGGTACAA | CCATTAACGC | AACCACTGGT | 3780
| AACGTGGAGA | TAACCGCTCA | AACAGGTAGT | ATCCTAGGTG | GAATTGAGTC | CAGCTCTGGC | 3840
| TCTGTAACAC | TTACTGCAAC | CGAGGGCGCT | CTTGCTGTAA | GCAATATTTC | GGGCAACACC | 3900
| GTTACTGTTA | CTGCAAATAG | CGGTGCATTA | ACCACTTTGG | CAGGCTCTAC | AATTAAAGGA | 3960
| ACCGAGAGTG | TAACCACTTC | AAGTCAATCA | GGCGATATCG | GCGGTACGAT | TTCTGGTGGC | 4020
| ACAGTAGAGG | TTAAAGCAAC | CGAAAGTTTA | ACCACTCAAT | CCAATTCAAA | AATTAAAGCA | 4080
| ACAACAGGCG | AGGCTAACGT | AACAAGTGCA | ACAGGTACAA | TTGGTGGTAC | GATTTCCGGT | 4140
| AATACGGTAA | ATGTTACGGC | AAACGCTGGC | GATTTAACAG | TTGGGAATGG | CGCAGAAATT | 4200
| AATGCGACAG | AAGGAGCTGC | AACCTTAACT | ACATCATCGG | GCAAATTAAC | TACCGAAGCT | 4260
| AGTTCACACA | TTACTTCAGC | CAAGGGTCAG | GTAAATCTTT | CAGCTCAGGA | TGGTAGCGTT | 4320
| GCAGGAAGTA | TTAATGCCGC | CAATGTGACA | CTAAATACTA | CAGGCACTTT | AACTACCGTG | 4380
| AAGGGTTCAA | ACATTAATGC | AACCAGCGGT | ACCTTGGTTA | TTAACGCAAA | AGACGCTGAG | 4440
| CTAAATGGCG | CAGCATTGGG | TAACCACACA | GTGGTAAATG | CAACCAACGC | AAATGGCTCC | 4500
| GGCAGCGTAA | TCGCGACAAC | CTCAAGCAGA | GTGAACATCA | CTGGGGATTT | AATCACAATA | 4560
| AATGGATTAA | ATATCATTTC | AAAAAACGGT | ATAAACACCG | TACTGTTAAA | AGGCGTTAAA | 4620
| ATTGATGTGA | AATACATTCA | ACCGGGTATA | GCAAGCGTAG | ATGAAGTAAT | TGAAGCGAAA | 4680
| CGCATCCTTG | AGAAGGTAAA | AGATTTATCT | GATGAAGAAA | GAGAAGCGTT | AGCTAAACTT | 4740
| GGCGTAAGTG | CTGTACGTTT | TATTGAGCCA | AATAATACAA | TTACAGTCGA | TACACAAAAT | 4800
| GAATTTGCAA | CCAGACCATT | AAGTCGAATA | GTGATTTCTG | AAGGCAGGGC | GTGTTTCTCA | 4860
| AACAGTGATG | GCGCGACGGT | GTGCGTTAAT | ATCGCTGATA | ACGGGCGGTA | GCGGTCAGTA | 4920
| ATTGACAAGG | TAGATTTCAT | CCTGCAATGA | AGTCATTTTA | TTTTCGTATT | ATTTACTGTG | 4980
| TGGGTTAAAG | TTCAGTACGG | GCTTTACCCA | TCTTGTAAAA | AATTACGGAG | AATACAATAA | 5040
| AGTATTTTTA | ACAGGTTATT | ATTATGAAAA | ATATAAAAAG | CAGATTAAAA | CTCAGTGCAA | 5100
| TATCAGTATT | GCTTGGCCTG | GCTTCTTCAT | CATTGTATGC | AGAAGAAGCG | TTTTAGTAA | 5160
| AAGGCTTTCA | GTTATCTGGT | GCACTTGAAA | CTTTAAGTGA | AGACGCCCAA | CTGTCTGTAG | 5220
| CAAAATCTTT | ATCTAAATAC | CAAGGCTCGC | AAACTTTAAC | AAACCTAAAA | ACAGCACAGC | 5280
| TTGAATTACA | GGCTGTGCTA | GATAAGATTG | AGCCAAATAA | GTTTGATGTG | ATATTGCCAC | 5340

```
AACAAACCAT TACGGATGGC AATATTATGT TTGAGCTAGT CTCGAAATCA GCCGCAGAAA    5400
GCCAAGTTTT TTATAAGGCG AGCCAGGGTT ATAGTGAAGA AAATATCGCT CGTAGCCTGC    5460
CATCTTTGAA ACAAGGAAAA GTGTATGAAG ATGGTCGTCA GTGGTTCGAT TTGCGTGAAT    5520
TCAATATGGC AAAAGAAAAT CCACTTAAAG TCACTCGCGT GCATTACGAG TTAAACCCTA    5580
AAAACAAAAC CTCTGATTTG GTAGTTGCAG GTTTTTCGCC TTTTGGCAAA ACGCGTAGCT    5640
TTGTTTCCTA TGATAATTTC GGCGCAAGGG AGTTAACTA TCAACGTGTA AGTCTAGGTT     5700
TTGTAAATGC CAATTTGACC GGACATGATG ATGTATTAAA TCTAAACGCA TTGACCAATG    5760
TAAAAGCACC ATCAAAATCT TATGCGGTAG GCATAGGATA TACTTATCCG TTTTATGATA    5820
AACACCAATC CTTAAGTCTT TATACCAGCA TGAGTTATGC TGATTCTAAT GATATCGACG    5880
GCTTACCAAG TGCGATTAAT CGTAAATTAT CAAAGGTCA ATCTATCTCT GCGAATCTGA     5940
AATGGAGTTA TTATCTCCCG ACATTTAACC TTGGAATGGA AGACCAGTTT AAAATTAATT    6000
TAGGCTACAA CTACCGCCAT ATTAATCAAA CATCCGAGTT AAACACCCTG GGTGCAACGA    6060
AGAAAAAATT TGCAGTATCA GGCGTAAGTG CAGGCATTGA TGGACATATC CAATTTACCC    6120
CTAAAACAAT CTTTAATATT GATTAACTC ATCATTATTA CGCGAGTAAA TTACCAGGCT     6180
CTTTTGGAAT GGAGCGCATT GGCGAAACAT TTAATCGCAG CTATCACATT AGCACAGCCA    6240
GTTAGGGTT GAGTCAAGAG TTTGCTCAAG GTTGGCATTT TAGCAGTCAA TTATCGGGTC     6300
AGTTTACTCT ACAAGATATA AGTAGCATAG ATTTATTCTC TGTAACAGGT ACTTATGGCG    6360
TCAGAGGCTT TAAATACGGC GGTGCAAGTG GTGAGCGCGG TCTTGTATGG CGTAATGAAT    6420
TAAGTATGCC AAAATACACC CGCTTTCAAA TCAGCCCTTA TGCGTTTTAT GATGCAGGTC    6480
AGTTCCGTTA TAATAGCGAA AATGCTAAAA CTTACGGCGA AGATATGCAC ACGGTATCCT    6540
CTGCGGGTTT AGGCATTAAA ACCTCTCCTA CACAAAACTT AAGCTTAGAT GCTTTTGTTG    6600
CTCGTCGCTT TGCAAATGCC AATAGTGACA ATTTGAATGG CAACAAAAAA CGCACAAGCT    6660
CACCTACAAC CTTCTGGGGT AGATTAACAT TCAGTTTCTA ACCCTGAAAT TTAATCAACT    6720
GGTAAGCGTT CCGCCTACCA GTTATAACT ATATGCTTTA CCCGCCAATT TACAGTCTAT     6780
ACGCAACCCT GTTTTCATCC TTATATATCA AACAAACTAA GCAAACCAAG CAAACCAAGC    6840
AAACCAAGCA AACCAAGCAA ACCAAGCAAA CCAAGCAAAC CAAGCAAACC AAGCAAACCA    6900
AGCAAACCAA GCAAACCAAG CAAACCAAGC AAACCAAGCA ATGCTAAAAA ACAATTTATA    6960
TGATAAACTA AAACATACTC CATACCATGG CAATACAAGG GATTTAATAA TATGACAAAA    7020
GAAAATTTAC AAAGTGTTCC ACAAATACG ACCGCTCAC TTGTAGAATC AAACAACGAC      7080
CAAACTTCCC TGCAAATACT TAAACAACCA CCCAAACCCA ACCTATTACG CCTGGAACAA    7140
CATGTCGCCA AAAAGATTA TGAGCTTGCT TGCCGCGAAT TAATGGCGAT TTTGGAAAAA     7200
ATGGACGCTA ATTTTGGAGG CGTTCACGAT ATTGAATTTG ACGCACCTGC TCAGCTGGCA    7260
TATCTACCCG AAAAACTACT AATTCATTTT GCCACTCGTC TCGCTAATGC AATTACAACA    7320
CTCTTTTCCG ACCCCGAATT GGCAATTTCC GAAGAAGGGG CATTAAAGAT GATTAGCCTG    7380
CAACGCTGGT TGACGCTGAT TTTTGCCTCT TCCCCCTACG TTAACGCAGA CCATATTCTC    7440
AATAAATATA ATATCAACCC AGATTCCGAA GGTGGCTTTC ATTTAGCAAC AGACAACTCT    7500
TCTATTGCTA AATTCTGTAT TTTTTACTTA CCCGAATCCA ATGTCAATAT GAGTTTAGAT    7560
GCGTTATGGG CAGGGAATCA ACAACTTTGT GCTTCATTGT GTTTTGCGTT GCAGTCTTCA    7620
CGTTTTATTG GTACTGCATC TGCGTTTCAT AAAAGAGCGG TGGTTTTACA GTGGTTTCCT    7680
AAAAAACTCG CCGAAATTGC TAATTTAGAT GAATTGCCTG CAAATATCCT TCATGATGTA    7740
```

| | | | | | | |
|---|---|---|---|---|---|---|
| TATATGCACT | GCAGTTATGA | TTTAGCAAAA | AACAAGCACG | ATGTTAAGCG | TCCATTAAAC | 7800 |
| GAACTTGTCC | GCAAGCATAT | CCTCACGCAA | GGATGGCAAG | ACCGCTACCT | TTACACCTTA | 7860 |
| GGTAAAAAGG | ACGGCAAACC | TGTGATGATG | GTACTGCTTG | AACATTTTAA | TTCGGGACAT | 7920 |
| TCGATTTATC | GCACGCATTC | AACTTCAATG | ATTGCTGCTC | GAGAAAAATT | CTATTTAGTC | 7980 |
| GGCTTAGGCC | ATGAGGGCGT | TGATAACATA | GGTCGAGAAG | TGTTTGACGA | GTTCTTTGAA | 8040 |
| ATCAGTAGCA | ATAATATAAT | GGAGAGACTG | TTTTTATCC | GTAAACAGTG | CGAAACTTTC | 8100 |
| CAACCCGCAG | TGTTCTATAT | GCCAAGCATT | GGCATGGATA | TTACCACGAT | TTTTGTGAGC | 8160 |
| AACACTCGGC | TTGCCCCTAT | TCAAGCTGTA | GCCTTGGGTC | ATCCTGCCAC | TACGCATTCT | 8220 |
| GAATTTATTG | ATTATGTCAT | CGTAGAAGAT | GATTATGTGG | GCAGTGAAGA | TTGTTTTAGC | 8280 |
| GAAACCCTTT | TACGCTTACC | CAAAGATGCC | CTACCTTATG | TACCATCTGC | ACTCGCCCCA | 8340 |
| CAAAAGTGG | ATTATGTACT | CAGGGAAAAC | CCTGAAGTAG | TCAATATCGG | TATTGCCGCT | 8400 |
| ACCACAATGA | AATTAAACCC | TGAATTTTTG | CTAACATTGC | AAGAAATCAG | AGATAAAGCT | 8460 |
| AAAGTCAAAA | TACATTTTCA | TTTCGCACTT | GGACAATCAA | CAGGCTTGAC | ACACCCTTAT | 8520 |
| GTCAAATGGT | TTATCGAAAG | CTATTTAGGT | GACGATGCCA | CTGCACATCC | CCACGCACCT | 8580 |
| TATCACGATT | ATCTGGCAAT | ATTGCGTGAT | TGCGATATGC | TACTAAATCC | GTTTCCTTTC | 8640 |
| GGTAATACTA | ACGGCATAAT | TGATATGGTT | ACATTAGGTT | TAGTTGGTGT | ATGCAAAACG | 8700 |
| GGGGATGAAG | TACATGAACA | TATTGATGAA | GGTCTGTTTA | AACGCTTAGG | ACTACCAGAA | 8760 |
| TGGCTGATAG | CCGACACACG | AGAAACATAT | ATTGAATGTG | CTTTGCGTCT | AGCAGAAAAC | 8820 |
| CATCAAGAAC | GCCTTGAACT | CCGTCGTTAC | ATCATAGAAA | ACAACGGCTT | ACAAAAGCTT | 8880 |
| TTTACAGGCG | ACCCTCGTCC | ATTGGGCAAA | ATACTGCTTA | AGAAAACAAA | TGAATGGAAG | 8940 |
| CGGAAGCACT | TGAGTAAAAA | ATAACGGTTT | TTTAAAGTAA | AAGTGCGGTT | AATTTTCAAA | 9000 |
| GCGTTTTAAA | AACCTCTCAA | AAATCAACCG | CACTTTTATC | TTTATAACGC | TCCCGCGCGC | 9060 |
| TGACAGTTTA | TCTCTTTCTT | AAAATACCCA | TAAAATTGTG | GCAATAGTTG | GGTAATCAAA | 9120 |
| TTCAATTGTT | GATACGGCAA | ACTAAAGACG | GCGCGTTCTT | CGGCAGTCAT | C | 9171 |

( 2 ) INFORMATION FOR SEQ ID NO:6:

( i ) SEQUENCE CHARACTERISTICS:
        ( A ) LENGTH: 9323 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

| | | | | | | |
|---|---|---|---|---|---|---|
| CGCCACTTCA | ATTTTGGATT | GTTGAAATTC | AACTAACCAA | AAAGTGCGGT | TAAAATCTGT | 60 |
| GGAGAAAATA | GGTTGTAGTG | AAGAACGAGG | TAATTGTTCA | AAAGGATAAA | GCTCTCTTAA | 120 |
| TTGGGCATTG | GTTGGCGTTT | CTTTTCGGT | TAATAGTAAA | TTATATTCTG | GACGACTATG | 180 |
| CAATCCACCA | ACAACTTTAC | CGTTGGTTTT | AAGCGTTAAT | GTAAGTTCTT | GCTCTTCTTG | 240 |
| GCGAATACGT | AATCCCATTT | TTTGTTTAGC | AAGAAAATGA | TCGGGATAAT | CATAATAGGT | 300 |
| GTTGCCCAAA | AATAAATTTT | GATGTTCTAA | AATCATAAAT | TTTGCAAGAT | ATTGTGGCAA | 360 |
| TTCAATACCT | ATTTGTGGCG | AAATCGCCAA | TTTTAATTCA | ATTTCTTGTA | GCATAATATT | 420 |
| TCCCACTCAA | ATCAACTGGT | TAAATATACA | AGATAATAAA | AATAAATCAA | GATTTTTGTG | 480 |
| ATGACAAACA | ACAATTACAA | CACCTTTTTT | GCAGTCTATA | TGCAAATATT | TTAAAAAAAT | 540 |
| AGTATAAATC | CGCCATATAA | AATGGTATAA | TCTTTCATCT | TTCATCTTTC | ATCTTTCATC | 600 |

```
TTTCATCTTT  CATCTTTCAT  CTTTCATCTT  TCATCTTTCA  TCTTTCATCT  TTCATCTTTC   660
ATCTTTCATC  TTTCATCTTT  CACATGAAAT  GATGAACCGA  GGGAAGGGAG  GGAGGGGCAA   720
GAATGAAGAG  GGAGCTGAAC  GAACGCAAAT  GATAAAGTAA  TTTAATTGTT  CAACTAACCT   780
TAGGAGAAAA  TATGAACAAG  ATATATCGTC  TCAAATTCAG  CAAACGCCTG  AATGCTTTGG   840
TTGCTGTGTC  TGAATTGGCA  CGGGGTTGTG  ACCATTCCAC  AGAAAAGGC   AGCGAAAAAC   900
CTGCTCGCAT  GAAAGTGCGT  CACTTAGCGT  TAAAGCCACT  TTCCGCTATG  TTACTATCTT   960
TAGGTGTAAC  ATCTATTCCA  CAATCTGTTT  TAGCAAGCGG  CAATTTAACA  TCGACCAAAA  1020
TGAAATGGTG  CAGTTTTTAC  AAGAAAACAA  GTAATAAAAC  CATTATCCGC  AACAGTGTTG  1080
ACGCTATCAT  TAATTGGAAA  CAATTTAACA  TCGACCAAAA  TGAAATGGTG  CAGTTTTTAC  1140
AAGAAAACAA  CAACTCCGCC  GTATTCAACC  GTGTTACATC  TAACCAAATC  TCCCAATTAA  1200
AAGGGATTTT  AGATTCTAAC  GGACAAGTCT  TTTTAATCAA  CCCAAATGGT  ATCACAATAG  1260
GTAAAGACGC  AATTATTAAC  ACTAATGGCT  TTACGGCTTC  TACGCTAGAC  ATTTCTAACG  1320
AAAACATCAA  GGCGCGTAAT  TTCACCTTCG  AGCAAACCAA  AGATAAAGCG  CTCGCTGAAA  1380
TTGTGAATCA  CGGTTTAATT  ACTGTCGGTA  AAGACGGCAG  TGTAAATCTT  ATTGGTGGCA  1440
AAGTGAAAAA  CGAGGGTGTG  ATTAGCGTAA  ATGGTGGCAG  CATTTCTTTA  CTCGCAGGGC  1500
AAAAAATCAC  CATCAGCGAT  ATAATAAACC  CAACCATTAC  TTACAGCATT  GCCGCGCCTG  1560
AAAATGAAGC  GGTCAATCTG  GGCGATATTT  TTGCCAAAGG  CGGTAACATT  AATGTCCGTG  1620
CTGCCACTAT  TCGAAACCAA  GGTAAACTTT  CTGCTGATTC  TGTAAGCAAA  GATAAAGCG   1680
GCAATATTGT  TCTTTCCGCC  AAAGAGGGTG  AAGCGGAAAT  TGGCGGTGTA  ATTTCCGCTC  1740
AAAATCAGCA  AGCTAAAGGC  GGCAAGCTGA  TGATAAAGTC  CGATAAAGTC  ACATTAAAAA  1800
CAGGTGCAGT  TATCGACCTT  TCAGGTAAAG  AAGGGGGAGA  AACTTACCTT  GGCGGTGACG  1860
AGCGCGGCGA  AGGTAAAAAC  GGCATTCAAT  TAGCAAAGAA  AACCTCTTTA  GAAAAAGGCT  1920
CAACCATCAA  TGTATCAGGC  AAAGAAAAAG  GCGGACGCGC  TATTGTGTGG  GGCGATATTG  1980
CGTTAATTGA  CGGCAATATT  AACGCTCAAG  GTAGTGGTGA  TATCGCTAAA  ACCGGTGGTT  2040
TTGTGGAGAC  ATCGGGGCAT  TATTTATCCA  TTGACAGCAA  TGCAATTGTT  AAAACAAAAG  2100
AGTGGTTGCT  AGACCCTGAT  GATGTAACAA  TTGAAGCCGA  AGACCCCCTT  CGCAATAATA  2160
CCGGTATAAA  TGATGAATTC  CCAACAGGCA  CCGGTGAAGC  AAGCGACCCT  AAAAAAAATA  2220
GCGAACTCAA  AACAACGCTA  ACCAATACAA  CTATTTCAAA  TTATCTGAAA  AACGCCTGGA  2280
CAATGAATAT  AACGGCATCA  AGAAAACTTA  CCGTTAATAG  CTCAATCAAC  ATCGGAAGCA  2340
ACTCCCACTT  AATTCTCCAT  AGTAAAGGTC  AGCGTGGCGG  AGGCGTTCAG  ATTGATGGAG  2400
ATATTACTTC  TAAAGGCGGA  AATTTAACCA  TTTATTCTGG  CGGATGGGTT  GATGTTCATA  2460
AAAATATTAC  GCTTGATCAG  GGTTTTTTAA  ATATTACCGC  CGCTTCCGTA  GCTTTTGAAG  2520
GTGGAAATAA  CAAAGCACGC  GACGCGGCAA  ATGCTAAAAT  TGTCGCCCAG  GGCACTGTAA  2580
CCATTACAGG  AGAGGGAAAA  GATTTCAGGG  CTAACAACGT  ATCTTTAAAC  GGAACGGGTA  2640
AAGGTCTGAA  TATCATTTCA  TCAGTGAATA  ATTTAACCCA  CAATCTTAGT  GGCACAATTA  2700
ACATATCTGG  GAATATAACA  ATTAACCAAA  CTACGAGAAA  GAACACCTCG  TATTGGCAAA  2760
CCAGCCATGA  TTCGCACTGG  AACGTCAGTG  CTCTTAATCT  AGAGACAGGC  GCAAATTTTA  2820
CCTTTATTAA  ATACATTTCA  AGCAATAGCA  AAGGCTTAAC  AACACAGTAT  AGAAGCTCTG  2880
CAGGGGTGAA  TTTTAACGGC  GTAAATGGCA  ACATGTCATT  CAATCTCAAA  GAAGGAGCGA  2940
AAGTTAATTT  CAAATTAAAA  CCAAACGAGA  ACATGAACAC  AAGCAAACCT  TTACCAATTC  3000
```

```
GGTTTTTAGC   CAATATCACA   GCCACTGGTG   GGGGCTCTGT   TTTTTTTGAT   ATATATGCCA    3060

ACCATTCTGG   CAGAGGGGCT   GAGTTAAAAA   TGAGTGAAAT   TAATATCTCT   AACGGCGCTA    3120

ATTTTACCTT   AAATTCCCAT   GTTCGCGGCG   ATGACGCTTT   TAAAATCAAC   AAAGACTTAA    3180

CCATAAATGC   AACCAATTCA   AATTTCAGCC   TCAGACAGAC   GAAAGATGAT   TTTTATGACG    3240

GGTACGCACG   CAATGCCATC   AATTCAACCT   ACAACATATC   CATTCTGGGC   GGTAATGTCA    3300

CCCTTGGTGG   ACAAAACTCA   AGCAGCAGCA   TTACGGGGAA   TATTACTATC   GAGAAAGCAG    3360

CAAATGTTAC   GCTAGAAGCC   AATAACGCCC   CTAATCAGCA   AACATAAGG    GATAGAGTTA    3420

TAAAACTTGG   CAGCTTGCTC   GTTAATGGGA   GTTAAGTTT    AACTGGCGAA   AATGCAGATA    3480

TTAAAGGCAA   TCTCACTATT   TCAGAAAGCG   CCACTTTTAA   AGGAAAGACT   AGAGATACCC    3540

TAAATATCAC   CGGCAATTTT   ACCAATAATG   GCACTGCCGA   AATTAATATA   ACACAAGGAG    3600

TGGTAAAACT   TGGCAATGTT   ACCAATGATG   GTGATTTAAA   CATTACCACT   CACGCTAAAC    3660

GCAACCAAAG   AAGCATCATC   GGCGGAGATA   TAATCAACAA   AAAAGGAAGC   TTAAATATTA    3720

CAGACAGTAA   TAATGATGCT   GAAATCCAAA   TTGGCGGCAA   TATCTCGCAA   AAAGAAGGCA    3780

ACCTCACGAT   TTCTTCCGAT   AAAATTAATA   TCACCAAACA   GATAACAATC   AAAAGGGTA     3840

TTGATGGAGA   GGACTCTAGT   TCAGATGCGA   CAAGTAATGC   CAACCTAACT   ATTAAAACCA    3900

AAGAATTGAA   ATTGACAGAA   GACCTAAGTA   TTTCAGGTTT   CAATAAAGCA   GAGATTACAG    3960

CCAAAGATGG   TAGAGATTTA   ACTATTGGCA   ACAGTAATGA   CGGTAACAGC   GGTGCCGAAG    4020

CCAAAACAGT   AACTTTTAAC   AATGTTAAAG   ATTCAAAAAT   CTCTGCTGAC   GGTCACAATG    4080

TGACACTAAA   TAGCAAAGTG   AAAACATCTA   GCAGCAATGG   CGGACGTGAA   AGCAATAGCG    4140

ACAACGATAC   CGGCTTAACT   ATTACTGCAA   AAAATGTAGA   AGTAAACAAA   GATATTACTT    4200

CTCTCAAAAC   AGTAAATATC   ACCGCGTCGG   AAAAGGTTAC   CACCACAGCA   GGCTCGACCA    4260

TTAACGCAAC   AAATGGCAAA   GCAAGTATTA   CAACCAAAAC   AGGTGATATC   AGCGGTACGA    4320

TTTCCGGTAA   CACGGTAAGT   GTTAGCGCGA   CTGGTGATTT   AACCACTAAA   TCCGGCTCAA    4380

AAATTGAAGC   GAAATCGGGT   GAGGCTAATG   TAACAAGTGC   AACAGGTACA   ATTGGCGGTA    4440

CAATTTCCGG   TAATACGGTA   AATGTTACGG   CAAACGCTGG   CGATTTAACA   GTTGGGAATG    4500

GCGCAGAAAT   TAATGCGACA   GAAGGAGCTG   CAACCTTAAC   CGCAACAGGG   AATACCTTGA    4560

CTACTGAAGC   CGGTTCTAGC   ATCACTTCAA   CTAAGGGTCA   GGTAGACCTC   TTGGCTCAGA    4620

ATGGTAGCAT   CGCAGGAAGC   ATTAATGCTG   CTAATGTGAC   ATTAAATACT   ACAGGCACCT    4680

TAACCACCGT   GGCAGGCTCG   GATATTAAAG   CAACCAGCGG   CACCTTGGTT   ATTAACGCAA    4740

AAGATGCTAA   GCTAAATGGT   GATGCATCAG   GTGATAGTAC   AGAAGTGAAT   GCAGTCAACG    4800

ACTGGGGATT   TGGTAGTGTG   ACTGCGGCAA   CCTCAAGCAG   TGTGAATATC   ACTGGGGATT    4860

TAAACACAGT   AAATGGGTTA   AATATCATTT   CGAAAGATGG   TAGAAACACT   GTGCGCTTAA    4920

GAGGCAAGGA   AATTGAGGTG   AAATATATCC   AGCCAGGTGT   AGCAAGTGTA   AAGAAGTAA     4980

TTGAAGCGAA   ACGCGTCCTT   GAAAAAGTAA   AAGATTTATC   TGATGAAGAA   AGAGAAACAT    5040

TAGCTAAACT   TGGTGTAAGT   GCTGTACGTT   TTGTTGAGCC   AAATAATACA   ATTACAGTCA    5100

ATACACAAAA   TGAATTTACA   ACCAGACCGT   CAAGTCAAGT   GATAATTTCT   GAAGGTAAGG    5160

CGTGTTTCTC   AAGTGGTAAT   GGCGCACGAG   TATGTACCAA   TGTTGCTGAC   GATGGACAGC    5220

CGTAGTCAGT   AATTGACAAG   GTAGATTTCA   TCCTGCAATG   AAGTCATTTT   ATTTTCGTAT    5280

TATTTACTGT   GTGGGTTAAA   GTTCAGTACG   GGCTTTACCC   ATCTTGTAAA   AAATTACGGA    5340

GAATACAATA   AAGTATTTTT   AACAGGTTAT   TATTATGAAA   AATATAAAAA   GCAGATTAAA    5400
```

```
ACTCAGTGCA  ATATCAGTAT  TGCTTGGCCT  GGCTTCTTCA  TCATTGTATG  CAGAAGAAGC    5460

GTTTTTAGTA  AAAGGCTTTC  AGTTATCTGG  TGCACTTGAA  ACTTTAAGTG  AAGACGCCCA    5520

ACTGTCTGTA  GCAAAATCTT  TATCTAAATA  CCAAGGCTCG  CAAACTTTAA  CAAACCTAAA    5580

AACAGCACAG  CTTGAATTAC  AGGCTGTGCT  AGATAAGATT  GAGCCAAATA  AATTTGATGT    5640

GATATTGCCG  CAACAAACCA  TTACGGATGG  CAATATCATG  TTTGAGCTAG  TCTCGAAATC    5700

AGCCGCAGAA  AGCCAAGTTT  TTTATAAGGC  GAGCCAGGGT  TATAGTGAAG  AAAATATCGC    5760

TCGTAGCCTG  CCATCTTTGA  AACAAGGAAA  AGTGTATGAA  GATGGTCGTC  AGTGGTTCGA    5820

TTTGCGTGAA  TTTAATATGG  CAAAAGAAAA  CCCGCTTAAG  GTTACCCGTG  TACATTACGA    5880

ACTAAACCCT  AAAAACAAAA  CCTCTAATTT  GATAATTGCG  GGCTTCTCGC  CTTTTGGTAA    5940

AACGCGTAGC  TTTATTTCTT  ATGATAATTT  CGGCGCGAGA  GAGTTTAACT  ACCAACGTGT    6000

AAGCTTGGGT  TTTGTTAATG  CCAATTTAAC  TGGTCATGAT  GATGTGTTAA  TTATACCAGT    6060

ATGAGTTATG  CTGATTCTAA  TGATATCGAC  GGCTTACCAA  GTGCGATTAA  TCGTAAATTA    6120

TCAAAGGTC   AATCTATCTC  TGCGAATCTG  AAATGGAGTT  ATTATCTCCC  AACATTTAAC    6180

CTTGGCATGG  AAGACCAATT  TAAAATTAAT  TTAGGCTACA  ACTACCGCCA  TATTAATCAA    6240

ACCTCCGCGT  TAAATCGCTT  GGGTGAAACG  AAGAAAAAAT  TTGCAGTATC  AGGCGTAAGT    6300

GCAGGCATTG  ATGGACATAT  CCAATTTACC  CCTAAAACAA  TCTTTAATAT  TGATTTAACT    6360

CATCATTATT  ACGCGAGTAA  ATTACCAGGC  TCTTTTGGAA  TGGAGCGCAT  GGCGAAACA    6420

TTTAATCGCA  GCTATCACAT  TAGCACAGCC  AGTTAGGGT   TGAGTCAAGA  GTTTGCTCAA    6480

GGTTGGCATT  TTAGCAGTCA  ATTATCAGGT  CAATTTACTC  TACAAGATAT  TAGCAGTATA    6540

GATTTATTCT  CTGTAACAGG  TACTTATGGC  GTCAGAGGCT  TTAAATACGG  CGGTGCAAGT    6600

GGTGAGCGCG  GTCTTGTATG  GCGTAATGAA  TTAAGTATGC  CAAAATACAC  CCGCTTCCAA    6660

ATCAGCCCTT  ATGCGTTTTA  TGATGCAGGT  CAGTTCCGTT  ATAATAGCGA  AAATGCTAAA    6720

ACTTACGGCG  AAGATATGCA  CACGGTATCC  TCTGCGGGTT  TAGGCATTAA  AACCTCTCCT    6780

ACACAAAACT  TAAGCCTAGA  TGCTTTTGTT  GCTCGTCGCT  TTGCAAATGC  CAATAGTGAC    6840

AATTTGAATG  GCAACAAAAA  ACGCACAAGC  TCACCTACAA  CCTTCTGGGG  GAGATTAACA    6900

TTCAGTTTCT  AACCCTGAAA  TTTAATCAAC  TGGTAAGCGT  TCCGCCTACC  AGTTTATAAC    6960

TATATGCTTT  ACCCGCCAAT  TTACAGTCTA  TAGGCAACCC  TGTTTTACC   CTTATATATC    7020

AAATAAACAA  GCTAAGCTGA  GCTAAGCAAA  CCAAGCAAAC  TCAAGCAAGC  CAAGTAATAC    7080

TAAAAAAACA  ATTTATATGA  TAAACTAAAG  TATACTCCAT  GCCATGGCGA  TACAAGGGAT    7140

TTAATAATAT  GACAAAAGAA  AATTTGCAAA  ACGCTCCTCA  AGATGCGACC  GCTTTACTTG    7200

CGGAATTAAG  CAACAATCAA  ACTCCCCTGC  GAATATTTAA  ACAACCACGC  AAGCCCAGCC    7260

TATTACGCTT  GGAACAACAT  ATCGCAAAAA  AAGATTATGA  GTTTGCTTGT  CGTGAATTAA    7320

TGGTGATTCT  GGAAAAAATG  GACGCTAATT  TTGGAGGCGT  TCACGATATT  GAATTTGACG    7380

CACCCGCTCA  GCTGGCATAT  CTACCCGAAA  AATTACTAAT  TTATTTTGCC  ACTCGTCTCG    7440

CTAATGCAAT  TACAACACTC  TTTTCCGACC  CCGAATTGGC  AATTTCTGAA  GAAGGGGCGT    7500

TAAAGATGAT  TAGCCTGCAA  CGCTGGTTGA  CGCTGATTTT  TGCCTCTTCC  CCCTACGTTA    7560

ACGCAGACCA  TATTCTCAAT  AAATATAATA  TCAACCCAGA  TTCCGAAGGT  GGCTTTCATT    7620

TAGCAACAGA  CAACTCTTCT  ATTGCTAAAT  TCTGTATTTT  TTACTTACCC  GAATCCAATG    7680

TCAATATGAG  TTTAGATGCG  TTATGGGCAG  GGAATCAACA  ACTTTGTGCT  TCATTGTGTT    7740

TTGCGTTGCA  GTCTTCACGT  TTTATTGGTA  CCGCATCTGC  GTTTCATAAA  AGAGCGGTGG    7800
```

| | | | | | | |
|---|---|---|---|---|---|---|
| TTTTACAGTG | GTTTCCTAAA | AAACTCGCCG | AAATTGCTAA | TTTAGATGAA | TTGCCTGCAA | 7860 |
| ATATCCTTCA | TGATGTATAT | ATGCACTGCA | GTTATGATTT | AGCAAAAAAC | AAGCACGATG | 7920 |
| TTAAGCGTCC | ATTAAACGAA | CTTGTCCGCA | AGCATATCCT | CACGCAAGGA | TGGCAAGACC | 7980 |
| GCTACCTTTA | CACCTTAGGT | AAAAAGGACG | GCAAACCTGT | GATGATGGTA | CTGCTTGAAC | 8040 |
| ATTTTAATTC | GGGACATTCG | ATTTATCGTA | CACATTCAAC | TTCAATGATT | GCTGCTCGAG | 8100 |
| AAAAATTCTA | TTTAGTCGGC | TTAGGCCATG | AGGGCGTTGA | TAAAATAGGT | CGAGAAGTGT | 8160 |
| TTGACGAGTT | CTTTGAAATC | AGTAGCAATA | ATATAATGGA | GAGACTGTTT | TTTATCCGTA | 8220 |
| AACAGTGCGA | AACTTTCCAA | CCCGCAGTGT | TCTATATGCC | AAGCATTGGC | ATGGATATTA | 8280 |
| CCACGATTTT | TGTGAGCAAC | ACTCGGCTTG | CCCCTATTCA | AGCTGTAGCC | CTGGGTCATC | 8340 |
| CTGCCACTAC | GCATTCTGAA | TTTATTGATT | ATGTCATCGT | AGAAGATGAT | TATGTGGGCA | 8400 |
| GTGAAGATTG | TTTCAGCGAA | ACCCTTTTAC | GCTTACCCAA | AGATGCCCTA | CCTTATGTAC | 8460 |
| CTTCTGCACT | CGCCCCACAA | AAAGTGGATT | ATGTACTCAG | GGAAAACCCT | GAAGTAGTCA | 8520 |
| ATATCGGTAT | TGCCGCTACC | ACAATGAAAT | TAAACCCTGA | ATTTTGCTA | ACATTGCAAG | 8580 |
| AAATCAGAGA | TAAAGCTAAA | GTCAAAATAC | ATTTTCATTT | CGCACTTGGA | CAATCAACAG | 8640 |
| GCTTGACACA | CCCTTATGTC | AAATGGTTTA | TCGAAAGCTA | TTTAGGTGAC | GATGCCACTG | 8700 |
| CACATCCCCA | CGCACCTTAT | CACGATTATC | TGGCAATATT | GCGTGATTGC | GATATGCTAC | 8760 |
| TAAATCCGTT | TCCTTTCGGT | AATACTAACG | GCATAATTGA | TATGGTTACA | TTAGGTTTAG | 8820 |
| TTGGTGTATG | CAAAACGGGG | GATGAAGTAC | ATGAACATAT | TGATGAAGGT | CTGTTTAAAC | 8880 |
| GCTTAGGACT | ACCAGAATGG | CTGATAGCCG | ACACACGAGA | AACATATATT | GAATGTGCTT | 8940 |
| TGCGTCTAGC | AGAAAACCAT | CAAGAACGCC | TTGAACTCCG | TCGTTACATC | ATAGAAAACA | 9000 |
| ACGGCTTACA | AAAGCTTTTT | ACAGGCGACC | CTCGTCCATT | GGGCAAAATA | CTGCTTAAGA | 9060 |
| AAACAAATGA | ATGGAAGCGG | AAGCACTTGA | GTAAAAAATA | ACGGTTTTTT | AAAGTAAAAG | 9120 |
| TGCGGTTAAT | TTTCAAAGCG | TTTTAAAAAC | CTCTCAAAAA | TCAACCGCAC | TTTTATCTTT | 9180 |
| ATAACGATCC | CGCACGCTGA | CAGTTTATCA | GCCTCCCGCC | ATAAAACTCC | GCCTTTCATG | 9240 |
| GCGGAGATTT | TAGCCAAAAC | TGGCAGAAAT | TAAAGGCTAA | AATCACCAAA | TTGCACCACA | 9300 |
| AAATCACCAA | TACCCACAAA | AAA | | | | 9323 |

( 2 ) INFORMATION FOR SEQ ID NO:7:

( i ) SEQUENCE CHARACTERISTICS:
        ( A ) LENGTH: 4287 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

| | | | | | | |
|---|---|---|---|---|---|---|
| GATCAATCTG | GGCGATATTT | TTGCCAAAGG | TGGTAACATT | AATGTCCGCG | CTGCCACTAT | 60 |
| TCGCAATAAA | GGTAAACTTT | CTGCCGACTC | TGTAAGCAAA | GATAAAGTG | GTAACATTGT | 120 |
| TCTCTCTGCC | AAAGAAGGTG | AAGCGGAAAT | TGGCGGTGTA | ATTTCCGCTC | AAAATCAGCA | 180 |
| AGCCAAAGGT | GGTAAGTTGA | TGATTACAGG | CGATAAAGTT | ACATTGAAAA | CGGGTGCACT | 240 |
| TATCGACCTT | TCGGGTAAAG | AAGGGGGAGA | AACTTATCTT | GGCGGTGACG | AGCGTGGCGA | 300 |
| AGGTAAAAAC | GGCATTCAAT | TAGCAAAGAA | AACCACTTTA | GAAAAGGCT | CAACAATTAA | 360 |
| TGTGTCAGGT | AAAGAAAAAG | CTGGGCGCGC | TATTGTATGG | GGCGATATTG | CGTTAATTGA | 420 |

-continued

| | | | | | |
|---|---|---|---|---|---|
| CGGCAATATT | AATGCCCAAG | GTAAAGATAT | CGCTAAAACT | GGTGGTTTTG | TGGAGACGTC | 480 |
| GGGCATTAC | TTATCCATTG | ATGATAACGC | AATTGTTAAA | ACAAAAGAAT | GGCTACTAGA | 540 |
| CCCAGAGAAT | GTGACTATTG | AAGCTCCTTC | CGCTTCTCGC | GTCGAGCTGG | GTGCCGATAG | 600 |
| GAATTCCCAC | TCGGCAGAGG | TGATAAAGT | GACCCTAAAA | AAAAATAACA | CCTCCTTGAC | 660 |
| AACACTAACC | AATACAACCA | TTTCAAATCT | TCTGAAAAGT | GCCCACGTGG | TGAACATAAC | 720 |
| GGCAAGGAGA | AAACTTACCG | TTAATAGCTC | TATCAGTATA | GAAAGAGGCT | CCCACTTAAT | 780 |
| TCTCCACAGT | GAAGGTCAGG | GCGGTCAAGG | TGTTCAGATT | GATAAAGATA | TTACTTCTGA | 840 |
| AGGCGGAAAT | TTAACCATTT | ATTCTGGCGG | ATGGGTTGAT | GTTCATAAAA | ATATTACGCT | 900 |
| TGGTAGCGGC | TTTTTAAACA | TCACAACTAA | AGAAGGAGAT | ATCGCCTTCG | AAGACAAGTC | 960 |
| TGGACGGAAC | AACCTAACCA | TTACAGCCCA | AGGGACCATC | ACCTCAGGTA | ATAGTAACGG | 1020 |
| CTTTAGATTT | AACAACGTCT | CTCTAAACAG | CCTTGGCGGA | AAGCTGAGCT | TTACTGACAG | 1080 |
| CAGAGAGGAC | AGAGGTAGAA | GAACTAAGGG | TAATATCTCA | ACAAATTTG | ACGGAACGTT | 1140 |
| AAACATTTCC | GGAACTGTAG | ATATCTCAAT | GAAAGCACCC | AAAGTCAGCT | GGTTTTACAG | 1200 |
| AGACAAAGGA | CGCACCTACT | GGAACGTAAC | CACTTTAAAT | GTTACCTCGG | GTAGTAAATT | 1260 |
| TAACCTCTCC | ATTGACAGCA | CAGGAAGTGG | CTCAACAGGT | CCAAGCATAC | GCAATGCAGA | 1320 |
| ATTAAATGGC | ATAACATTTA | ATAAAGCCAC | TTTTAATATC | GCACAAGGCT | CAACAGCTAA | 1380 |
| CTTTAGCATC | AAGGCATCAA | TAATGCCCTT | TAAGAGTAAC | GCTAACTACG | CATTATTTAA | 1440 |
| TGAAGATATT | TCAGTCTCAG | GGGGGGGTAG | CGTTAATTTC | AAACTTAACG | CCTCATCTAG | 1500 |
| CAACATACAA | ACCCCTGGCG | TAATTATAAA | ATCTCAAAAC | TTTAATGTCT | CAGGAGGGTC | 1560 |
| AACTTTAAAT | CTCAAGGCTG | AAGGTTCAAC | AGAAACCGCT | TTTTCAATAG | AAAATGATTT | 1620 |
| AAACTTAAAC | GCCACCGGTG | GCAATATAAC | AATCAGACAA | GTCGAGGGTA | CCGATTCACG | 1680 |
| CGTCAACAAA | GGTGTCGCAG | CCAAAAAAAA | CATAACTTTT | AAGGGGGTA | ATATCACCTT | 1740 |
| CGGCTCTCAA | AAAGCCACAA | CAGAAATCAA | AGGCAATGTT | ACCATCAATA | AAAACACTAA | 1800 |
| CGCTACTCTT | CGTGGTGCGA | ATTTTGCCGA | AAACAAATCG | CCTTTAAATA | TAGCAGGAAA | 1860 |
| TGTTATTAAT | AATGGCAACC | TTACCACTGC | CGGCTCCATT | ATCAATATAG | CCGGAAATCT | 1920 |
| TACTGTTTCA | AAAGGCGCTA | ACCTTCAAGC | TATAACAAAT | TACACTTTTA | ATGTAGCCGG | 1980 |
| CTCATTTGAC | AACAATGGCG | CTTCAAACAT | TTCCATTGCC | AGAGGAGGGG | CTAAATTTAA | 2040 |
| AGATATCAAT | AACACCAGTA | GCTTAAATAT | TACCACCAAC | TCTGATACCA | CTTACCGCAC | 2100 |
| CATTATAAAA | GGCAATATAT | CCAACAAATC | AGGTGATTTG | AATATTATTG | ATAAAAAAAG | 2160 |
| CGACGCTGAA | ATCCAAATTG | GCGGCAATAT | CTCACAAAAA | GAAGGCAATC | TCACAATTTC | 2220 |
| TTCTGATAAA | GTAAATATTA | CCAATCAGAT | AACAATCAAA | GCAGGCGTTG | AAGGGGGGCG | 2280 |
| TTCTGATTCA | AGTGAGGCAG | AAAATGCTAA | CCTAACTATT | CAAACCAAAG | AGTTAAAATT | 2340 |
| GGCAGGAGAC | CTAAATATTT | CAGGCTTTAA | TAAAGCAGAA | ATTACAGCTA | AAAATGGCAG | 2400 |
| TGATTTAACT | ATTGGCAATG | CTAGCGGTGG | TAATGCTGAT | GCTAAAAAAG | TGACTTTTGA | 2460 |
| CAAGGTTAAA | GATTCAAAAA | TCTCGACTGA | CGGTCACAAT | GTAACACTAA | ATAGCGAAGT | 2520 |
| GAAAACGTCT | AATGGTAGTA | GCAATGCTGG | TAATGATAAC | AGCACCGGTT | TAACCATTTC | 2580 |
| CGCAAAAGAT | GTAACGGTAA | ACAATAACGT | TACCTCCCAC | AAGACAATAA | ATATCTCTGC | 2640 |
| CGCAGCAGGA | AATGTAACAA | CCAAAGAAGG | CACAACTATC | AATGCAACCA | CAGGCAGCGT | 2700 |
| GGAAGTAACT | GCTCAAAATG | GTACAATTAA | AGGCAACATT | ACCTCGCAAA | ATGTAACAGT | 2760 |
| GACAGCAACA | GAAAATCTTG | TTACCACAGA | GAATGCTGTC | ATTAATGCAA | CCAGCGGCAC | 2820 |

```
AGTAAACATT  AGTACAAAAA  CAGGGGATAT  TAAAGGTGGA  ATTGAATCAA  CTTCCGGTAA    2880

TGTAAATATT  ACAGCGAGCG  GCAATACACT  TAAGGTAAGT  AATATCACTG  GTCAAGATGT    2940

AACAGTAACA  GCGGATGCAG  GAGCCTTGAC  AACTACAGCA  GGCTCAACCA  TTAGTGCGAC    3000

AACAGGCAAT  GCAAATATTA  CAACCAAAAC  AGGTGATATC  AACGGTAAAG  TTGAATCCAG    3060

CTCCGGCTCT  GTAACACTTG  TTGCAACTGG  AGCAACTCTT  GCTGTAGGTA  ATATTTCAGG    3120

TAACACTGTT  ACTATTACTG  CGGATAGCGG  TAAATTAACC  TCCACAGTAG  GTTCTACAAT    3180

TAATGGGACT  AATAGTGTAA  CCACCTCAAG  CCAATCAGGC  GATATTGAAG  GTACAATTTC    3240

TGGTAATACA  GTAAATGTTA  CAGCAAGCAC  TGGTGATTTA  ACTATTGGAA  ATAGTGCAAA    3300

AGTTGAAGCG  AAAAATGGAG  CTGCAACCTT  AACTGCTGAA  TCAGGCAAAT  TAACCACCCA    3360

AACAGGCTCT  AGCATTACCT  CAAGCAATGG  TCAGACAACT  CTTACAGCCA  AGGATAGCAG    3420

TATCGCAGGA  AACATTAATG  CTGCTAATGT  GACGTTAAAT  ACCACAGGCA  CTTTAACTAC    3480

TACAGGGGAT  TCAAAGATTA  ACGCAACCAG  TGGTACCTTA  ACAATCAATG  CAAAAGATGC    3540

CAAATTAGAT  GGTGCTGCAT  CAGGTGACCG  CACAGTAGTA  AATGCAACTA  ACGCAAGTGG    3600

CTCTGGTAAC  GTGACTGCGA  AAACCTCAAG  CAGCGTGAAT  ATCACCGGGG  ATTTAAACAC    3660

AATAAATGGG  TTAAATATCA  TTTCGGAAAA  TGGTAGAAAC  ACTGTGCGCT  TAAGAGGCAA    3720

GGAAATTGAT  GTGAAATATA  TCCAACCAGG  TGTAGCAAGC  GTAGAAGAGG  TAATTGAAGC    3780

GAAACGCGTC  CTTGAGAAGG  TAAAAGATTT  ATCTGATGAA  GAAAGAGAAA  CACTAGCCAA    3840

ACTTGGTGTA  AGTGCTGTAC  GTTTCGTTGA  GCCAAATAAT  GCCATTACGG  TTAATACACA    3900

AAACGAGTTT  ACAACCAAAC  CATCAAGTCA  AGTGACAATT  TCTGAAGGTA  AGGCGTGTTT    3960

CTCAAGTGGT  AATGGCGCAC  GAGTATGTAC  CAATGTTGCT  GACGATGGAC  AGCAGTAGTC    4020

AGTAATTGAC  AAGGTAGATT  TCATCCTGCA  ATGAAGTCAT  TTTATTTTCG  TATTATTTAC    4080

TGTGTGGGTT  AAAGTTCAGT  ACGGGCTTTA  CCCACCTTGT  AAAAAATTAC  GAAAAATACA    4140

ATAAAGTATT  TTTAACAGGT  TATTATTATG  AAAAACATAA  AAAGCAGATT  AAAACTCAGT    4200

GCAATATCAA  TATTGCTTGG  CTTGGCTTCT  TCATCGACGT  ATGCAGAAGA  AGCGTTTTTA    4260

GTAAAAGGCT  TTCAGTTATC  TGGCGCG                                           4287
```

( 2 ) INFORMATION FOR SEQ ID NO:8:

( i ) SEQUENCE CHARACTERISTICS:
  ( A ) LENGTH: 4702 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:8:

```
GGGAATGAGC  GTCGTACACG  GTACAGCAAC  CATGCAAGTA  GACGGCAATA  AAACCACTAT      60

CCGTAATAGC  ATCAATGCTA  TCATCAATTG  GAAACAATTT  AACATTGACC  AAAATGAAAT     120

GGAGCAGTTT  TTACAAGAAA  GCAGCAACTC  TGCCGTTTTC  AACCGTGTTA  CATCTGACCA     180

AATCTCCCAA  TTAAAAGGGA  TTTTAGATTC  TAACGGACAA  GTCTTTTTAA  TCAACCCAAA     240

TGGTATCACA  ATAGGTAAAG  ACGCAATTAT  TAACACTAAT  GGCTTTACTG  CTTCTACGCT     300

AGACATTTCT  AACGAAAACA  TCAAGGCGCG  TAATTTCACC  CTTGAGCAAA  CCAAGGATAA     360

AGCACTCGCT  GAAATCGTGA  ATCACGGTTT  AATTACCGTT  GGTAAAGACG  GTAGCGTAAA     420

CCTTATTGGT  GGCAAAGTGA  AAAACGAGGG  CGTGATTAGC  GTAAATGGCG  GTAGTATTTC     480

TTTACTTGCA  GGGCAAAAAA  TCACCATCAG  CGATATAATA  AATCCAACCA  TCACTTACAG     540
```

| | | | | | | |
|---|---|---|---|---|---|---|
| CATTGCTGCA | CCTGAAAACG | AAGCGATCAA | TCTGGGCGAT | ATTTTTGCCA | AAGGTGGTAA | 600 |
| CATTAATGTC | CGCGCTGCCA | CTATTCGCAA | TAAAGGTAAA | CTTTCTGCCG | ACTCTGTAAG | 660 |
| CAAAGATAAA | AGTGGTAACA | TTGTTCTCTC | TGCCAAAGAA | GGTGAAGCGG | AAATTGGCGG | 720 |
| TGTAATTTCC | GCTCAAAATC | AGCAAGCCAA | AGGTGGTAAG | TTGATGATTA | CAGGTGATAA | 780 |
| AGTCACATTA | AAAACAGGTG | CAGTTATCGA | CCTTTCAGGT | AAGAAGGGG | GAGAGACTTA | 840 |
| TCTTGGCGGT | GATGAGCGTG | GCGAAGGTAA | AAATGGTATT | CAATTAGCGA | AGAAAACCTC | 900 |
| TTTAGAAAAA | GGCTCGACAA | TTAATGTATC | AGGCAAAGAA | AAAGGCGGGC | GCGCTATTGT | 960 |
| ATGGGGCGAT | ATTGCATTAA | TTAATGGTAA | CATTAATGCT | CAAGGTAGCG | ATATTGCTAA | 1020 |
| AACTGGCGGC | TTTGTGGAAA | CATCAGGACA | TGACTTATCC | ATTGGTGATG | ATGTGATTGT | 1080 |
| TGACGCTAAA | GAGTGGTTAT | TAGACCCAGA | TGATGTGTCC | ATTGAAACTC | TTACATCTGG | 1140 |
| ACGCAATAAT | ACCGGCGAAA | ACCAAGGATA | TACAACAGGA | GATGGGACTA | AAGAGTCACC | 1200 |
| TAAAGGTAAT | AGTATTTCTA | AACCTACATT | AACAAACTCA | ACTCTTGAGC | AAATCCTAAG | 1260 |
| AAGAGGTTCT | TATGTTAATA | TCACTGCTAA | TAATAGAATT | TATGTTAATA | GCTCCATCAA | 1320 |
| CTTATCTAAT | GGCAGTTTAA | CACTTCACAC | TAAACGAGAT | GGAGTTAAAA | TTAACGGTGA | 1380 |
| TATTACCTCA | AACGAAAATG | GTAATTTAAC | CATTAAAGCA | GGCTCTTGGG | TTGATGTTCA | 1440 |
| TAAAAACATC | ACGCTTGGTA | CGGGTTTTTT | CAATATTGTC | GCTGGGGATT | CTGTAGCTTT | 1500 |
| TGAGAGAGAG | GGCGATAAAG | CACGTAACGC | AACAGATGCT | CAAATTACCG | CACAAGGGAC | 1560 |
| GATAACCGTC | AATAAGATG | ATAAACAATT | TAGATTCAAT | AATGTATCTA | TTAACGGGAC | 1620 |
| GGGCAAGGGT | TTAAAGTTTA | TTGCAAATCA | AAATAATTTC | ACTCATAAAT | TGATGGCGA | 1680 |
| AATTAACATA | TCTGGAATAG | TAACAATTAA | CCAAACCACG | AAAAAGATG | TTAAATACTG | 1740 |
| GAATGCATCA | AAAGACTCTT | ACTGGAATGT | TTCTTCTCTT | ACTTGAATA | CGGTGCAAAA | 1800 |
| ATTTACCTTT | ATAAAATTCG | TTGATAGCGG | CTCAAATTCC | CAAGATTTGA | GGTCATCACG | 1860 |
| TAGAAGTTTT | GCAGGCGTAC | ATTTTAACGG | CATCGGAGGC | AAAACAAACT | TCAACATCGG | 1920 |
| AGCTAACGCA | AAAGCCTTAT | TTAAATTAAA | ACCAAACGCC | GCTACAGACC | CAAAAAAGA | 1980 |
| ATTACCTATT | ACTTTTAACG | CCAACATTAC | AGCTACCGGT | AACAGTGATA | GCTCTGTGAT | 2040 |
| GTTTGACATA | CACGCCAATC | TTACCTCTAG | AGCTGCCGGC | ATAAACATGG | ATTCAATTAA | 2100 |
| CATTACCGGC | GGGCTTGACT | TTTCCATAAC | ATCCCATAAT | CGCAATAGTA | ATGCTTTTGA | 2160 |
| AATCAAAAAA | GACTTAACTA | TAAATGCAAC | TGGCTCGAAT | TTTAGTCTTA | AGCAAACGAA | 2220 |
| AGATTCTTTT | TATAATGAAT | ACAGCAAACA | CGCCATTAAC | TCAAGTCATA | ATCTAACCAT | 2280 |
| TCTTGGCGGC | AATGTCACTC | TAGGTGGGGA | AAATTCAAGC | AGTAGCATTA | CGGGCAATAT | 2340 |
| CAATATCACC | AATAAAGCAA | ATGTTACATT | ACAAGCTGAC | ACCAGCAACA | GCAACACAGG | 2400 |
| CTTGAAGAAA | AGAACTCTAA | CTCTTGGCAA | TATATCTGTT | GAGGGGAATT | TAAGCCTAAC | 2460 |
| TGGTGCAAAT | GCAAACATTG | TCGGCAATCT | TTCTATTGCA | GAAGATTCCA | CATTTAAAGG | 2520 |
| AGAAGCCAGT | GACAACCTAA | ACATCACCGG | CACCTTTACC | AACAACGGTA | CCGCCAACAT | 2580 |
| TAATATAAAA | CAAGGAGTGG | TAAAACTCCA | AGGCGATATT | ATCAATAAAG | GTGGTTTAAA | 2640 |
| TATCACTACT | AACGCCTCAG | GCACTCAAAA | AACCATTATT | AACGGAAATA | TAACTAACGA | 2700 |
| AAAAGGCGAC | TTAAACATCA | AGAATATTAA | AGCCGACGCC | GAAATCCAAA | TTGGCGGCAA | 2760 |
| TATCTCACAA | AAAGAAGGCA | ATCTCACAAT | TTCTTCTGAT | AAAGTAAATA | TTACCAATCA | 2820 |
| GATAACAATC | AAAGCAGGCG | TTGAAGGGGG | GCGTTCTGAT | TCAAGTGAGG | CAGAAAATGC | 2880 |
| TAACCTAACT | ATTCAAACCA | AAGAGTTAAA | ATTGGCAGGA | GACCTAAATA | TTTCAGGCTT | 2940 |

| | | | | | | |
|---|---|---|---|---|---|---|
| TAATAAAGCA | GAAATTACAG | CTAAAAATGG | CAGTGATTTA | ACTATTGGCA | ATGCTAGCGG | 3000 |
| TGGTAATGCT | GATGCTAAAA | AAGTGACTTT | TGACAAGGTT | AAAGATTCAA | AAATCTCGAC | 3060 |
| TGACGGTCAC | AATGTAACAC | TAAATAGCGA | AGTGAAAACG | TCTAATGGTA | GTAGCAATGC | 3120 |
| TGGTAATGAT | AACAGCACCG | GTTAACCAT | TTCCGCAAAA | GATGTAACGG | TAAACAATAA | 3180 |
| CGTTACCTCC | CACAAGACAA | TAAATATCTC | TGCCGCAGCA | GGAAATGTAA | CAACCAAAGA | 3240 |
| AGGCACAACT | ATCAATGCAA | CCACAGGCAG | CGTGGAAGTA | ACTGCTCAAA | ATGGTACAAT | 3300 |
| TAAAGGCAAC | ATTACCTCGC | AAAATGTAAC | AGTGACAGCA | ACAGAAAATC | TTGTTACCAC | 3360 |
| AGAGAATGCT | GTCATTAATG | CAACCAGCGG | CACAGTAAAC | ATTAGTACAA | AAACAGGGGA | 3420 |
| TATTAAAGGT | GGAATTGAAT | CAACTTCCGG | TAATGTAAAT | ATTACAGCGA | GCGGCAATAC | 3480 |
| ACTTAAGGTA | AGTAATATCA | CTGGTCAAGA | TGTAACAGTA | ACAGCGGATG | CAGGAGCCTT | 3540 |
| GACAACTACA | GCAGGCTCAA | CCATTAGTGC | GACAACAGGC | AATGCAAATA | TTACAACCAA | 3600 |
| AACAGGTGAT | ATCAACGGTA | AAGTTGAATC | CAGCTCCGGC | TCTGTAACAC | TTGTTGCAAC | 3660 |
| TGGAGCAACT | CTTGCTGTAG | GTAATATTTC | AGGTAACACT | GTTACTATTA | CTGCGGATAG | 3720 |
| CGGTAAATTA | ACCTCCACAG | TAGGTTCTAC | AATTAATGGG | ACTAATAGTG | TAACCACCTC | 3780 |
| AAGCCAATCA | GGCGATATTG | AAGGTACAAT | TTCTGGTAAT | ACAGTAAATG | TTACAGCAAG | 3840 |
| CACTGGTGAT | TTAACTATTG | GAAATAGTGC | AAAAGTTGAA | GCGAAAAATG | GAGCTGCAAC | 3900 |
| CTTAACTGCT | GAATCAGGCA | AATTAACCAC | CCAAACAGGC | TCTAGCATTA | CCTCAAGCAA | 3960 |
| TGGTCAGACA | ACTCTTACAG | CCAAGGATAG | CAGTATCGCA | GGAAACATTA | ATGCTGCTAA | 4020 |
| TGTGACGTTA | AATACCACAG | GCACTTTAAC | TACTACAGGG | GATTCAAAGA | TTAACGCAAC | 4080 |
| CAGTGGTACC | TTAACAATCA | ATGCAAAAGA | TGCCAAATTA | GATGGTGCTG | CATCAGGTGA | 4140 |
| CCGCACAGTA | GTAAATGCAA | CTAACGCAAG | TGGCTCTGGT | AACGTGACTG | CGAAAACCTC | 4200 |
| AAGCAGCGTG | AATATCACCG | GGGATTTAAA | CACAATAAAT | GGGTTAAATA | TCATTTCGGA | 4260 |
| AAATGGTAGA | AACACTGTGC | GCTTAAGAGG | CAAGGAAATT | GATGTGAAAT | ATATCCAACC | 4320 |
| AGGTGTAGCA | AGCGTAGAAG | AGGTAATTGA | AGCGAAACGC | GTCCTTGAGA | AGGTAAAAGA | 4380 |
| TTTATCTGAT | GAAGAAAGAG | AAACACTAGC | CAAACTTGGT | GTAAGTGCTG | TACGTTTCGT | 4440 |
| TGAGCCAAAT | AATGCCATTA | CGGTTAATAC | ACAAAACGAG | TTTACAACCA | AACCATCAAG | 4500 |
| TCAAGTGACA | ATTTCTGAAG | GTAAGGCGTG | TTTCTCAAGT | GGTAATGGCG | CACGAGTATG | 4560 |
| TACCAATGTT | GCTGACGATG | GACAGCAGTA | GTCAGTAATT | GACAAGGTAG | ATTTCATCCT | 4620 |
| GCAATGAAGT | CATTTTATTT | TCGTATTATT | TACTGTGTGG | GTTAAAGTTC | AGTACGGGCT | 4680 |
| TTACCCACCT | TGTAAAAAAT | TA | | | | 4702 |

What I claim is:

1. An isolated and purified gene which encodes a high molecular weight protein having the amino acid sequence of SEQ ID: 2.

2. The gene of claim 1 having the DNA sequence of SEQ ID: 1.

3. The isolated and purified gene cluster of a non-typeable Haemophilus strain comprising the sequence of SEQ ID: 5.

* * * * *